(12) United States Patent
Fujii et al.

(10) Patent No.: US 7,074,204 B2
(45) Date of Patent: Jul. 11, 2006

(54) GARMENT

(75) Inventors: Takako Fujii, Kyoto (JP); Risa Saka, Kyoto (JP); Toshiko Murakami, Kyoto (JP)

(73) Assignee: Wacoal Corp., Kyoto (JP)

( * ) Notice: Subject to any disclaimer, the term of this patent is extended or adjusted under 35 U.S.C. 154(b) by 69 days.

(21) Appl. No.: 10/088,719

(22) PCT Filed: Dec. 11, 2000

(86) PCT No.: PCT/JP00/08756

§ 371 (c)(1),
(2), (4) Date: Jun. 19, 2002

(87) PCT Pub. No.: WO02/47501

PCT Pub. Date: Jun. 20, 2002

(65) Prior Publication Data

US 2003/0028952 A1    Feb. 13, 2003

(51) Int. Cl.
*A61F 13/00* (2006.01)
*A61F 13/06* (2006.01)

(52) U.S. Cl. .................... 602/75; 602/60; 602/61; 602/67; 450/95; 128/96.1; 128/99.1

(58) Field of Classification Search .............. 602/75, 602/60, 61, 67; 128/96.1, 99.1, 100.1, 95.1, 128/98.1; 2/464, 466; 450/94, 95, 99, 115
See application file for complete search history.

(56) References Cited

U.S. PATENT DOCUMENTS

| | | | | |
|---|---|---|---|---|
| 3,523,540 A | * | 8/1970 | Morehouse | ................. 450/115 |
| 3,524,449 A | * | 8/1970 | Peters | ......................... 450/100 |
| 3,756,247 A | * | 9/1973 | Hand | ............................ 450/94 |
| 4,576,154 A | * | 3/1986 | Hyman et al. | ................ 602/19 |
| 4,698,847 A | | 10/1987 | Yoshihara | |
| 5,201,074 A | | 4/1993 | Dicker | |
| 5,390,512 A | | 2/1995 | Mista | ........................... 66/205 |
| 5,640,714 A | * | 6/1997 | Tanaka | ............................. 2/22 |
| 6,080,125 A | * | 6/2000 | Mott | ............................ 602/61 |
| 6,186,970 B1 | * | 2/2001 | Fujii et al. | .................... 602/75 |

FOREIGN PATENT DOCUMENTS

EP    1016351 A    7/2000

(Continued)

OTHER PUBLICATIONS

Merriam-Webster OnLine Dictionary, "APEX", printed Nov. 3, 2005, 2 pages.*

*Primary Examiner*—Henry Bennett
*Assistant Examiner*—Amanda Wieker
(74) *Attorney, Agent, or Firm*—Darby & Darby

(57) ABSTRACT

A garment comprising a stretch fabric wherein the garment covers at least a part of the lower body of a wearer, has a crotch part, and is worn by being fitted to the wearer's body, wherein the garment in part has a first portion with a strong straining force; first portion with a strong straining force is a strong straining portion (A); right and left parts of the portion (A) are connected at a second position on the back side of the garment corresponding to any region from os sacrum to vertebrae lumbalis of the wearer's body; and the portion (A) covers a region extending from second position through tops of bulges of the buttocks or vicinities thereof approximately in the direction of muscle fibers of musculus gluteus maximus at right and left to at least the vicinity of trochanter major.

25 Claims, 71 Drawing Sheets

FOREIGN PATENT DOCUMENTS

| | | |
|---|---|---|
| EP | 1136001 A | 9/2001 |
| JP | 64-37407 U | 3/1989 |
| JP | 2-30318 U | 2/1990 |
| JP | 02182903 A | 7/1990 |
| JP | 6-12412 U | 2/1994 |
| JP | 10-8303 A | 1/1998 |
| JP | 10-212606 A | 8/1998 |
| JP | 3061048 U | 6/1999 |
| JP | 2002235207 A * | 8/2002 |
| JP | 2002238931 A * | 8/2002 |
| WO | WO9821987 * | 11/1996 |
| WO | 98/21987 | 5/1998 |
| WO | WO-99/04660 A1 | 2/1999 |
| WO | 99/53779 | 10/1999 |

* cited by examiner

GARMENT

TECHNICAL FIELD

The present invention relates to a garment having functions of assisting the stability of the hip joint and reducing lumbar lordosis.

BACKGROUND ART

Aging, lack of exercises, or excessive use of muscles by exercises may cause disorder in posture or excess load to some muscles. As a result, generation of pains or limitations in movements may be caused.

Particularly in lumbar region, this may lead to limitations in movements and inconveniences as follows: due to weakened abdominal muscles for supporting musculus erector spinae, lumbar lordosis is increased; due to weakened musculus gluteus maximus and musculus gluteus medius that play important roles as muscles for stabilizing the tilt of the pelvis and allowing the hip joint to function with stability, and further due to weakened musculus biceps femoris, musculus semitendinosus, musculus semimembranosus, etc. that are called hamstrings, the pelvis is liable to incline backward and lumbar pains are generated; and due to weakened hamstrings, the function of musculus obliquus externus abdominis does not work well, and the upper body cannot be supported adequately, so that the supporting point when rotating the hips is not fixed, and the hips are not rotated (twisted) smoothly.

Furthermore, backward inclination of the pelvis causes the hips to be flat. Coupled with lumbar lordosis, it also causes flank muscles to be creased and compressed, and also causes the twisting angle of the hips to the right and left to decrease. As a result, the entire figure becomes like an elderly person, and moreover, broken posture causes not only lumbar pains, but also indirectly causes knee joint pain.

Conventionally, a garment for figure control has been proposed in which, in order to provide a figure control function, for example, the function of keeping the bulges of the hips in a high position, a cloth piece is applied onto a predetermined part of the garment main body to increase the straining force in the predetermined part. Sports tights for supporting specific muscles in order to assist the wearer's abilities of exercises such as sports, etc. also have been proposed.

To prevent the above-described lumbar lordosis and stabilize the hip joint, thereby preventing lumbar pains and limitations in movements and reducing the limitations in the movements of the hip joint, for example, the following methods have been used in general as conventional methods:

(1) applying a taping to lumbar region, hypogastric region, etc.; and (2) wearing a belt-like corset by winding it around lumbar region, hypogastric region, etc. in the same manner as in (1).

However, in the method (1), it is difficult to perform a taping by oneself, so that it is necessary to have another person perform a taping. Because an inexperienced person cannot perform a taping, it is necessary to have an expert perform a taping each time, so that it is inconvenient to attach and remove the taping. In addition, a taping cannot be worn for a long time and also may cause skin disorder.

As the method (2), there is a method in which lumbar pains are alleviated by increasing abdominal pressure or preventing hyperextension of vertebrae lumbalis so as to reduce the load to the back muscles. There is another method in which it is intended to stabilize the hip joint by pressing the hip joint strongly and circularly. However, these methods limit the movements of the wearer exceedingly, and during daily activities or when playing sports, etc., the corset has very poor wearing comfort and is hard to wear.

OBJECTS AND SUMMARY OF THE INVENTION

It is an object of the present invention to provide a garment that has good wearing comfort in common occasions such as during daily activities or when playing sports; can be worn easily by oneself even for an inexperienced person; has the functions of increasing the stability of the hip joint, making youthful figure and posture, and reducing lumbar lordosis; contributes to alleviating pains such as lumbar pains; and further has the functions of enabling the wearer to improve his/her performances when playing sports, and for an elderly person preventing falling down, by utilizing the function of expanding the range of motion of the lumbar region or the hip joint of a human body.

To accomplish the above object, the present invention provides a garment as follows:

(1) A garment comprising a stretch fabric wherein the garment covers at least a part of the lower body of a wearer, has a crotch part, and is worn by being fitted to the wearer's body, wherein:

the garment in part has a portion with a strong straining force;

the portion with a strong straining force is a strong straining portion (A);

right and left parts of the portion (A) are connected at a position on the back side of the garment corresponding to any region from os sacrum to vertebrae lumbalis of the wearer's body; and the portion (A) covers a region extending from said position through tops of bulges of the buttocks or vicinities thereof approximately in the direction of muscle fibers of musculus gluteus maximus at right and left to at least the vicinity of trochanter major.

(2) The garment according to the above item (1), further comprising a strong straining portion (B), wherein:

right and left parts of the portion (B) are connected at a position on the garment corresponding to musculus rectus abdominis in hypogastric region; and the portion (B) covers a region extending obliquely downward from the position on musculus rectus abdominis in hypogastric region approximately in the direction of muscle fibers of musculus obliquus internus abdominis at right and left to at least the vicinity of trochanter major.

(3) The garment according to the above item (1) or (2), further comprising a strong straining portion (C), wherein:

right and left parts of the portion (C) are connected at a position on the garment corresponding to musculus rectus abdominis in hypogastric region; and the portion (C) covers a region extending obliquely upward from the position on musculus rectus abdominis in hypogastric region approximately in the direction of muscle fibers of musculus obliquus externus abdominis at right and left to at least a position exceeding the sides of the wearer to the back side.

(4) The garment according to any one of the above items (1) to (3), further comprising a strong straining portion (D), wherein:

right and left parts of the portion (D) are connected approximately in the vicinity of a position on the garment corresponding to the back center of the waist; and the portion (D) covers a region extending from the vicinity of the position at the back center of the waist through musculus latissimus dorsi and musculus gluteus medius at right and left and a part of musculus obliquus externus abdominis to at least a position exceeding the sides of the wearer to the front side.

(5) The garment according to the above item (1), further comprising the portion (B) of the above item (2) and the portion (C) of the above item (3).

(6) The garment according to the above item (1), further comprising the portion (B) of the above item (2), the portion (C) of the above item (3), and the portion (D) of the above item (4).

(7) The garment according to the above item (1), further comprising a strong straining portion (F) for pressing abdomen and a strong straining portion (B), wherein:

the portion (F) has a main stretch direction in the longitudinal direction of the garment;

the portion (F) covers the center of hypogastric region;

an end of the portion (B) is connected to each of right and left lower sides of the portion (F); and the portion (B) covers a region extending obliquely downward from the right and left lower sides of the portion (F) approximately in the directions of muscle fibers of musculus obliquus internus abdominis at right and left to at least the vicinity of trochanter major.

(8) The garment according to the above item (1), further comprising a strong straining portion (F) for pressing abdomen and a strong straining portion (C), wherein:

the portion (F) has a main stretch direction in the longitudinal direction of the garment;

the portion (F) covers the center of hypogastric region;

an end of the portion (C) is connected to each of right and left upper sides of the portion (F); and the portion (C) covers a region extending obliquely upward from the right and left upper sides of the portion (F) approximately in the direction of muscle fibers of musculus obliquus externus abdominis at right and left to at least a position exceeding the sides of the wearer to the back side.

(9) The garment according to the above item (1), further comprising a strong straining portion (F) for pressing abdomen, a strong straining portion (B), and a strong straining portion (C), wherein:

the portion (F) has a main stretch direction in the longitudinal direction of the garment;

the portion (F) covers the center of hypogastric region;

an end of the portion (B) is connected to each of right and left lower sides of the portion (F);

the portion (B) covers a region extending obliquely downward from the right and left lower sides of the portion (F) approximately in the directions of muscle fibers of musculus obliquus internus abdominis at right and left to at least the vicinity of trochanter major;

an end of the portion (C) is connected to each of right and left upper sides of the portion (F); and the portion (C) covers a region extending obliquely upward from the right and left upper sides of the portion (F) approximately in the direction of muscle fibers of musculus obliquus externus abdominis at right and left to at least a position exceeding the sides of the wearer to the back side.

(10) The garment according to any one of the above items (1) to (9), wherein:

the portion indicated by the portion (A) is a strong straining portion (A2); and the portion (A2) further covers a region extending from the vicinity of trochanter major toward regio femoralis anterior medialis through at least a part of any at least one musculus quadriceps femoris selected from musculus sartorius, musculus rectus femoris and musculus vastus medialis.

(11) The garment according to any one of the above items (1) to (9), wherein:

the portion indicated by the portion (A) is a strong straining portion (A3); and the portion (A3) further covers a region extending from the vicinity of trochanter major through the vicinity of tractus iliotibialis and/or musculus vastus lateralis in regio femoralis to a position a little higher than patella.

(12) The garment according to any one of the above items (1) to (9), wherein:

the portion indicated by the portion (A) is a strong straining portion (A4); and the portion (A4) further covers a region extending from the vicinity of trochanter major through the vicinity of tractus iliotibialis and/or musculus vastus lateralis to patella, and further from patella through the vicinity of musculus gastrocnemius and/or musculus soleus in the regio cruris lateralis to the vicinity of an upper part of malleolus lateralis so as to support musculus gastrocnemius and musculus soleus.

(13) The garment according to any one of the above items (2) to (12), wherein:

the portion indicated by the portion (B) is a strong straining portion (B2); and the portion (B2) further covers a region extending from the vicinity of trochanter major through a lower part of the bulges of the buttocks.

(14) The garment according to any one of the above items (2) to (12), wherein:

the portion indicated by the portion (B) is a strong straining portion (B3); and the portion (B3) further covers a region extending from the vicinity of trochanter major through at least a part of hamstrings in regio femoralis posterior.

(16) The garment according to the above item (12), further comprising a strong straining portion (E), wherein the portion (E) covers a region extending from an upper part of regio femoralis medialis through musculus vastus medialis to patella so as to support musculus vastus medialis, and further from patella through the vicinity of musculus gastrocnemius and/or musculus soleus in regio cruris medialis to the vicinity of an upper part of malleolus medialis so as to support musculus gastrocnemius and musculus soleus.

(17) The garment according to any one of the above items (1) to (16), wherein a strong straining portion is formed by laminating a cloth on the front side or back side of a main body fabric of the garment.

(18) The garment according to any one of the above items (1) to (16), wherein a strong straining portion is formed by changing a stitch for knitting a main body fabric of the garment to form a weak straining portion and a strong straining portion in patterns.

(19) The garment according to any one of the above items (1) to (16), wherein a strong straining portion is formed by laminating a film of a synthetic resin or rubber having elasticity on a predetermined part of a main body fabric of the garment or by impregnating or coating a predetermined part of a main body fabric of the garment with a solution or emulsion of a synthetic resin or rubber having elasticity followed by drying.

(20) The garment according to any one of the above items (1) to (19), wherein a strong straining portion has a straining force of 150 to 400 gf.

(21) The garment according to any one of the above items (1) to (20), wherein the stretch fabric is a knitted fabric selected from a two-way stretch tricot and a stretch raschel.

(22) The garment according to any one of the above items (1) to (21), wherein:

the garment comprises a stretch fabric, the garment covers at least a part of the lower body of a wearer, has a crotch part, and is worn by being fitted to the wearer's body, and the garment is selected from a girdle, spats, sports tights, bodysuit, leotard and swimsuit.

(23) The garment according to any one of the above items (1) to (22), wherein:

the garment comprises a stretch fabric, the garment covers at least a part of the lower body of a wearer, has a crotch part, and is worn by being fitted to the wearer's body, and the garment has a leg part cylindrically covering regio femoralis of the wearer's body to at least a position lower than the crotch part.

(24) The garment according to any one of the above items (1) to (22), wherein:

the garment comprises a stretch fabric, the garment covers at least a part of the lower body of a wearer, has a crotch part, and is worn by being fitted to the wearer's body, the position of a lower end of the garment is approximately the same as or higher than the position of the crotch part; and the garment does not have a leg part cylindrically covering regio femoralis to at least a position lower than the crotch part.

The above, and other objects, features and advantages of the present invention will become apparent from the following description read in conjunction with the accompanying drawings, in which like reference numerals designate the same elements.

DETAILED DISCLOSURE OF THE INVENTION

Hereinafter, embodiments of the present invention are described with reference to the drawings. In the present invention, the names of parts of the body and parts corresponding to muscles and bones are used in some parts of the description for the positions on the garment where the portions with strong straining forces are arranged, that is, in which parts of the garment main body of the present invention the portions with strong straining forces are arranged. Thus, to make it easy to understand, first, the positions of the bones and muscles in a human body used to describe the positions of the portions with strong straining forces, etc. in the present invention are explained.

Figure 70:
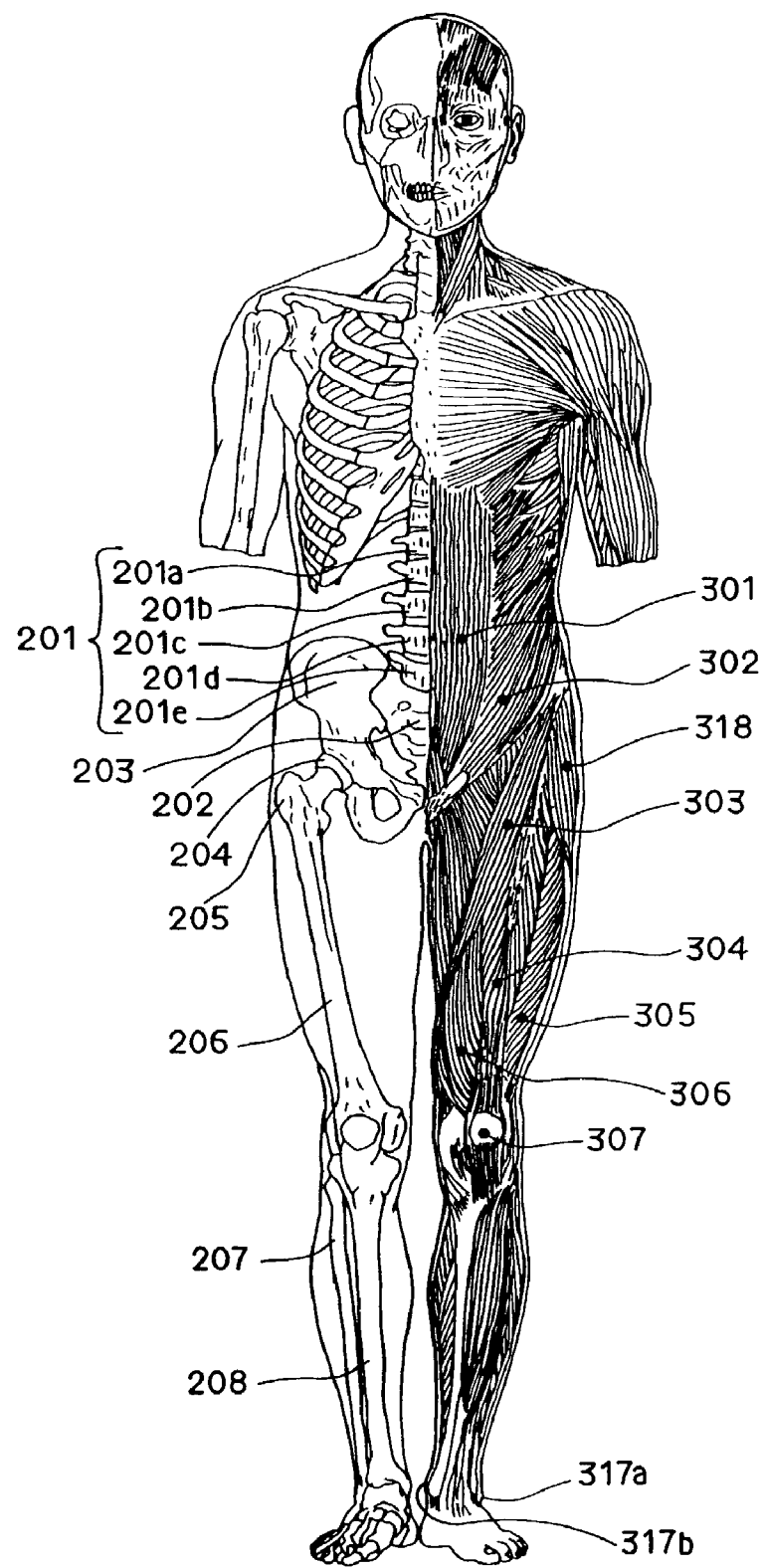
FIG. 70 is a drawing of bones and muscles in anterior human body.
Figure 71:
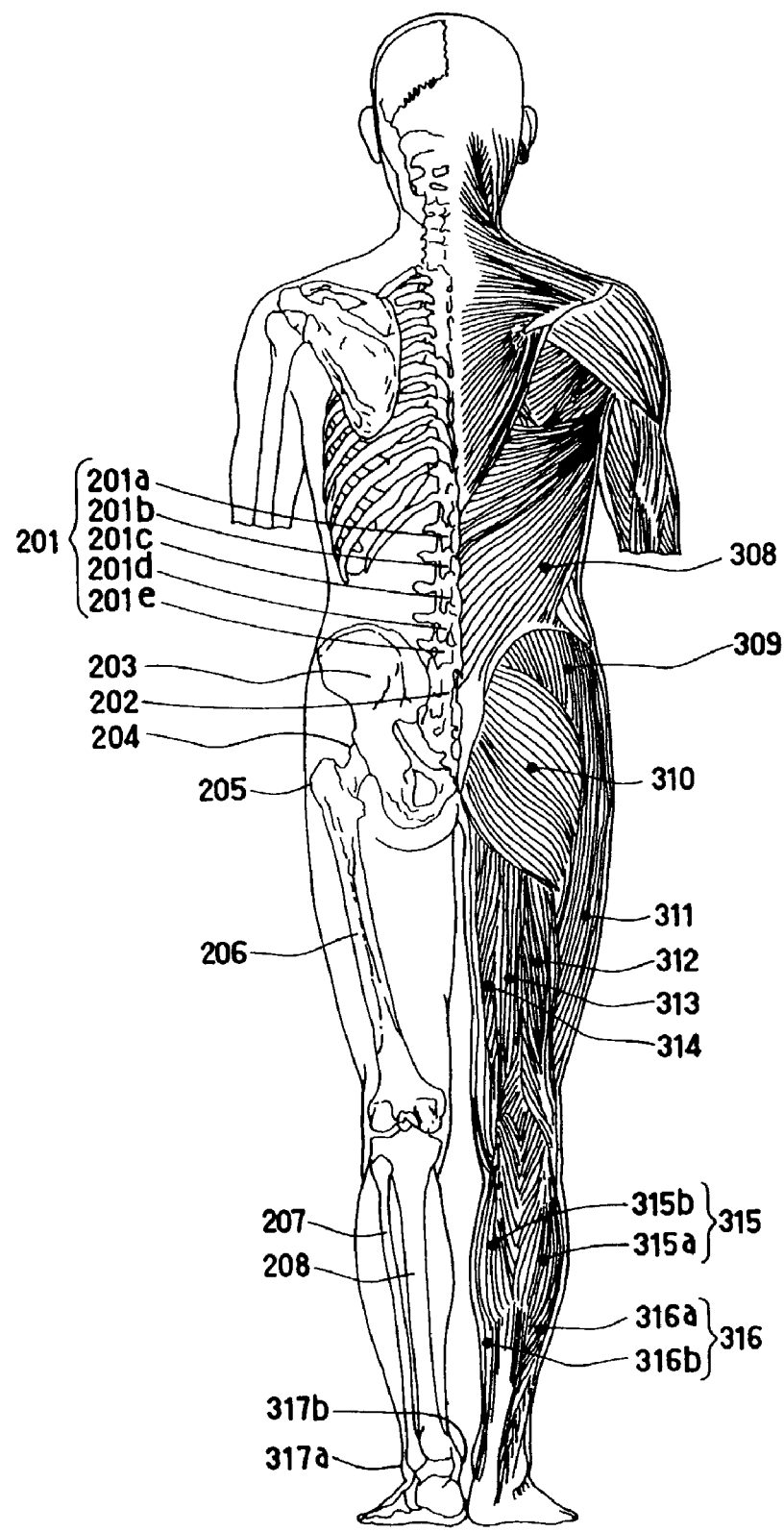
FIG. 71 is a drawing of bones and muscles in posterior human body.

FIG. 70 illustrates bones in anterior human body in its left half, and muscles in anterior human body in its right half. FIG. 71 illustrates bones in posterior human body in its left half, and muscles in posterior human body in its right half. In FIGS. 70 and 71, illustration and description are omitted partially for the muscles and bones in the regions not particularly necessary to describe the present invention.

In FIGS. 70 and 71, numeral 201 indicates vertebrae lumbalis; 201a indicates first vertebra lumbalis; 201b indicates second vertebra lumbalis; 201c indicates third vertebra lumbalis; 201d indicates fourth vertebra lumbalis; and 201e indicates fifth vertebra lumbalis. Further, numeral 202 indicates os sacrum; 203 indicates pelvis (os ilium); 204 indicates caput ossis femoris; 205 indicates trochanter major; 206 indicates corpus ossis femoris; 207 indicates fibula; 208 indicates tibia; 301 indicates musculus rectus abdominis; 302 indicates musculus obliquus externus abdominis; 303 indicates musculus sartorius; 304 indicates musculus rectus femoris; 305 indicates musculus vastus lateralis; 306 indicates musculus vastus medialis; 307 indicates the position of patella; 308 indicates musculus latissimus dorsi; 309 indicates musculus gluteus medius; 310 indicates musculus gluteus maximus; 311 indicates tractus iliotibialis; 312 indicates musculus biceps femoris; 313 indicates musculus semitendinosus; 314 indicates musculus semimembranosus; 315 indicates musculus gastrocnemius; 315a indicates musculus gastrocnemius in regio cruris lateralis; 315b indicates musculus gastrocnemius in regio cruris medialis; 316 indicates musculus soleus; 316a indicates musculus soleus in regio cruris lateralis; 316b indicates musculus soleus in regio cruris medialis; 317a indicates malleolus lateralis; 317b indicates malleolus medialis; and 318 indicates musculus tensor faciae latae. The direction of the muscle fibers of each muscle is indicated by the length direction of the thin lines shown in each muscle in the drawings. The direction of muscle fibers indicates the direction of muscle contraction. Although not shown in FIGS. 70 and 71, musculus obliquus internus abdominis exists approximately on the back sides of musculus rectus abdominis and musculus obliquus externus abdominis, and the direction of its muscle fibers is approximately obliquely downward from the center front to the right and left of a human body. Because the positions, shapes and sizes of these bones and muscles are slightly different depending on individuals, the above-described drawings of muscles and bones are shown as one representative example.

In the present invention, the term "in the vicinity of . . . " is used in the description of the positions on the garment where portions with strong straining forces are arranged. This means that the positions may deviate more or less from predetermined and specified positions as long as the object of the present invention is achieved. As described above, the positions, shapes and sizes of bones and muscles are different depending on individuals, and the size of the entire human body also is different. Therefore, the positions on the garment where portions with strong straining forces are arranged may deviate more or less from predetermined and specified positions as long as the object of the present invention is achieved.

In the present invention, unless specified otherwise, a strong straining portion has a main stretch direction approximately in the longitudinal direction. The phrase "approximately in the longitudinal direction" is used because when the strong straining portion is formed of a fabric and has a curved shape, it is difficult to obtain a fabric having a main stretch direction in the longitudinal direction in every region. Furthermore, in a strong straining portion, "has a main stretch direction approximately in the longitudinal direction" means that when it is also stretchable in the direction perpendicular to the longitudinal direction, its stretchability in the direction perpendicular to the longitudinal direction is the same or lower than its stretchability in the longitudinal direction. It also includes the case in which the strong straining portion does not have stretchability in the direction perpendicular to the longitudinal direction. In a strong straining portion, it is preferable that the stretchability in the longitudinal direction is higher than the stretchability in the direction perpendicular to the longitudinal direction.

In the present invention, "connected" in the phrase "right and left parts are connected at . . . " includes the state in which right and left parts are continuous without a seam, and also the state in which right and left parts are connected by sewing, bonding, etc.

Figure 1:
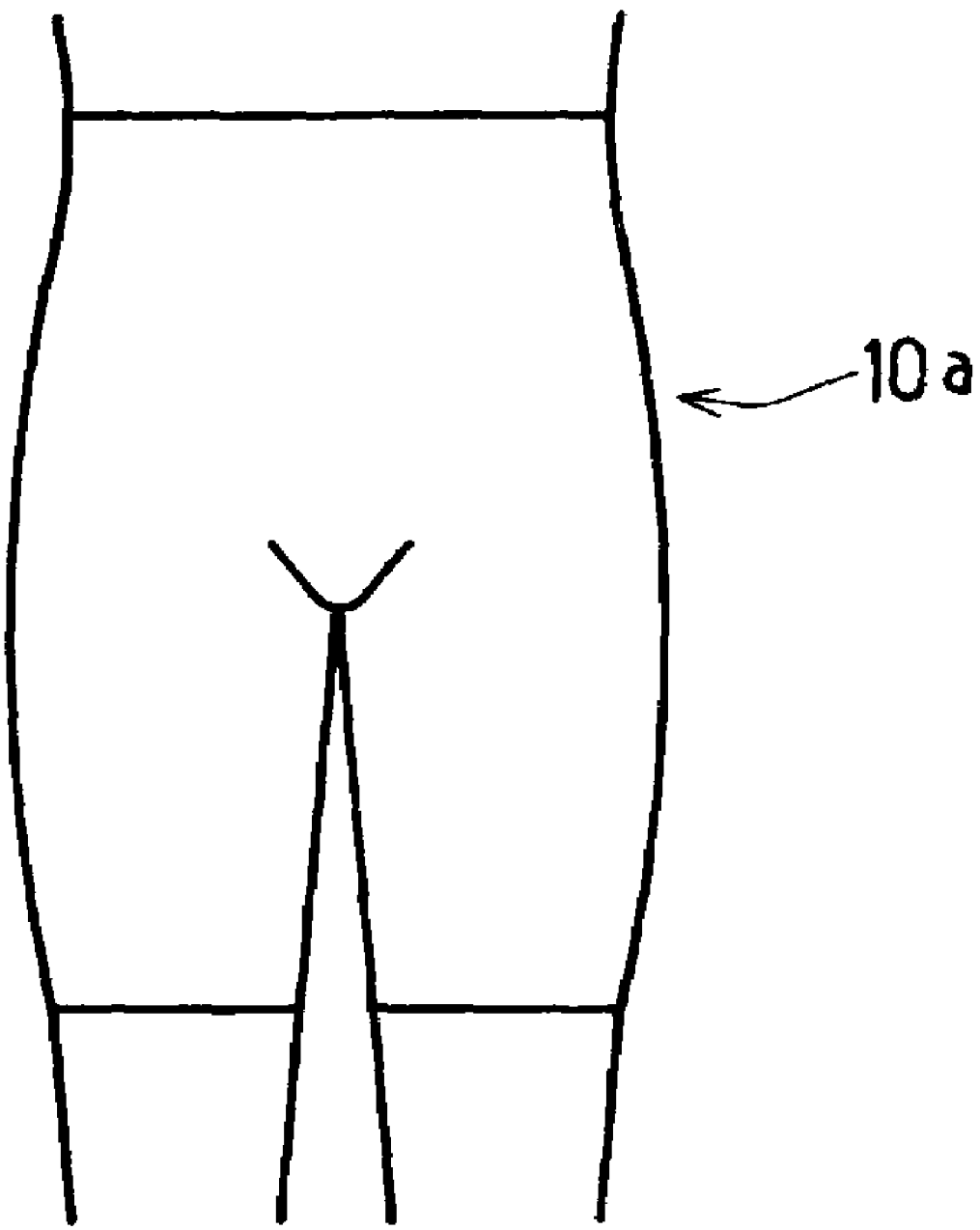
FIG. 1 is a front view of a long type girdle as a garment of the present invention in wearing condition.
Figure 2:
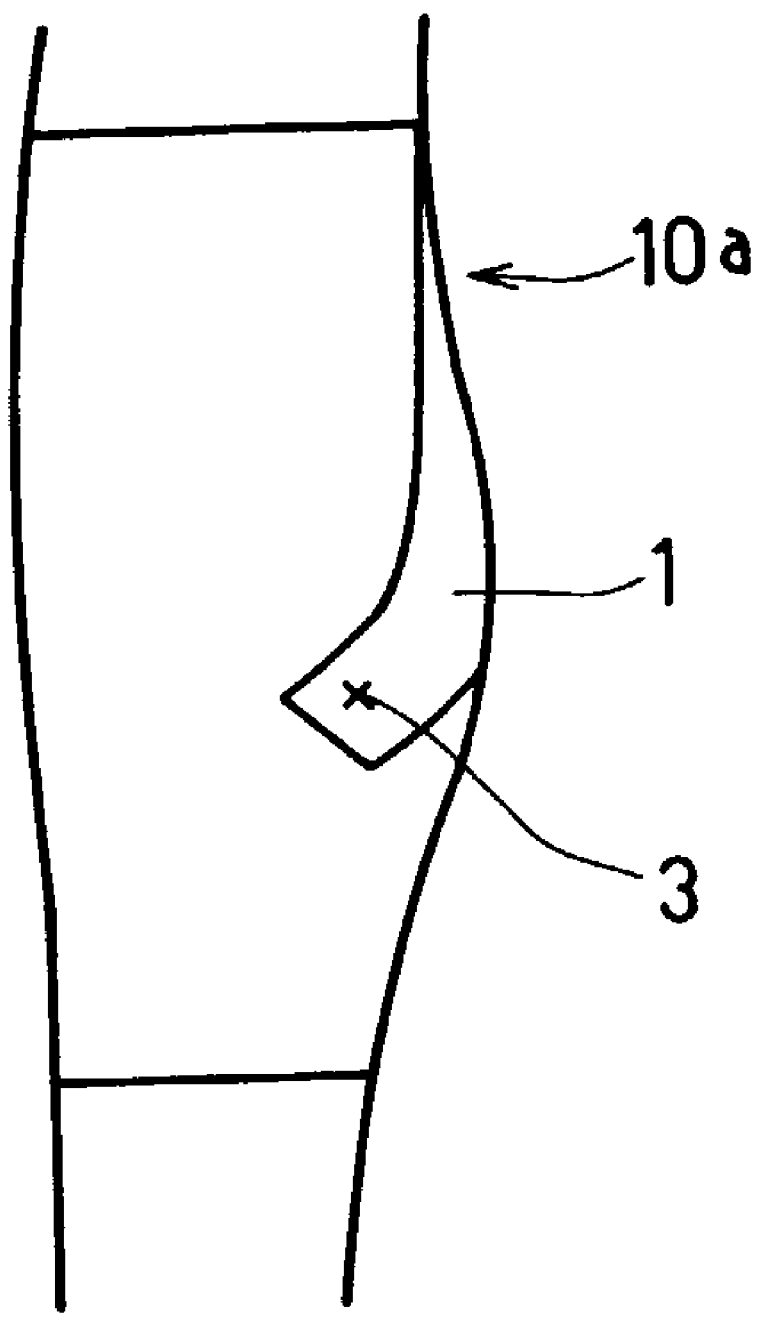
FIG. 2 is a left side view of the long type girdle of FIG. 1 in wearing condition.
Figure 3:
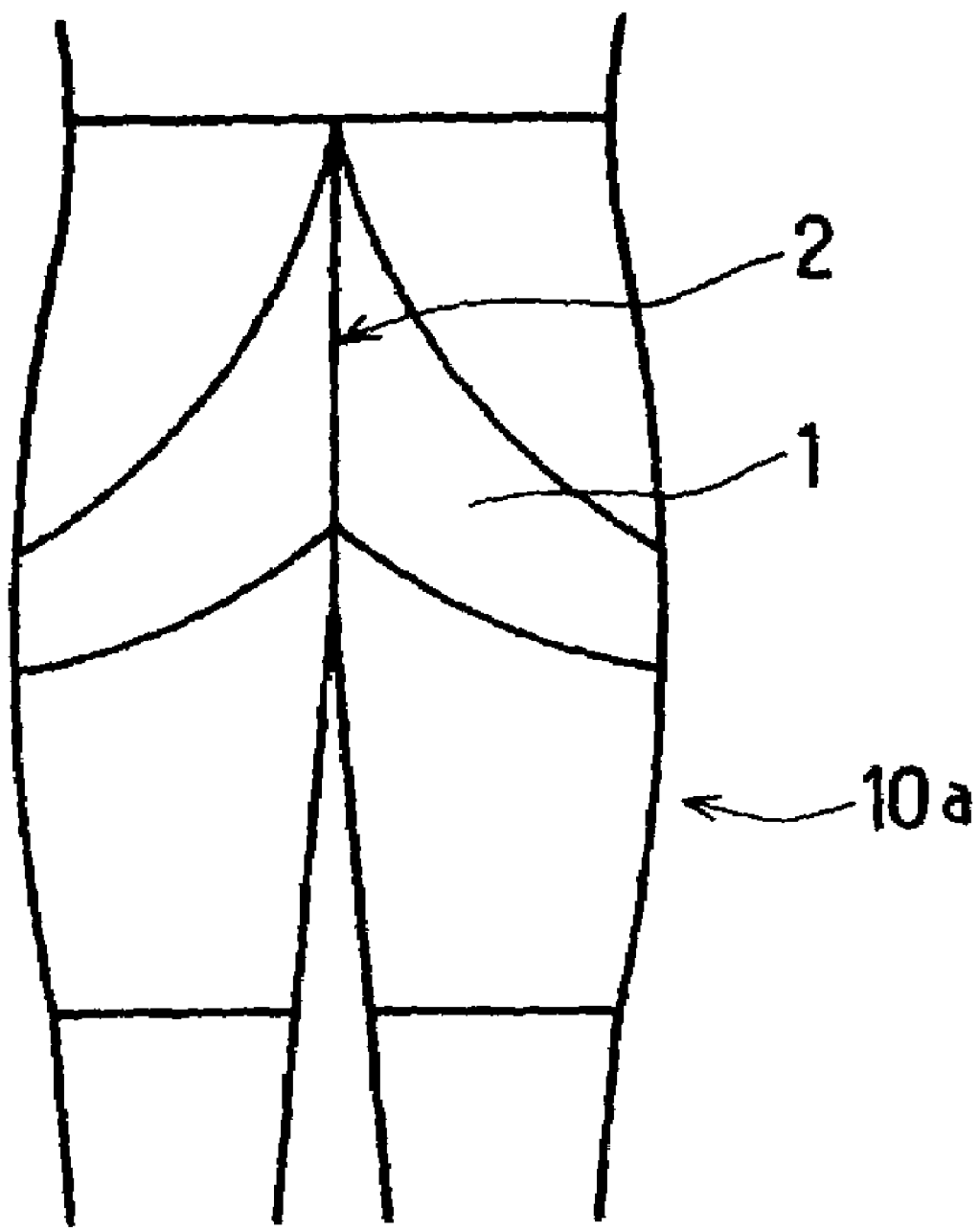
FIG. 3 is a rear view of the long type girdle of FIG. 1 in wearing condition.

FIGS. 1 to 3 show a front view, a left side view and a rear view of a long type girdle as a garment of the present invention in wearing condition, respectively. The long type girdle 10a shown in FIGS. 1 to 3 has, as a strong straining portion (A), a strong straining portion 1 in which right and left parts are connected at a position 2 on the back side of the girdle corresponding to from the fourth vertebra lumbalis to os sacrum of the wearer's body and which covers a region extending from the position 2 through the tops of the bulges of the buttocks or vicinities thereof in an approximately middle part of musculus gluteus maximus at right and left approximately in the direction of muscle fibers of musculus gluteus maximus to at least the vicinity of trochanter major 3. Other parts of the main body of this girdle 10a comprise a stretch fabric having a lower straining force than that of the strong straining portion. The strong straining portion 1 passes through the tops of the bulges of the buttocks or vicinities thereof in the direction of the muscle fibers of musculus gluteus maximus. In addition, the right and left parts of the strong straining portion 1 are connected at the position 2 on the back side of the girdle corresponding to from the fourth vertebra lumbalis to os sacrum of the wearer's body. Thus, musculus gluteus maximus can be supported firmly in the direction of its muscle fibers. Therefore, rotating motion of the hips is supported, and a decrease in the rotating angle of the hips is prevented. Accordingly, it can play a large role in stabilizing the pelvis in anterior-posterior direction, and for an elderly person is effective in preventing falling down. It also can play a large role in extending the hip joint in anterior-posterior direction when running, jumping, and climbing up a slope. Furthermore, because the strong straining portion covers the vicinity of trochanter major, a garment having the functions of improving the joint between caput ossis femoris 204 and acetabulum and increasing the stability of the hip joint can be provided.

Figure 4:
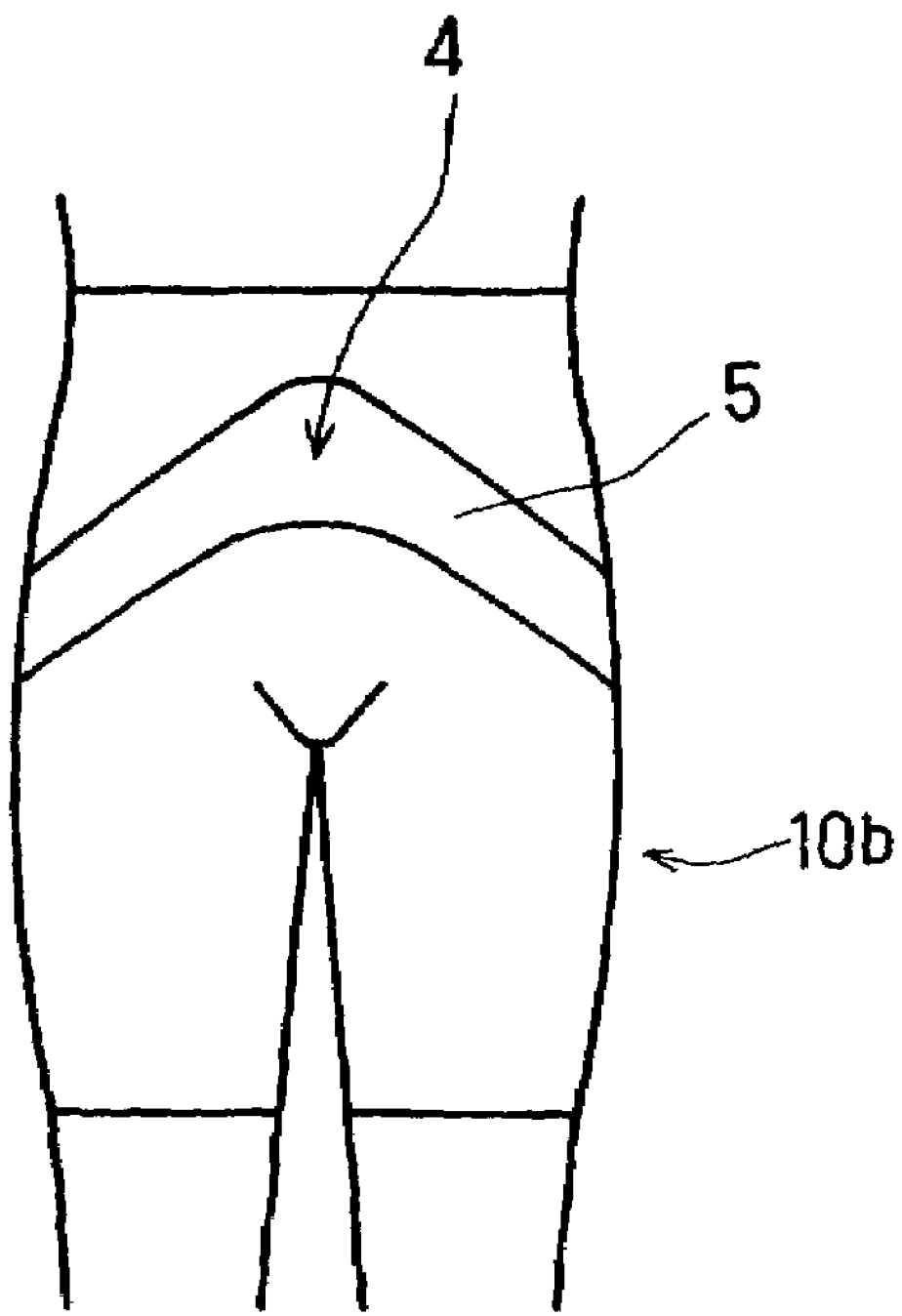
FIG. 4 is a front view of another embodiment of a long type girdle as a garment of the present invention in wearing condition.
Figure 5:
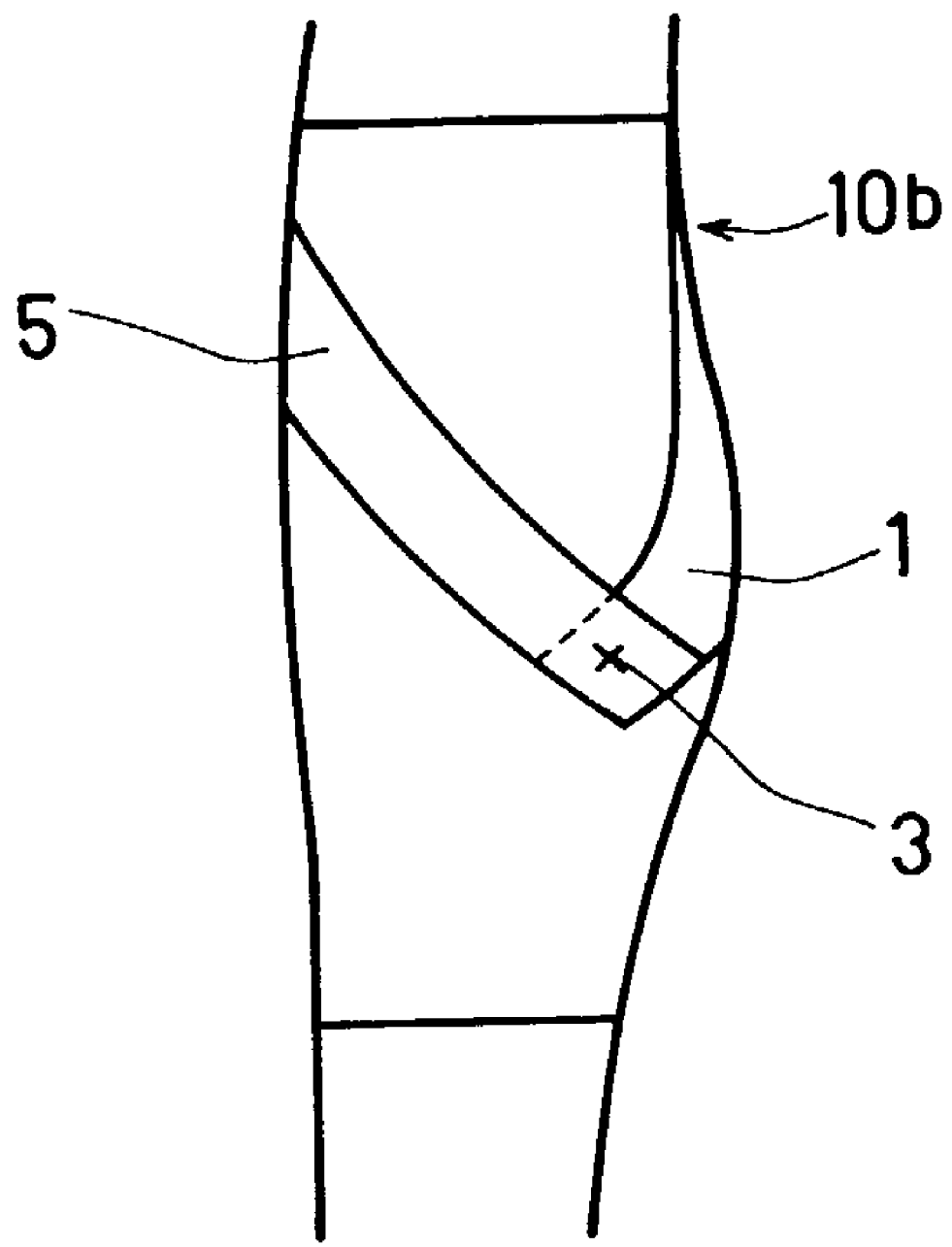
FIG. 5 is a left side view of the long type girdle of FIG. 4 in wearing condition.
Figure 6:
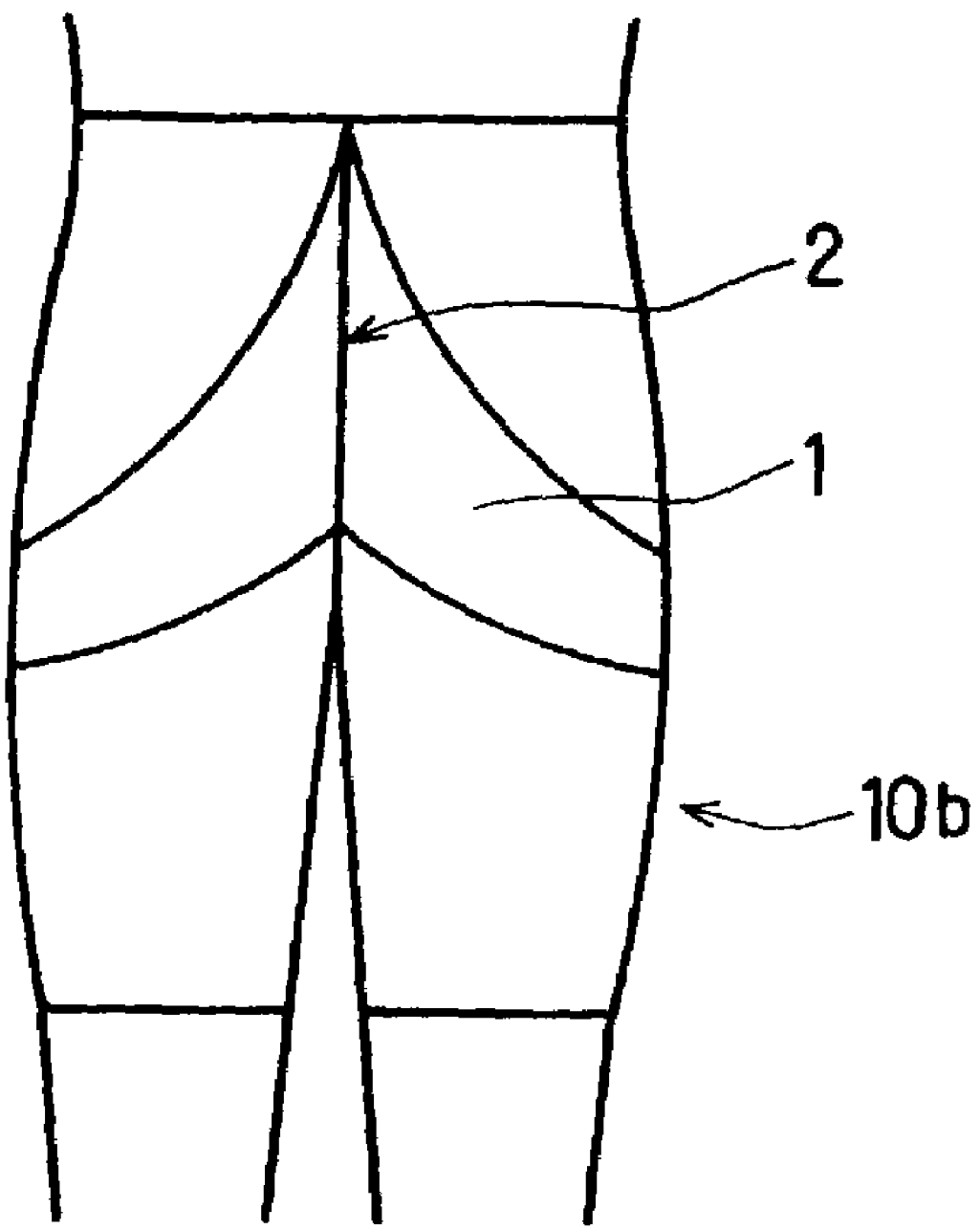
FIG. 6 is a rear view of the long type girdle of FIG. 4 in wearing condition.

FIGS. 4 to 6 show a front view, a left side view and a rear view of another embodiment of a long type girdle as a garment of the present invention in wearing condition, respectively. The long type girdle 10b shown in FIGS. 4 to 6 has, as the same strong straining portion (A), a strong straining portion 1 at the same position as that in the girdle 10a shown in FIGS. 1 to 3, and further has, as a strong straining portion (B), a strong straining portion 5 in which right and left parts are connected at a position 4 on musculus rectus abdominis in hypogastric region and which covers a region extending obliquely downward from the position 4 on musculus rectus abdominis in hypogastric region approximately in the direction of muscle fibers of musculus obliquus internus abdominis at right and left to the vicinity of trochanter major 3. Because other points are the same as those in the long type girdle shown in FIGS. 1 to 3, the same signs are applied to the same parts, and detailed descriptions are omitted.

Because the girdle shown in FIGS. 4 to 6 has the strong straining portion 1, the same effects as those of the girdle 10a shown in FIGS. 1 to 3 can be accomplished. In addition, this girdle has, as a strong straining portion (B), the strong straining portion 5 in which right and left parts are connected at the position 4 on musculus rectus abdominis in hypogastric region and which covers the region extending obliquely downward from the position 4 on musculus rectus abdominis in hypogastric region approximately in the direction of the muscle fibers of musculus obliquus internus abdominis at right and left to at least the vicinity of trochanter major 3. Therefore, a garment having the functions of supporting musculus rectus abdominis 301 in part and musculus obliquus internus abdominis, reducing lumbar lordosis, maintaining good posture, making youthful figure, and preventing generation of pains such as lumbar pains can be provided.

Figure 7:
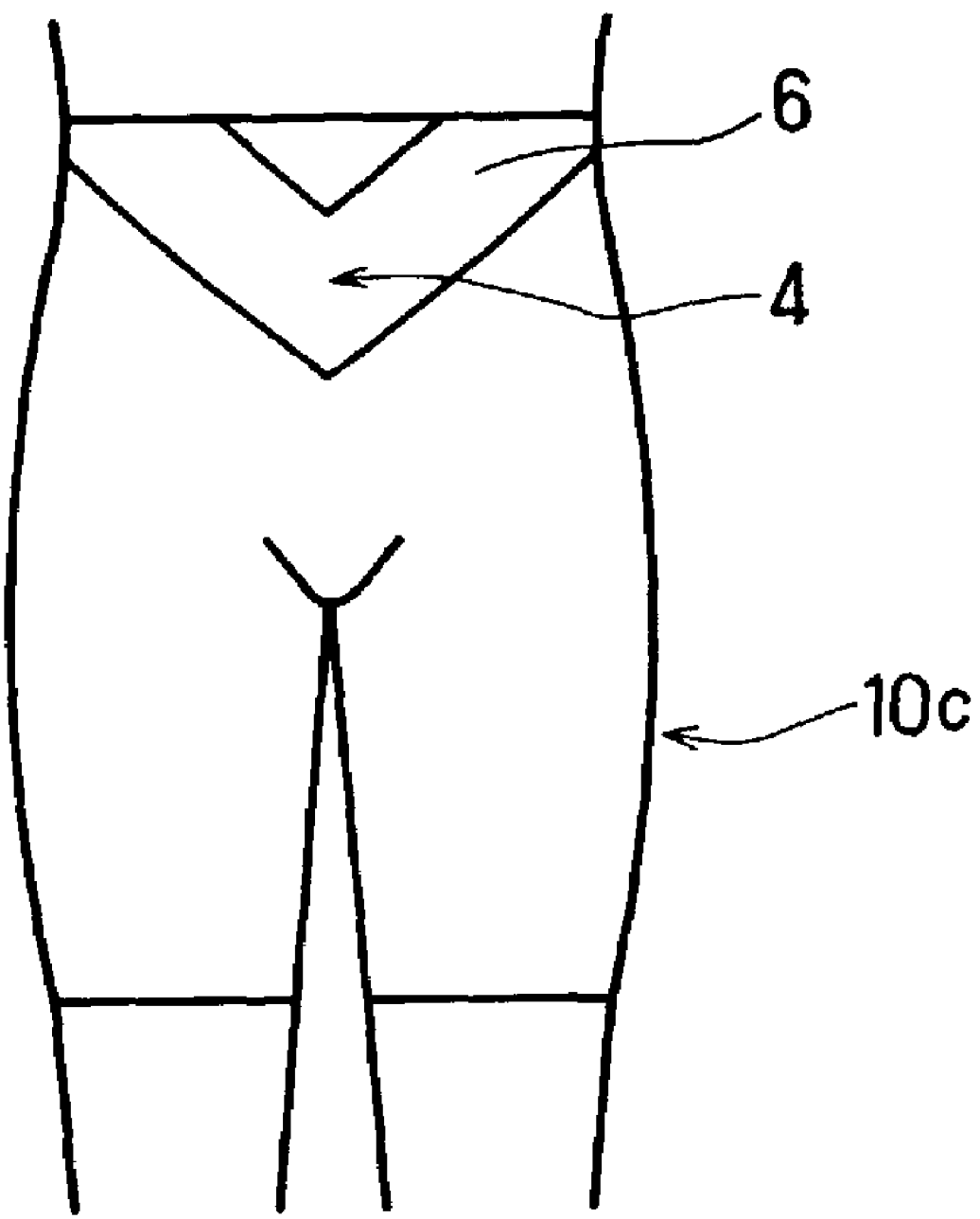
FIG. 7 is a front view of still another embodiment of a long type girdle as a garment of the present invention in wearing condition.
Figure 8:
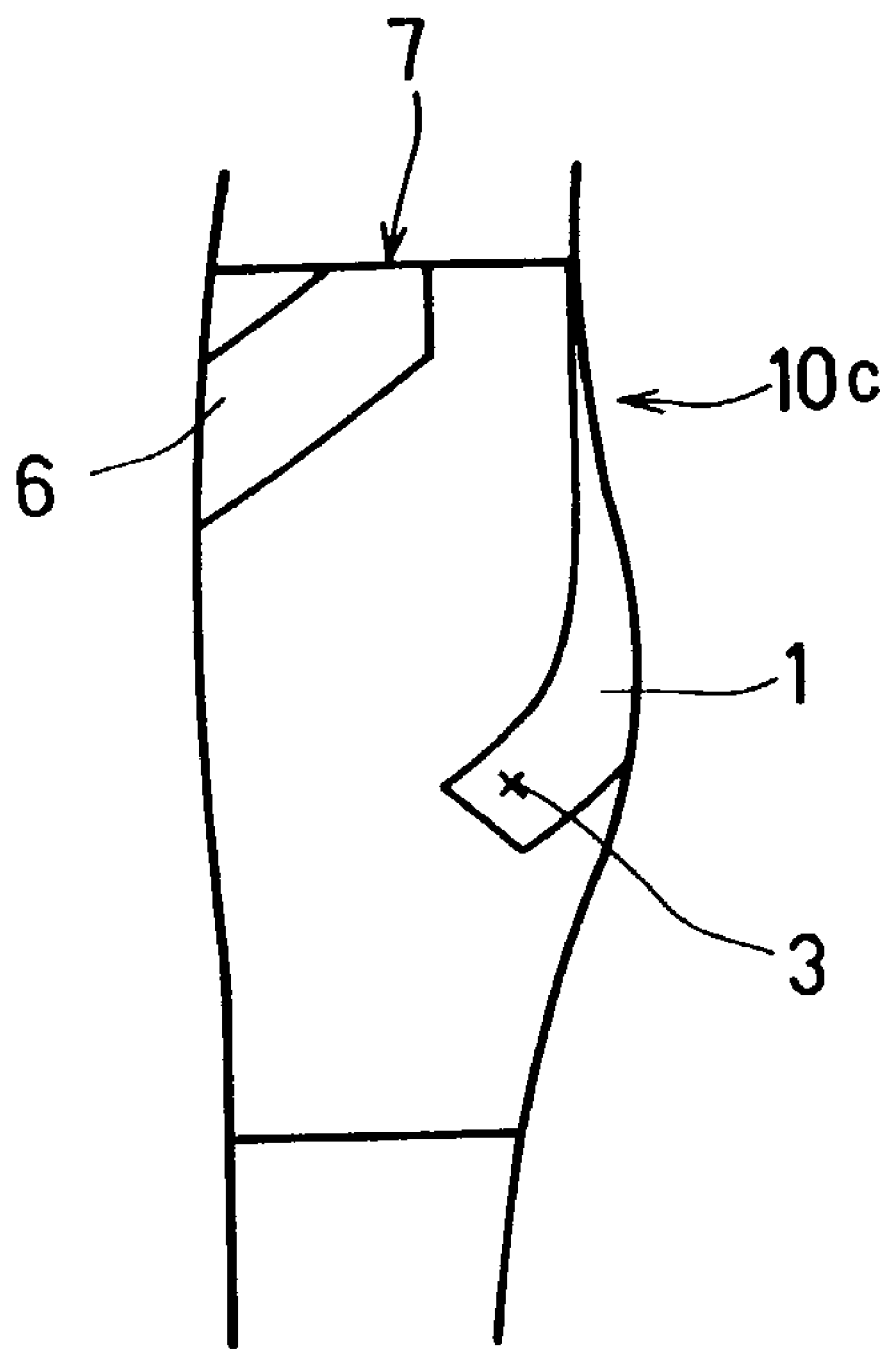
FIG. 8 is a left side view of the long type girdle of FIG. 7 in wearing condition.
Figure 9:
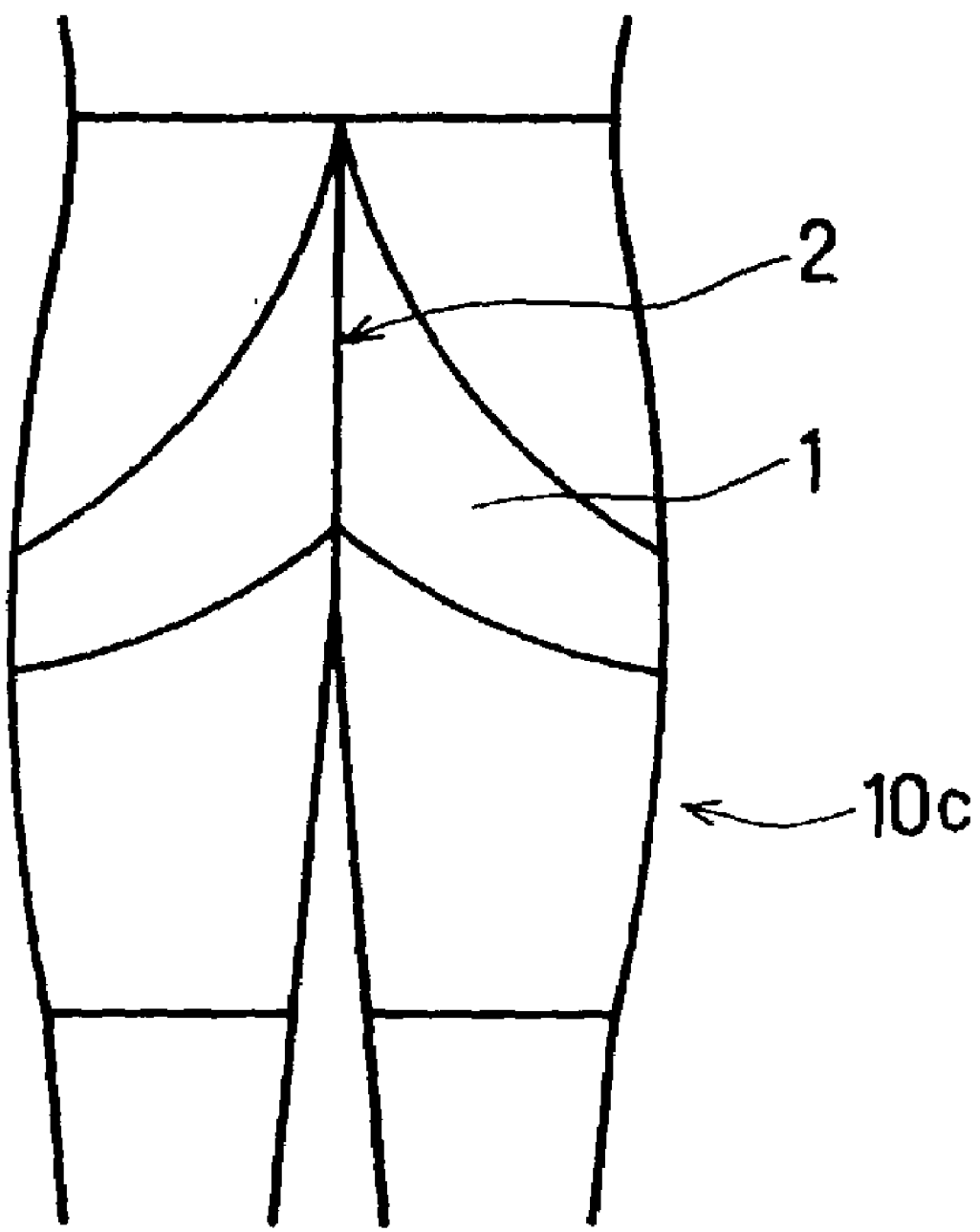
FIG. 9 is a rear view of the long type girdle of FIG. 7 in wearing condition.

Next, FIGS. 7 to 9 show a front view, a left side view and a rear view of still another embodiment of a long type girdle as a garment of the present invention in wearing condition, respectively. The long type girdle 10c shown in FIGS. 7 to 9 has, as the same strong straining portion (A), a strong straining portion 1 at the same position as that in the girdle 10a shown in FIGS. 1 to 3, and further has, as a strong straining portion (C), a strong straining portion 6 in which right and left parts are connected at a position 4 on musculus rectus abdominis in hypogastric region and which covers a region extending obliquely upward from the position 4 on musculus rectus abdominis in hypogastric region approximately in the direction of muscle fibers of musculus obliquus externus abdominis at right and left to at least a position exceeding the sides 7 of the wearer to the back side. Because other points are the same as those in the long type girdle shown in FIGS. 1 to 3, the same signs are applied to the same parts, and detailed descriptions are omitted.

Because the girdle shown in FIGS. 7 to 9 has the strong straining portion 1, the same effects as those of the girdle 10a shown in FIGS. 1 to 3 can be accomplished. In addition, this girdle has, as a strong straining portion (C), the strong straining portion 6 in which right and left parts are connected at the position 4 on musculus rectus abdominis in hypogastric region and which covers the region extending obliquely upward from the position 4 on musculus rectus abdominis in hypogastric region approximately in the direction of muscle fibers of musculus obliquus externus abdominis at right and left to at least a position exceeding the sides 7 of the wearer to the back side. Therefore, a garment having the functions of supporting musculus rectus abdominis 301 in part and musculus obliquus externus abdominis 302, reducing lumbar lordosis, maintaining good posture, making youthful figure, and preventing generation of pains such as lumbar pains can be provided.

Figure 10:
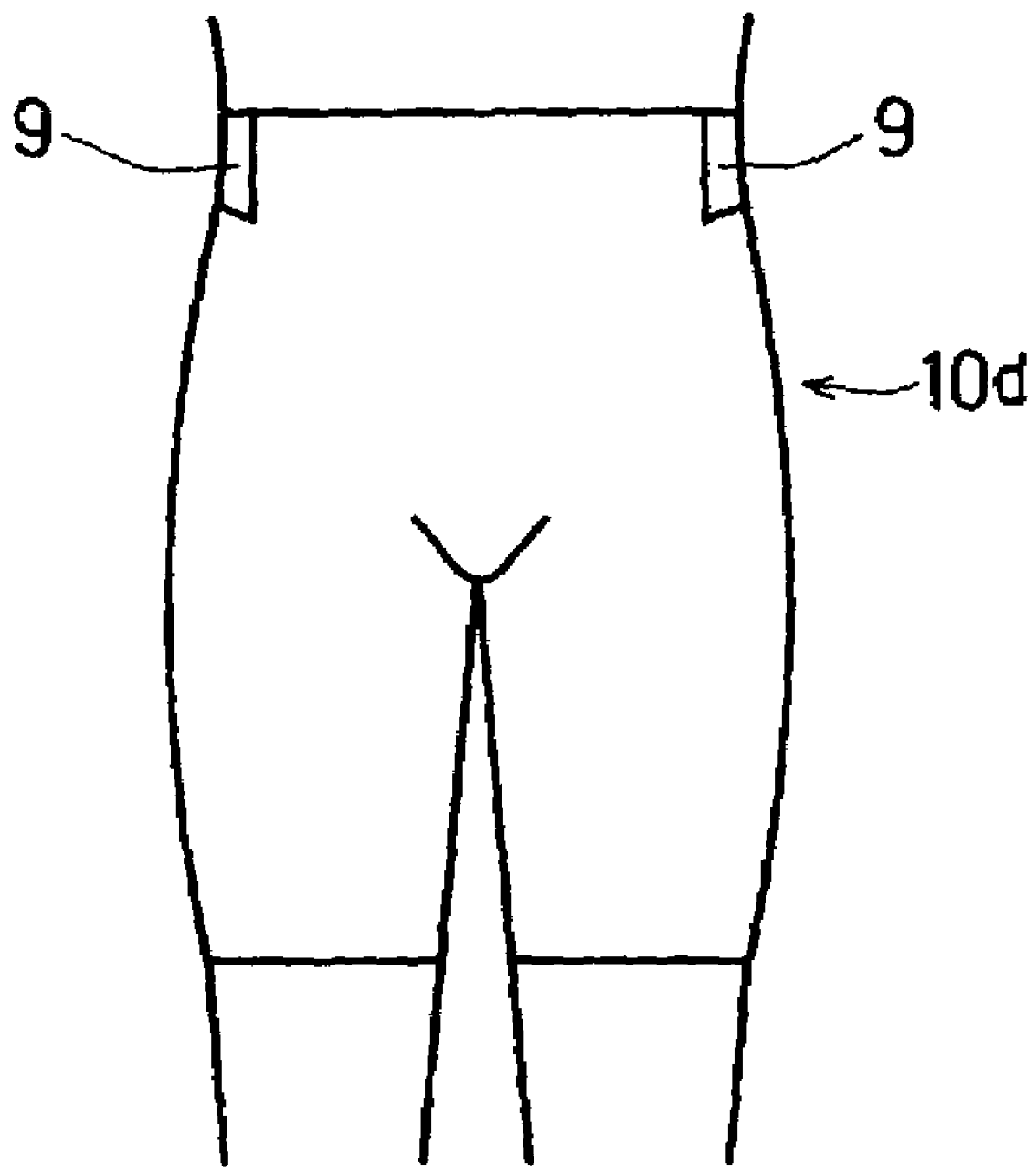
FIG. 10 is a front view of still another embodiment of a long type girdle as a garment of the present invention in wearing condition.
Figure 11:
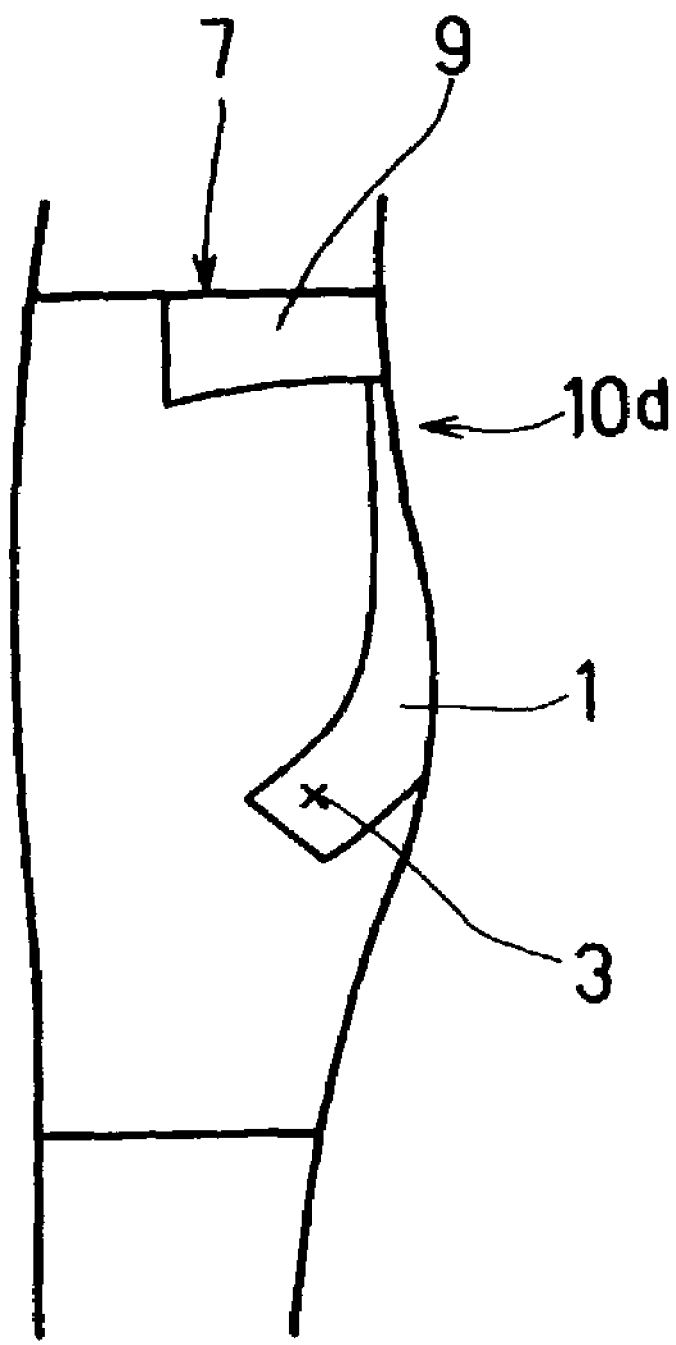
FIG. 11 is a left side view of the long type girdle of FIG. 10 in wearing condition.
Figure 12:
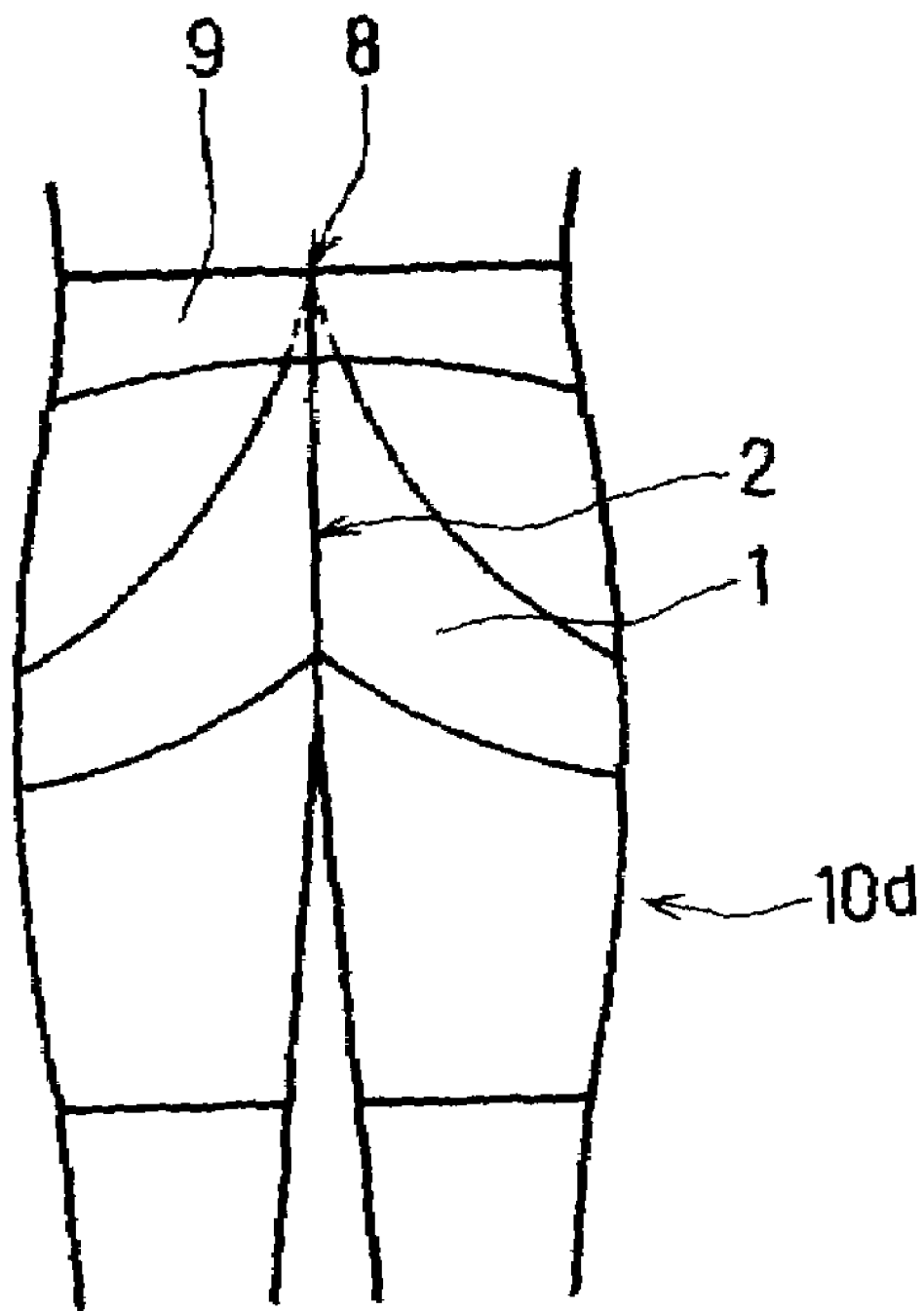
FIG. 12 is a rear view of the long type girdle of FIG. 10 in wearing condition.

Next, FIGS. 10 to 12 show a front view, a left side view and a rear view of still another embodiment of a long type girdle as a garment of the present invention in wearing condition, respectively. The long type girdle 10d shown in FIGS. 10 to 12 has, as the same strong straining portion (A), a strong straining portion 1 at the same position as in the girdle 10a shown in FIGS. 1 to 3, and further has, as a strong straining portion (D), a strong straining portion 9 in which right and left parts are connected approximately in the vicinity of a position 8 at the back center of the waist and which covers a region extending from the vicinity of the position 8 at the back center of the waist through musculus latissimus dorsi and musculus gluteus medius at right and left and a part of musculus obliquus externus abdominis to at least a position exceeding the sides 7 of the wearer to the front side. Because other points are the same as those in the long type girdle shown in FIGS. 1 to 3, the same signs are applied to the same parts, and detailed descriptions are omitted.

Because the girdle shown in FIGS. 10 to 12 has the strong straining portion 1, the same effects as those of the girdle 10a shown in FIGS. 1 to 3 can be accomplished. Furthermore, this girdle has, as a strong straining portion (D), the strong straining portion 9 in which right and left parts are connected approximately in the vicinity of the position 8 at the back center of the waist and which covers a region extending from the vicinity of the position 8 at the back center of the waist through musculus latissimus dorsi 308 and musculus gluteus medius 309 at right and left and a part of musculus obliquus externus abdominis 302 to at least a position exceeding the sides 7 of the wearer to the front side. Therefore, the functions of preventing backward inclination of the pelvis and assisting to maintain a stable position of the pelvis can be displayed.

Figure 13:
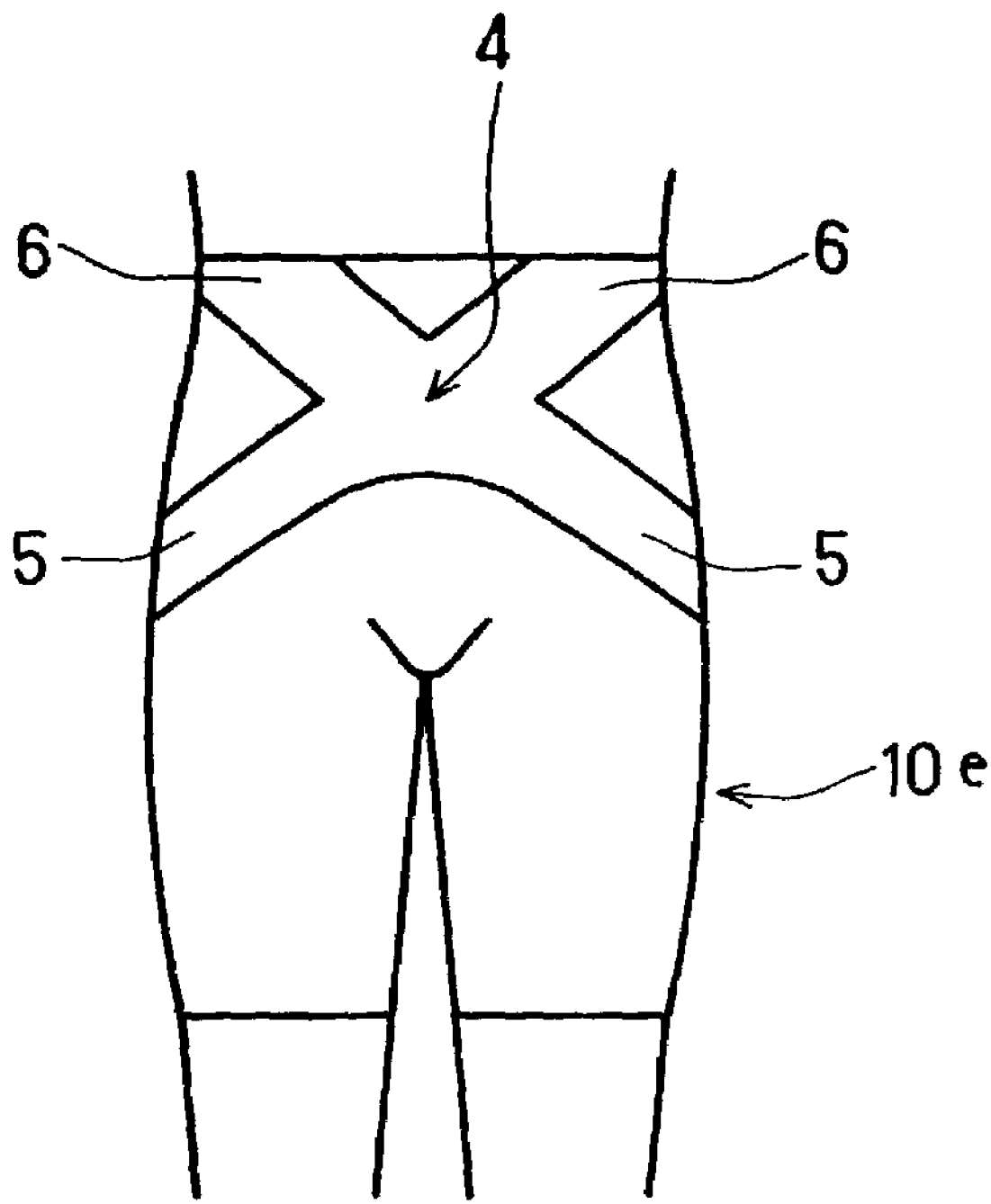
FIG. 13 is a front view of still another embodiment of a long type girdle as a garment of the present invention in wearing condition.
Figure 14:
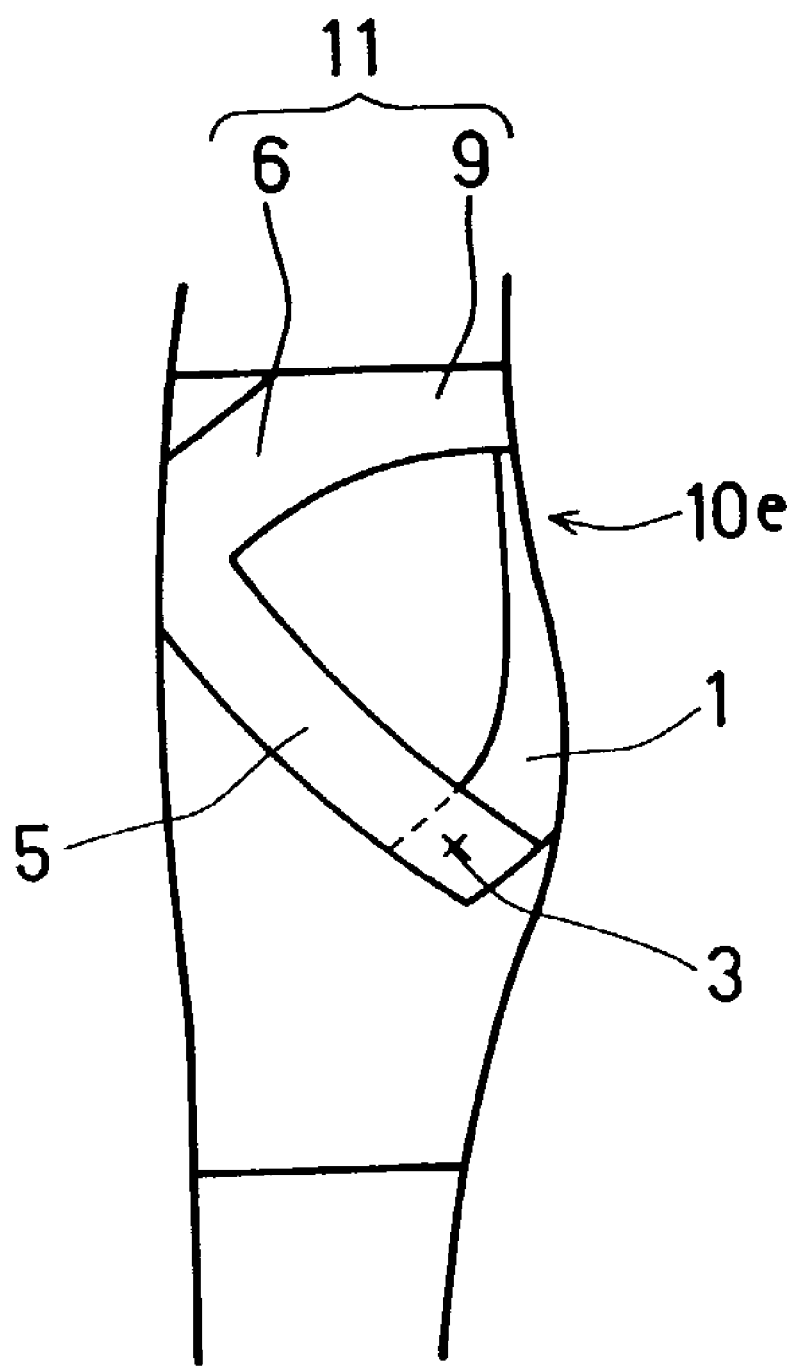
FIG. 14 is a left side view of the long type girdle of FIG. 13 in wearing condition.
Figure 15:
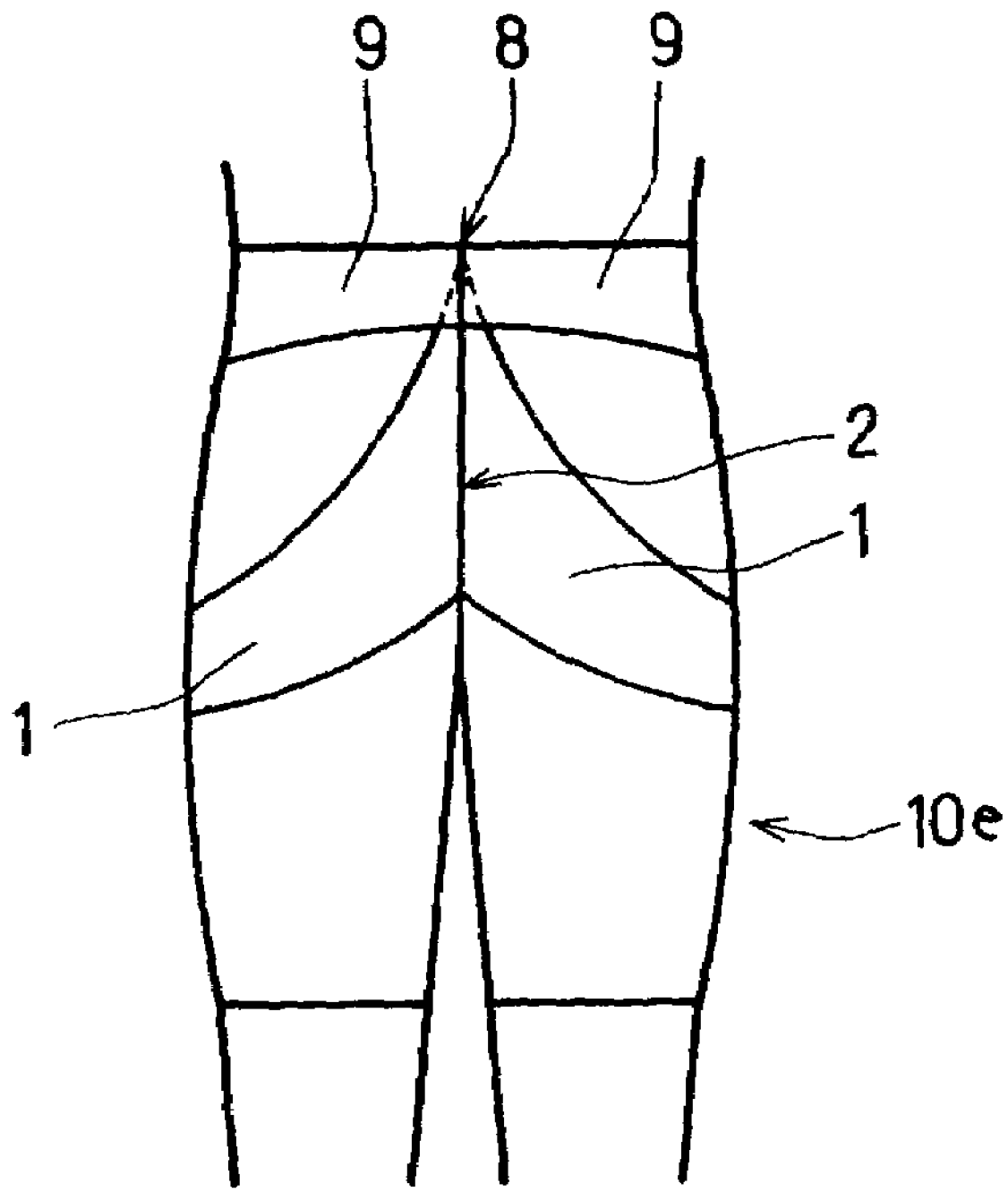
FIG. 15 is a rear view of the long type girdle of FIG. 13 in wearing condition.

Next, FIGS. 13 to 15 show a front view, a left side view and a rear view of still another embodiment of a long type girdle as a garment of the present invention in wearing condition, respectively. The long type girdle 10e shown in FIGS. 13 to 15 has a strong straining portion 1 as the same strong straining portion (A) at the same position as in the girdle 10a shown in FIGS. 1 to 3; a strong straining portion 5 as the same strong straining portion (B) at the same position as in the girdle 10b shown in FIGS. 4 to 6; a strong straining portion 6 as the same strong straining portion (C) at the same position as in the long type girdle 10c shown in FIGS. 7 to 9; and a strong straining portion 9 as the same strong straining portion (D) at the same position as in the long type girdle 10d shown in FIGS. 10 to 12. In this example, the strong straining portions 5 and 6 are united at the position 4 on musculus rectus abdominis in hypogastric region. The strong straining portions 6 and 9 are united to form a strong straining portion 11. Thus, with the strong straining portions 1, 5, 6 and 9, a girdle having the same effects in combination as those described for respective girdles 10a, 10b, 10c and 10d shown in FIGS. 1 to 12 can be obtained. Also, because the strong straining portions 5 and 6 are united, the functions of supporting abdominal muscles more strongly, reducing lumbar lordosis, maintaining good posture, making youthful figure, and preventing generation of pains such as lumbar pains are displayed more easily. Furthermore, because the strong straining portions 6 and 9 are united to form the strong straining portion 11, the functions of strongly supporting the region from the vicinity of the position 8 at the back center of the waist through musculus latissimus dorsi 308 and musculus gluteus medius 309 at right and left and musculus obliquus externus abdominis 302, preventing backward inclination of the pelvis, and maintaining a stable position of the pelvis are displayed more easily.

Figure 16:
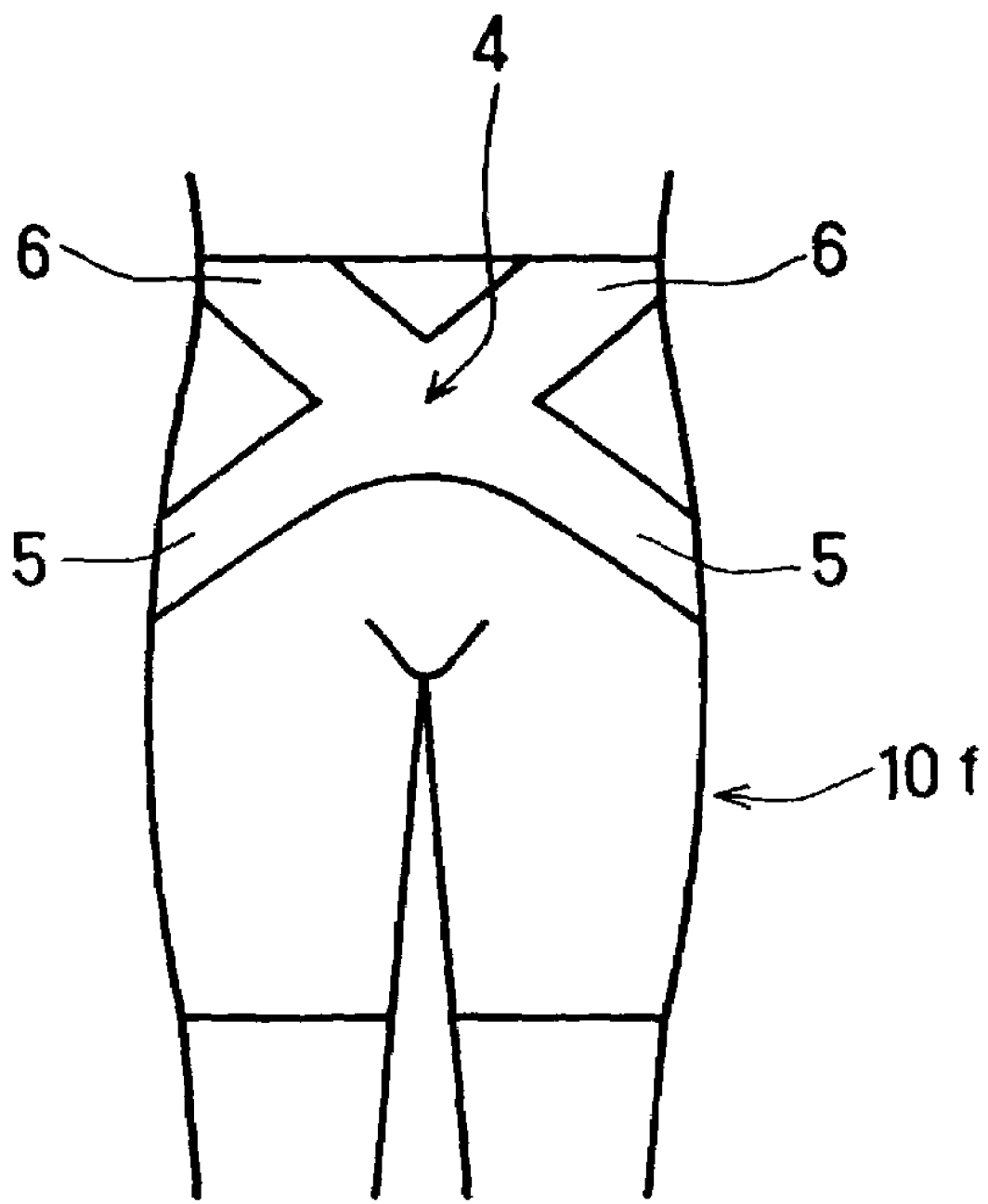
FIG. 16 is a front view of still another embodiment of a long type girdle as a garment of the present invention in wearing condition.
Figure 17:
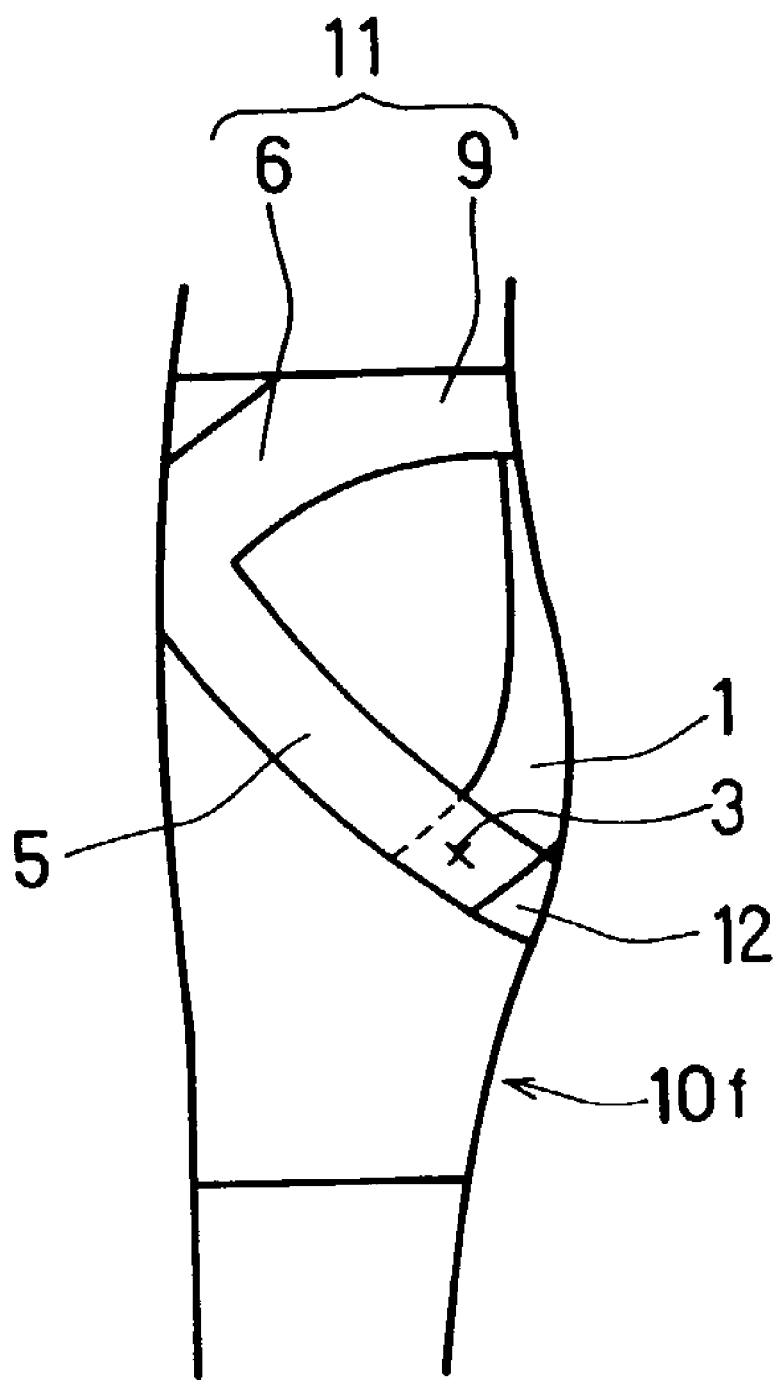
FIG. 17 is a left side view of the long type girdle of FIG. 16 in wearing condition.
Figure 18:
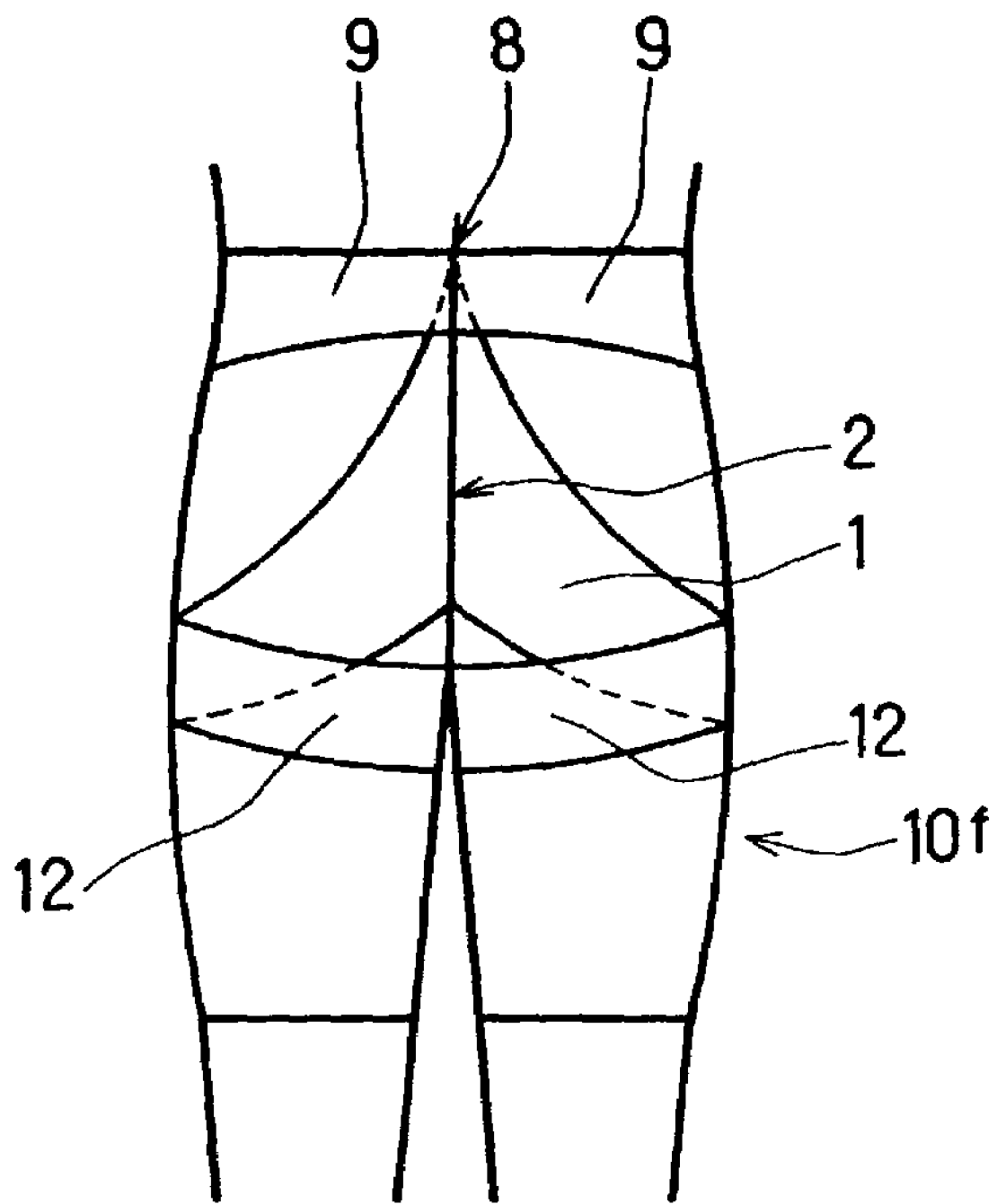
FIG. 18 is a rear view of the long type girdle of FIG. 16 in wearing condition.

Next, FIGS. 16 to 18 show a front view, a left side view and a rear view of still another embodiment of a long type girdle as a garment of the present invention in wearing condition, respectively. Compared with the girdle 10e shown in FIGS. 13 to 15, in the long type girdle 10f shown in FIGS. 16 to 18, the portion indicated by the strong straining portion 5 extends further from the vicinity of trochanter major 3 through a lower part of the bulges of the buttocks. Indicating this extended part of the strong straining portion with numeral 12, the strong straining portions 5 and 12 are united to form a strong straining portion (B2). Therefore, while this girdle can display the same excellent functions as those of the girdle 10e shown in FIGS. 13 to 15, because it has the strong straining portion (B2), the function of pressing trochanter major 3 is enhanced further, and the functions of improving the joint between caput ossis femoris 204 and acetabulum and increasing the stability of the hip joint are enhanced further. Furthermore, with the strong straining portion 12, the function of keeping the bulges of the hips in a high position can be provided.

Figure 19:
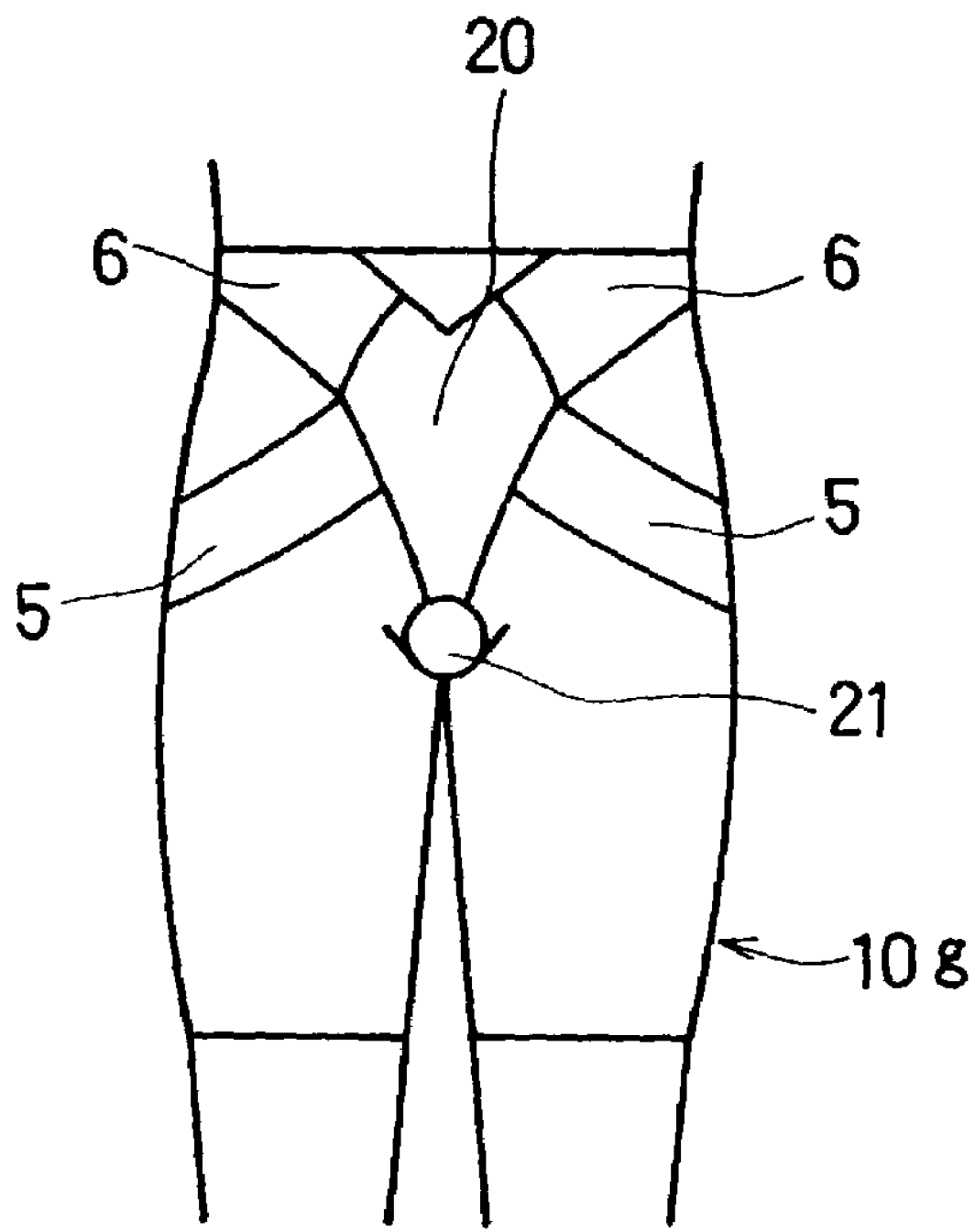
FIG. 19 is a front view of still another embodiment of a long type girdle as a garment of the present invention in wearing condition.
Figure 20:
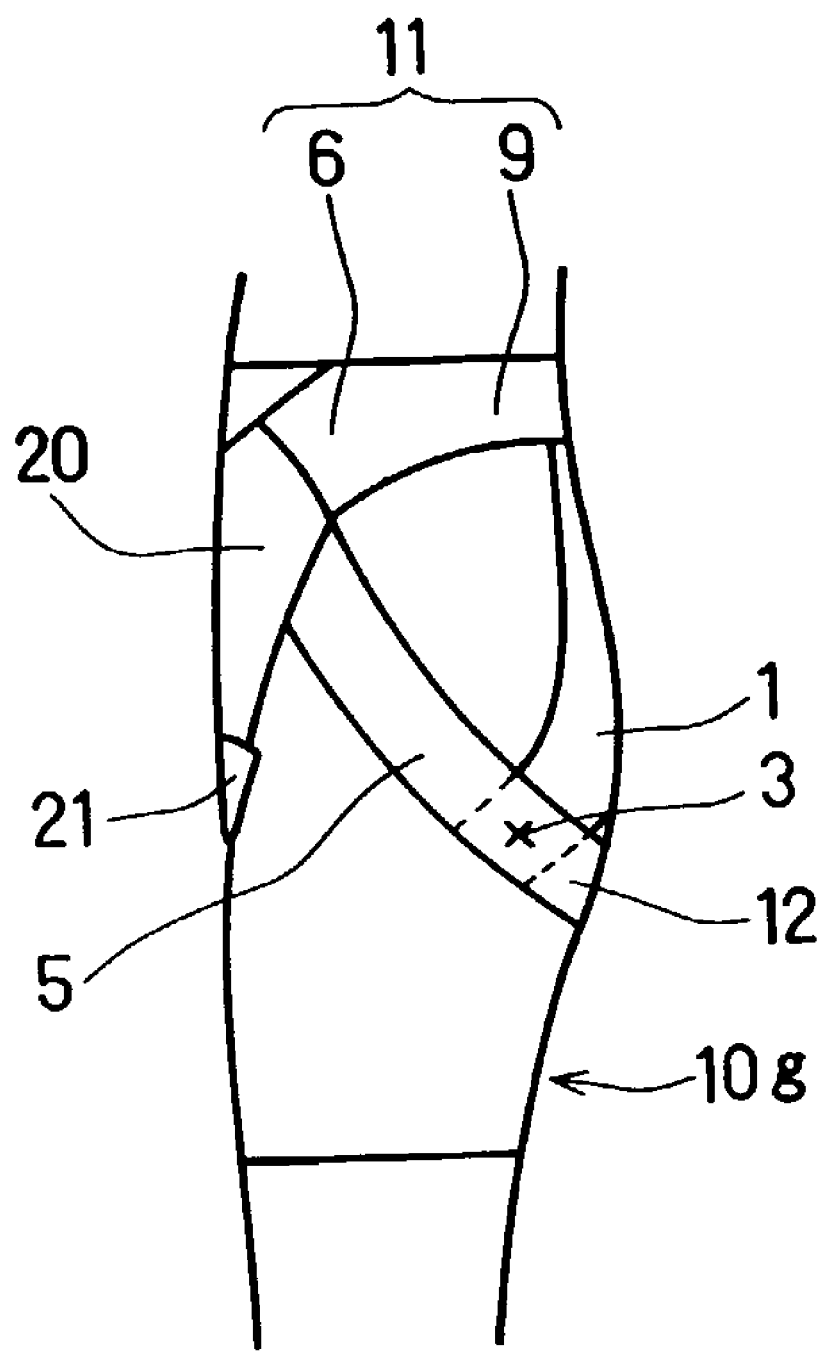
FIG. 20 is a left side view of the long type girdle of FIG. 19 in wearing condition.
Figure 21:
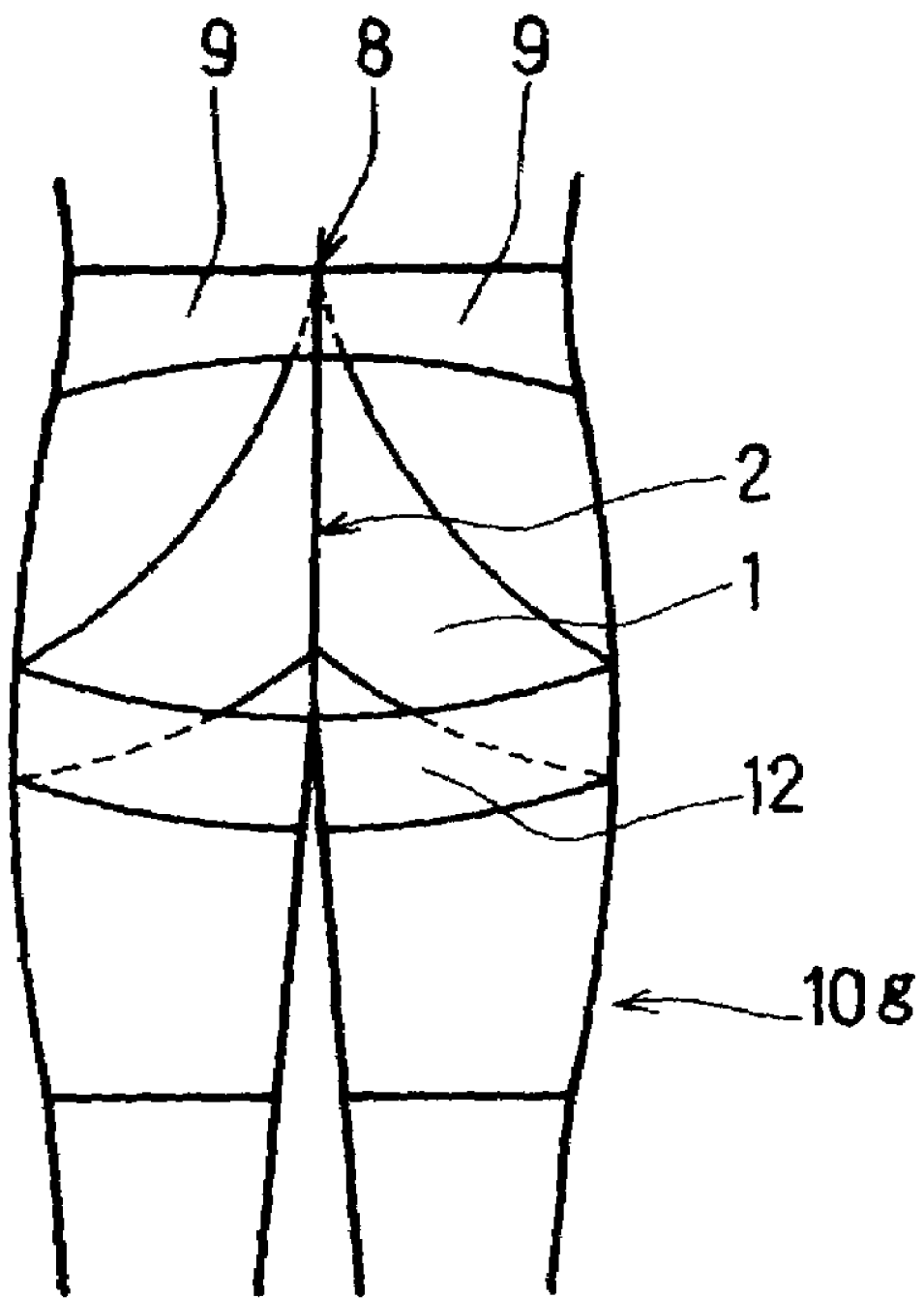
FIG. 21 is a rear view of the long type girdle of FIG. 19 in wearing condition.

Next, FIGS. 19 to 21 show a front view, a left side view and a rear view of still another embodiment of a long type girdle as a garment of the present invention in wearing condition, respectively. The long type girdle 10g shown in FIGS. 19 to 21 is compared with the girdle 10f shown in FIGS. 16 to 18 as follows. In the girdle 10f shown in FIGS. 16 to 18, the strong straining portions 5 and 6 are united approximately at the center of hypogastric region. On the other hand, in the long type girdle 10g shown in FIGS. 19 to 21, a strong straining portion (F) for pressing abdomen indicated by numeral 20, which has a main stretch direction in the longitudinal direction of the garment, is present at the center of hypogastric region.

That is, in this girdle 10g, one end of each of right and left parts of a strong straining portion 5 is connected to each of right and left slightly lower sides of the strong straining portion (F) 20, and one end of each of right and left parts of a strong straining portion 6 is connected to each of right and left upper sides of the strong straining portion (F) 20. Because other points are the same as those in the long type girdle shown in FIGS. 16 to 18, the same signs are applied to the same parts, and detailed descriptions are omitted.

In this girdle 10g, because the right and left parts of the strong straining portion 5 and the right and left parts of the strong straining portion 6 are connected to each other through the strong straining portion (F) 20, approximately the same functions as those of the girdle shown in FIGS. 19 to 21 can be displayed. Particularly, because the strong straining portion (F) 20 is present, the functions of inhibiting the swelling of superfluous flesh of the abdomen and adjusting the shape of the abdomen more finely also are displayed. Furthermore, in FIGS. 19 to 20, numeral 21 indicates a crotch part. Although the fabric forming the crotch part is not particularly limited, in general, a fabric stretchable in the longitudinal direction is used.

Figure 22:
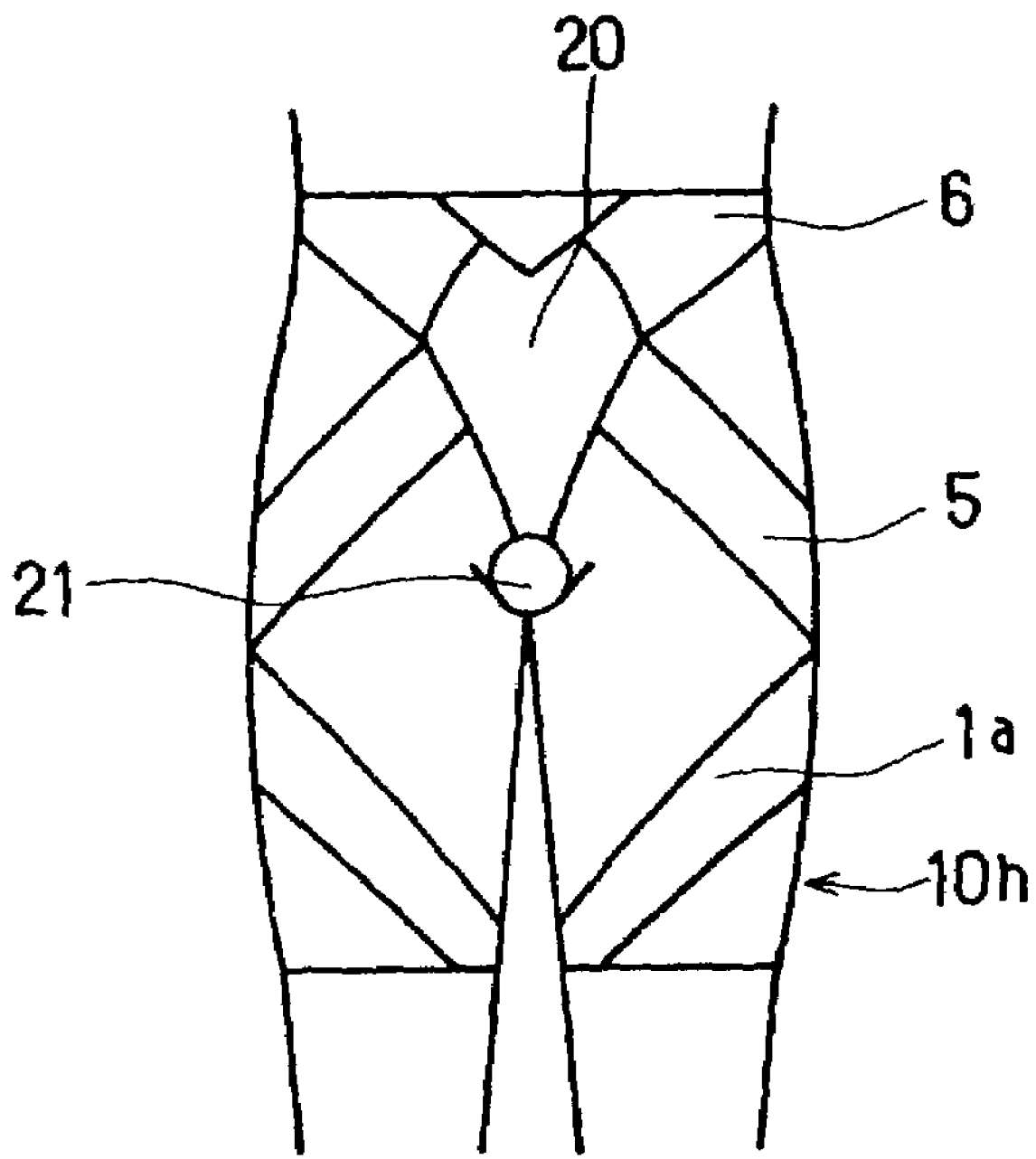
FIG. 22 is a front view of still another embodiment of a long type girdle as a garment of the present invention in wearing condition.
Figure 23:
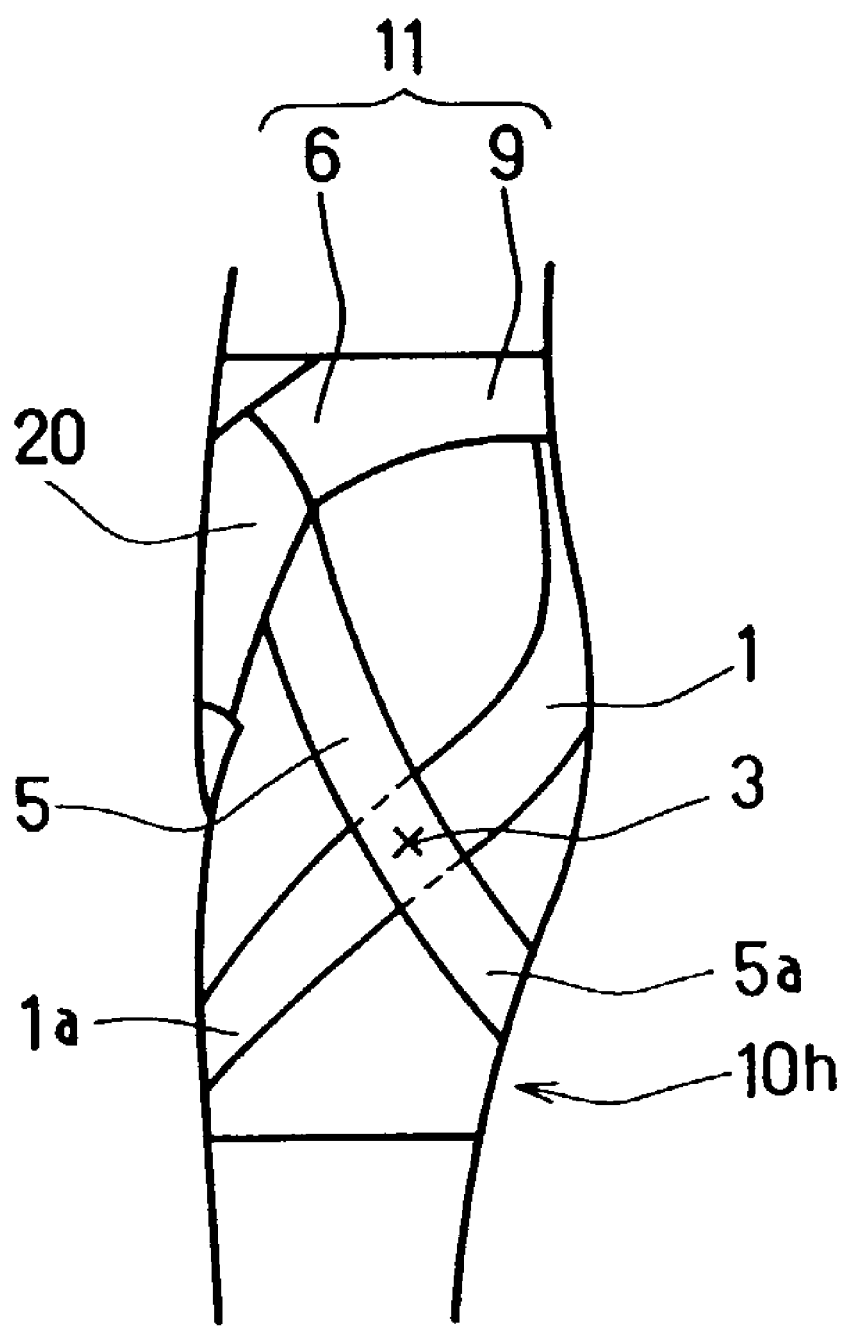
FIG. 23 is a left side view of the long type girdle of FIG. 22 in wearing condition.
Figure 24:
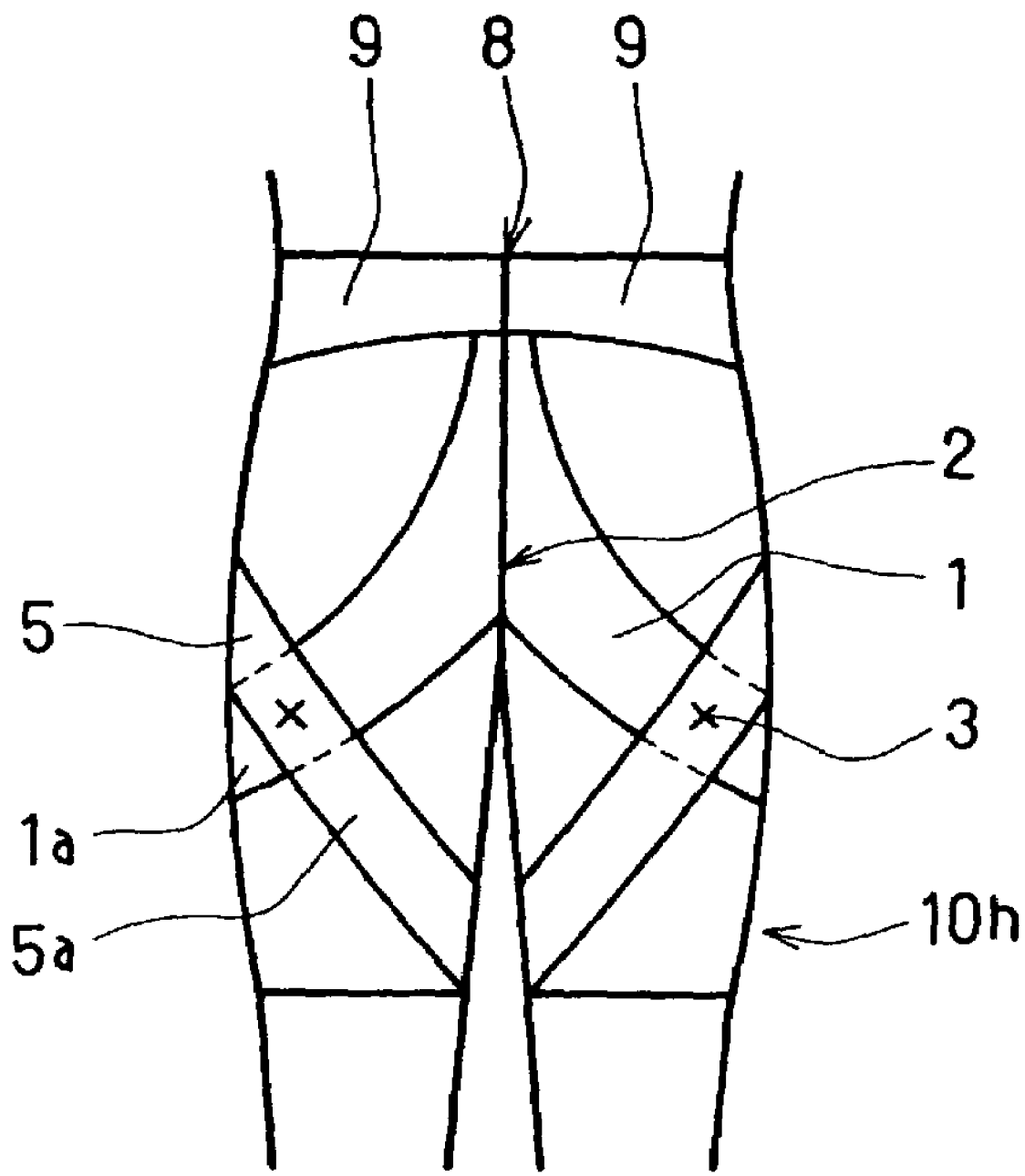
FIG. 24 is a rear view of the long type girdle of FIG. 22 in wearing condition.

Next, FIGS. 22 to 24 show a front view, a left side view and a rear view of still another embodiment of a long type girdle as a garment of the present invention in wearing condition, respectively. The long type girdle 10h shown in FIGS. 22 to 24 is compared with the girdle 10g shown in FIGS. 19 to 21 as follows. In the girdle 10g shown in FIGS. 19 to 21, the portion indicated by the strong straining portion 5 has the strong straining portion 12 extending further from the vicinity of trochanter major 3 through a lower part of the bulges of the buttocks. The strong straining portions 5 and 12 are united to form a strong straining portion (B2). On the other hand, in the long type girdle 10h shown in FIGS. 22 to 24, the portion indicated by the strong straining portion 5 extends further from the vicinity of trochanter major 3 to the vicinity of a part a little higher than patella on the side where fibula (207 in FIG. 52) is present, covering at least a part of musculus biceps femoris, musculus semitendinosus, musculus semimembranosus, etc. in regio femoralis posterior, which are also called hamstrings. When indicating this extended part of the strong straining portion by symbol 5*a*, the strong straining portions 5 and 5*a* are united to form a strong straining portion (B3). Furthermore, in this long type girdle 10*h*, the portion indicated by the strong straining portion 1 further extends from the vicinity of trochanter major 3 toward regio femoralis anterior medialis to the vicinity of a part a little higher than patella on the side where tibia (208 in FIG. 52) is present, covering at least a part of musculus quadriceps femoris such as musculus sartorius, musculus rectus femoris, musculus vastus medialis, etc. approximately in the direction of the muscle fibers thereof. When indicating this extended part of the strong straining portion by symbol 1*a*, the strong straining portions 1 and 1*a* are united to form a strong straining portion (A2). Because other points are the same as those in the long type girdle shown in FIGS. 19 to 21, the same signs are applied to the same parts, and detailed descriptions are omitted.

Except for the difference in the absence of the strong straining portion 12, this girdle 10*h* can display approximately the same functions as those of the girdle shown in FIGS. 19 to 21. In addition, because the girdle 10*h* has the strong straining portions (A2) and (B3), the function of pressing trochanter major 3 is enhanced further, and the functions of improving the joint between caput ossis femoris 204 and acetabulum and increasing the stability of the hip joint are enhanced further. Furthermore, because the strong straining portions 1*a* and 5*a* support musculus quadriceps femoris (musculus sartorius, musculus rectus femoris, musculus vastus medialis, etc.), and musculus biceps femoris, musculus semitendinosus and musculus semimembranosus, which are also called hamstrings, approximately in the direction of their muscle contraction, these muscles in legs are supported when playing sports, and also recovery from muscle fatigue caused by exhaustion of energy or accumulation of lactic acid can be encouraged by generating a massage effect and speeding up flows of blood and lymphocyte. Furthermore, the function of pressing the ground strongly backward in a running action, the function of jumping higher, the function of rising a foot, etc. are enhanced further. When an elderly person wears it, the functions of preventing falling down and increasing walking stability are enhanced further.

Figure 25:
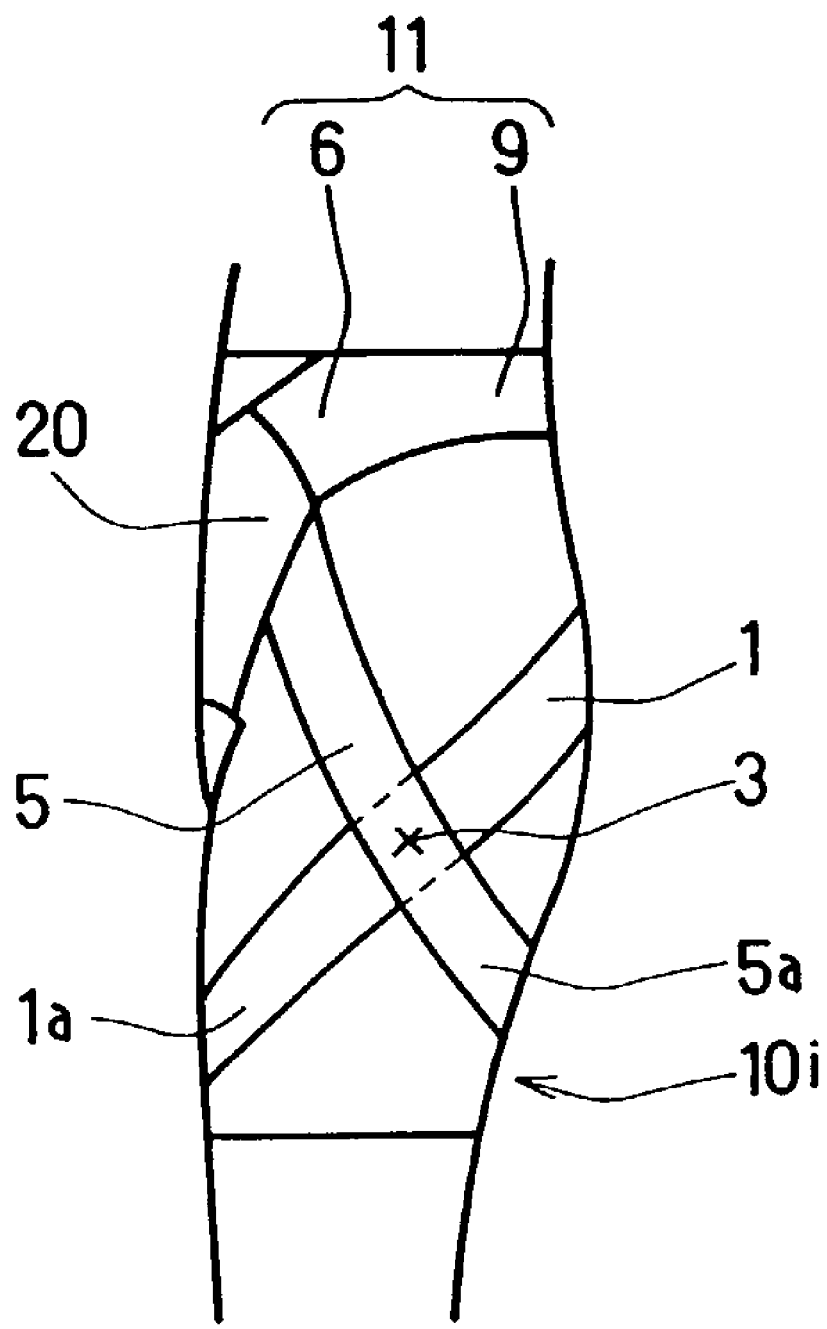
FIG. 25 is a left side view of still another embodiment of a long type girdle as a garment of the present invention in wearing condition.
Figure 26:
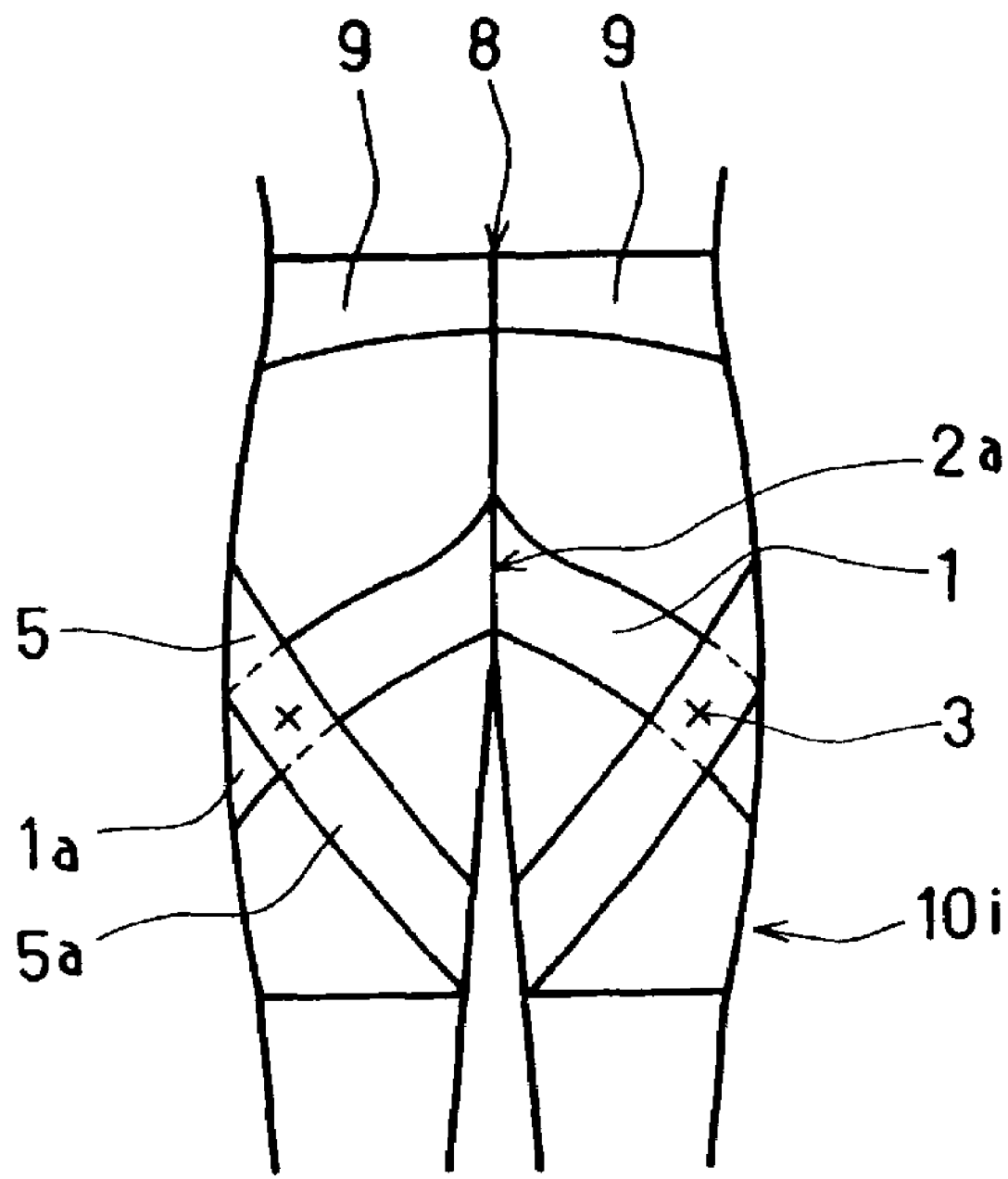
FIG. 26 is a rear view of the long type girdle of FIG. 25 in wearing condition.

Next, FIGS. 25 to 26 show a left side view and a rear view of still another embodiment of a long type girdle as a garment of the present invention in wearing condition, respectively. Because the front view of this girdle is the same as FIG. 22, illustration is omitted. The girdle 10*i* shown in FIGS. 25 to 26 is compared with the girdle 10*h* shown in FIGS. 22 to 24 as follows. In the girdle 10*h* shown in FIGS. 22 to 24, the right and left parts of the strong straining portion 1 are connected at the position 2 on the back side of the girdle corresponding to from the fourth vertebra lumbalis to os sacrum of the wearer's body. On the other hand, in the girdle 10*i* shown in FIGS. 25 to 26, the right and left parts of the strong straining portion 1 are connected at the position 2*a* on the back side of the girdle corresponding to os sacrum of the wearer's body. Because other points are the substantially the same as those in the long type girdle 10*h* shown in FIGS. 22 to 24, the same signs are applied to the same parts, and detailed descriptions are omitted.

In the girdle 10*i* shown in FIGS. 25 to 26, the area of musculus gluteus maximus covered by the strong straining portion 1 is a little smaller than that in the long type girdle 10*h* shown in FIGS. 22 to 24, and the function of the strong straining portion 1 is reduced a little by the proportion of the decreased area. However, the girdle 10*i* still can support musculus gluteus maximus sufficiently in the direction of its muscle fibers. Therefore, with the girdle 10*i* shown in FIGS. 25 to 26, a girdle that can display approximately the same functions as those of the long type girdle 10*h* shown in FIGS. 22 to 24 can be obtained.

Figure 27:
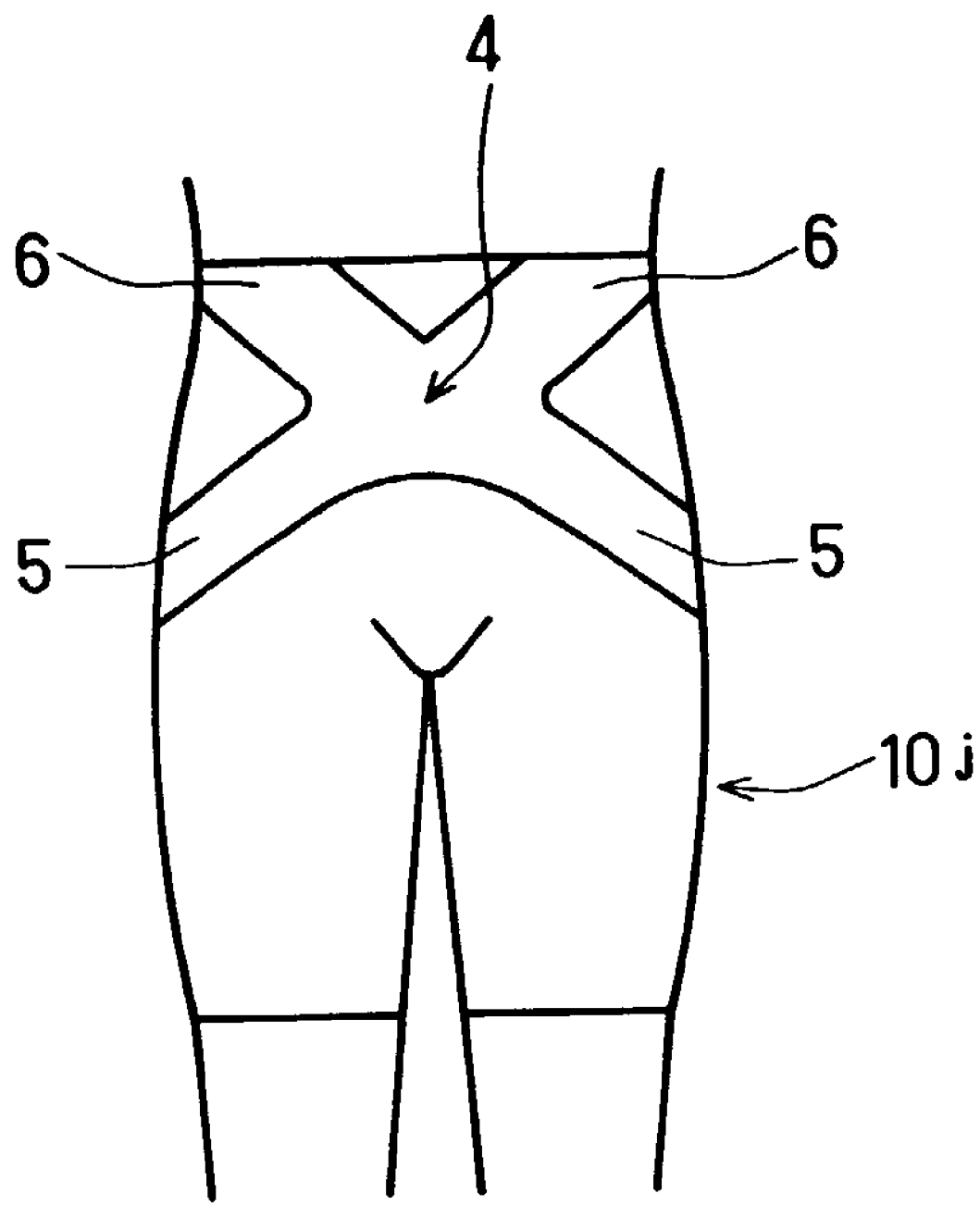
FIG. 27 is a front view of still another embodiment of a long type girdle as a garment of the present invention in wearing condition.
Figure 28:
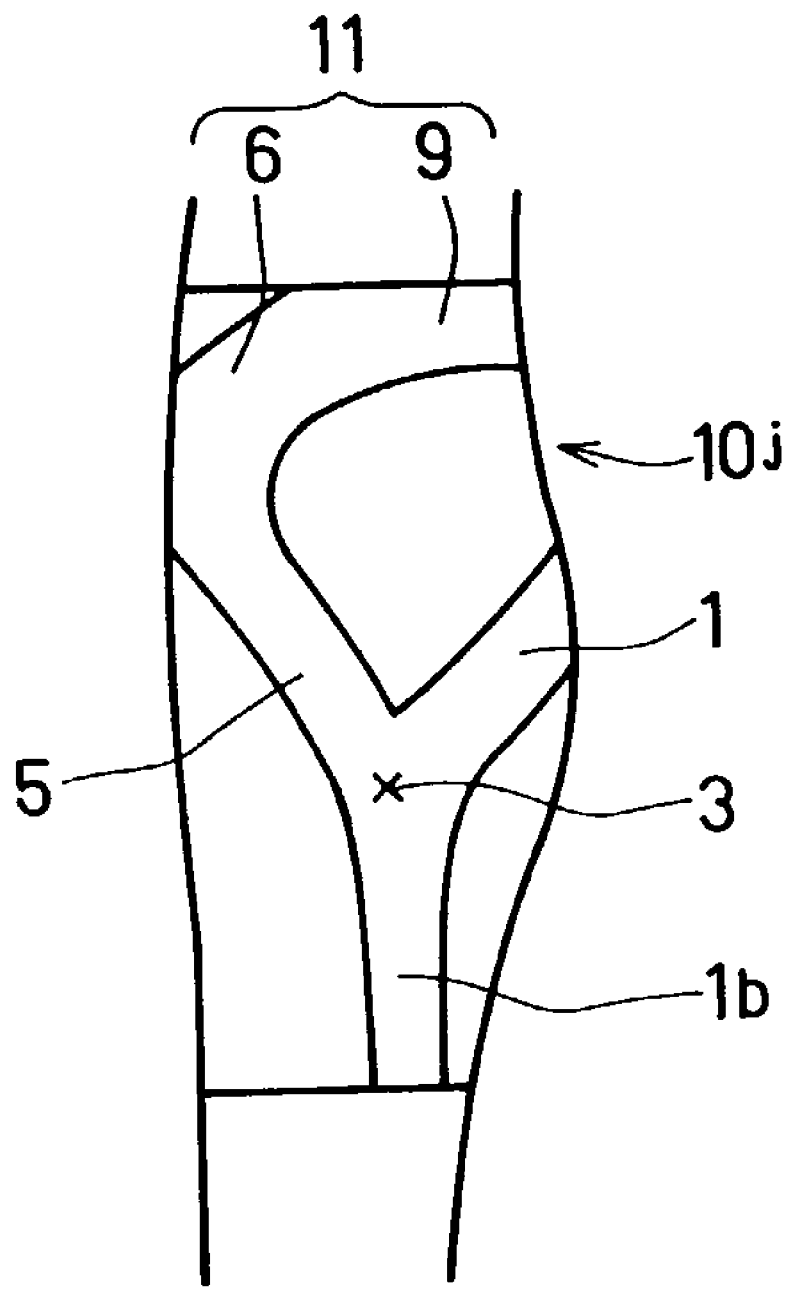
FIG. 28 is a left side view of the long type girdle of FIG. 27 in wearing condition.
Figure 29:
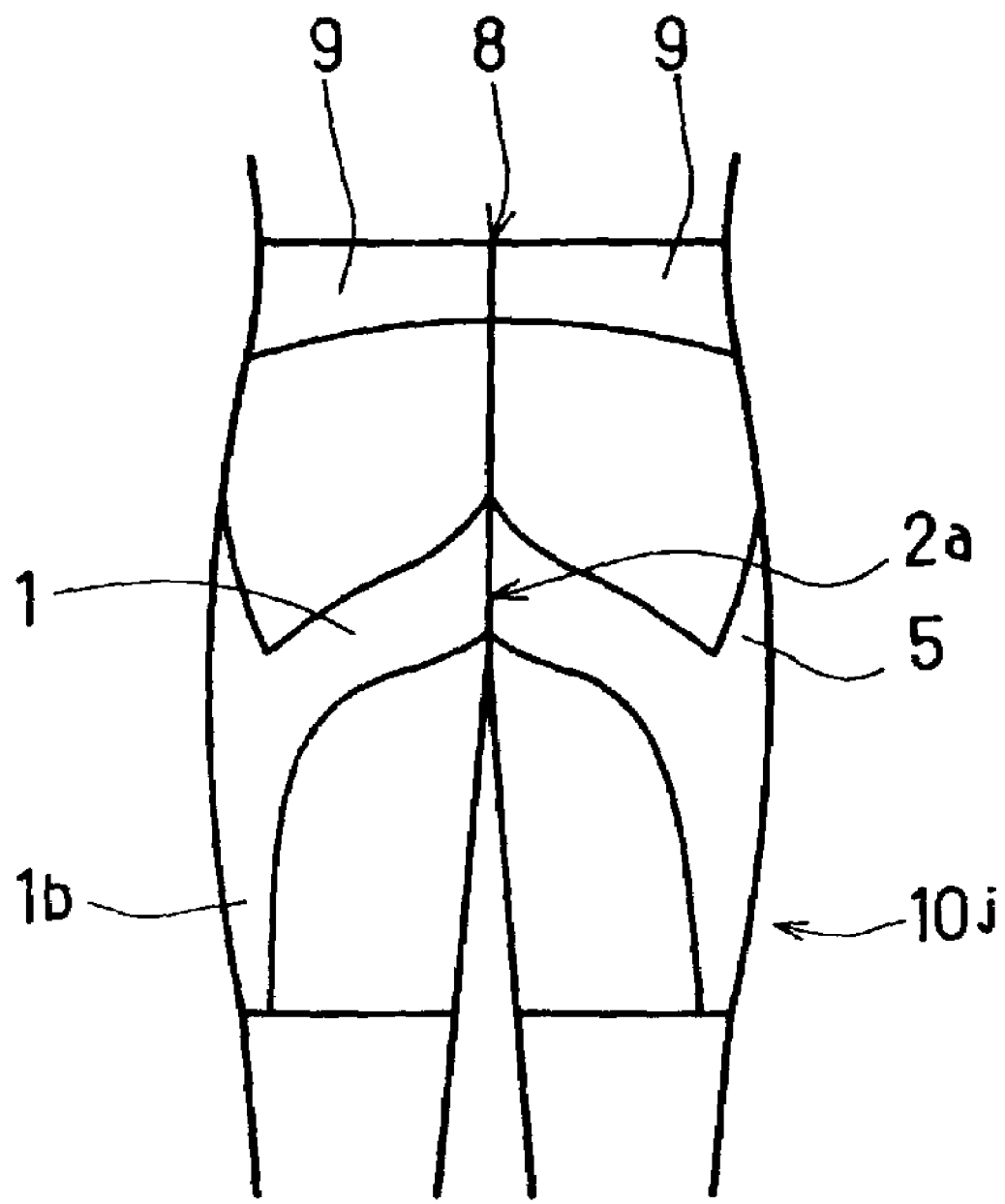
FIG. 29 is a rear view of the long type girdle of FIG. 27 in wearing condition.

Next, FIGS. 27 to 29 show a front view, a left side view and a rear view of still another embodiment of a long type girdle as a garment of the present invention in wearing condition, respectively. In the long type girdle 10*j* shown in FIGS. 27 to 29, the arrangement of the strong straining portions 5 and 6 on the front side is the same as that shown in the front view of the girdle shown in FIG. 13. Furthermore, the girdle 10*j* is the same as the girdle shown in FIG. 26 in that right and left parts of the strong straining portion 1 are connected at the position 2*a* on the back side of the girdle corresponding to os sacrum of the wearer's body. This girdle is peculiar in that the strong straining portions 1 and 5 are combined at the position of trochanter major 3, and it further has a strong straining portion 1*b* extending from the position of trochanter major 3 downward approximately in the direction of muscle fibers of tractus iliotibialis (see 311 of FIG. 71) to a part a little higher than patella. The strong straining portion in which the strong straining portion 1 is united with the strong straining portions 1*b* or a strong straining portions 1*c* described below with reference to FIG. 31 is referred to as a strong straining portion (A3).

In the girdle 10*j* shown in FIGS. 27 to 29, because the portion indicated by the strong straining portion 5 is united with the strong straining portion 1 in the vicinity of trochanter major 3, and further has the strong straining portion 1*b* extending downward approximately in the direction of muscle fibers of tractus iliotibialis to patella, the vicinity of trochanter major 3 can be pulled and pressed from three directions of the strong straining portions 5, 1 and 1*b*. Compared with the girdle shown in FIGS. 13 to 15, the function of pressing trochanter major 3 is enhanced further, and the functions of improving the joint between caput ossis femoris 204 and acetabulum and increasing the stability of the hip joint are enhanced further. In addition, the strong straining portions 6, 5 and 9 located at the same positions as those in the girdle of FIGS. 13 to 15 display the same functions as those of the girdle shown in FIGS. 13 to 15, and the strong straining portion 1 located at the same position as that in the girdle shown in FIGS. 25 to 26 displays the same function as that of the girdle of FIGS. 25 to 26.

Figure 30:
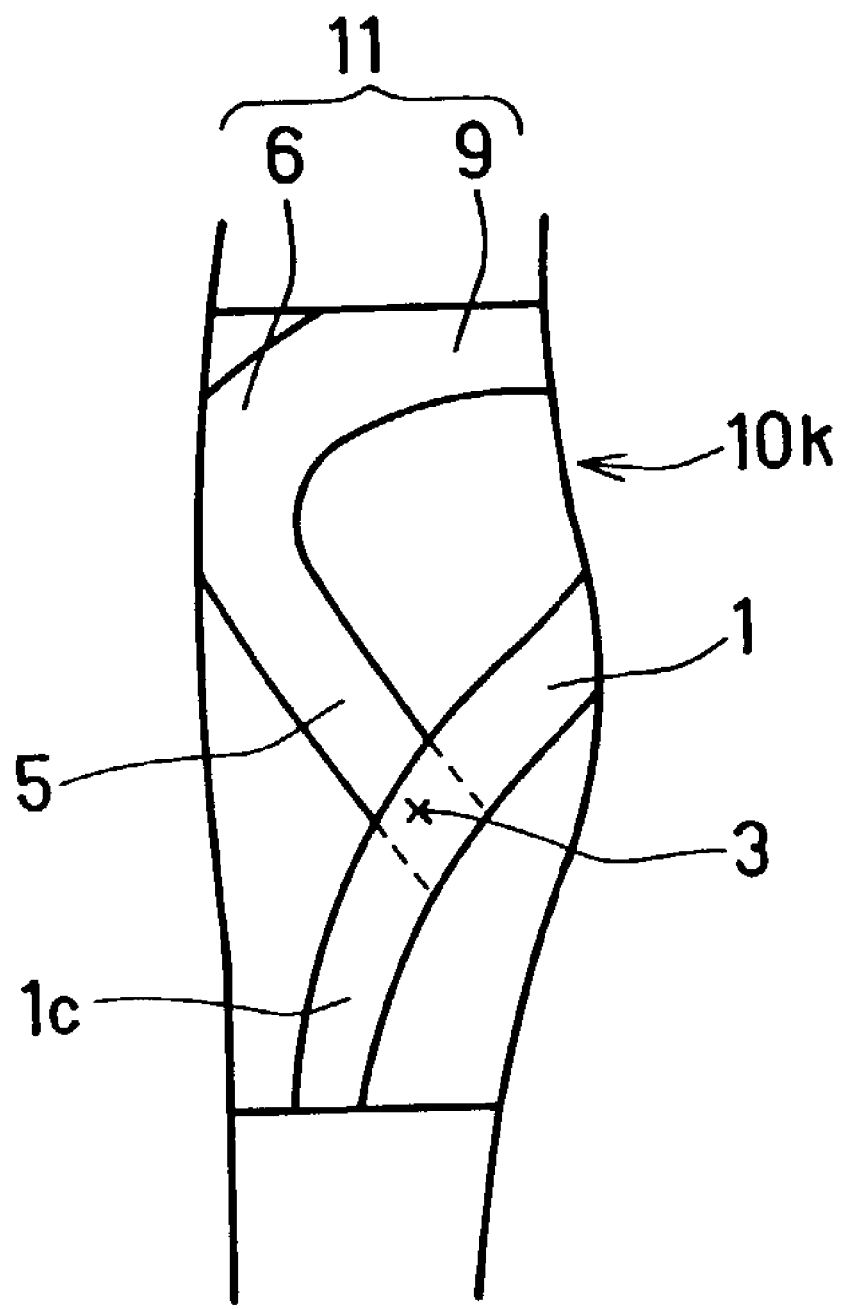
FIG. 30 is a left side view of still another embodiment of a long type girdle as a garment of the present invention in wearing condition.
Figure 31:
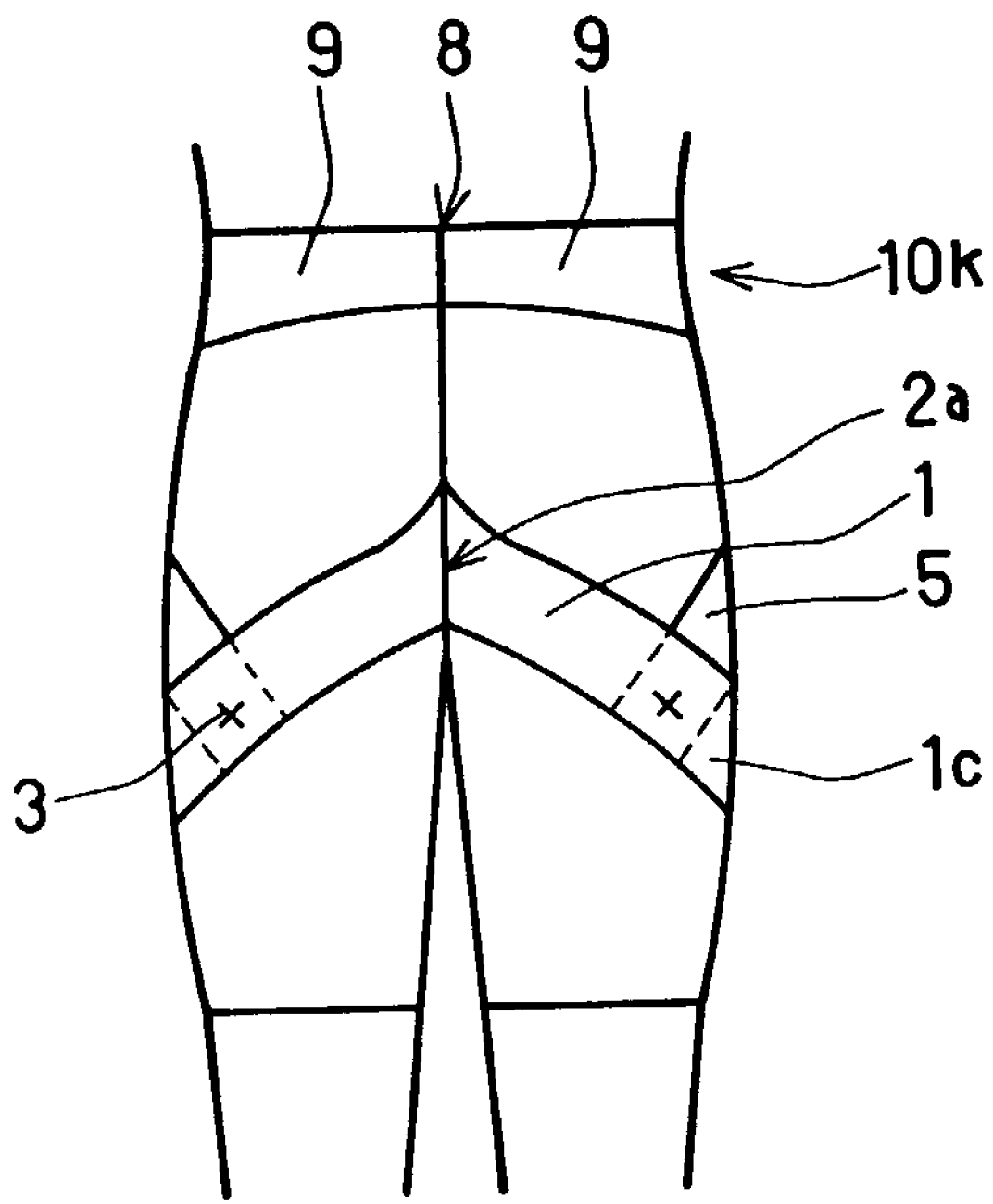
FIG. 31 is a rear view of the long type girdle of FIG. 30 in wearing condition.

Next, FIGS. 30 to 31 show a left side view and a rear view of still another embodiment of a long type girdle as a garment of the present invention in wearing condition, respectively. Because the front view of this girdle is the same as FIG. 27, illustration is omitted. The long type girdle 10*k* shown in FIGS. 30 to 31 is compared with the long type girdle 10*j* shown in FIGS. 27 to 29 as follows. In the girdle 10*j* shown in FIGS. 27 to 29, the strong straining portion 1 is united with the strong straining portion 5 at the position of trochanter major 3, and the strong straining portion 1 further has a strong straining portions 1*b* extending downward from the position of trochanter major 3 approximately in the direction of muscle fibers of tractus iliotibialis to patella. On the other hand, in the long type girdle 10*k* shown in FIGS. 30 to 31, the strong straining portions 1 and 5 are united at the position of trochanter major 3, and the strong straining portion 1 further has a strong straining portion 1c extending obliquely downward from the position of trochanter major 3 to the medial side of the wearer's body approximately in the direction of muscle fibers of musculus vastus lateralis (see 305 in FIG. 70) to a part a little higher than patella. Musculus vastus lateralis is supported by the strong straining force 1c, and the functions of generating a massage effect on this muscle and encouraging recovery from muscle fatigue, etc. are displayed. For other points, approximately the same functions as those of the girdle 10j shown in FIGS. 27 to 29 can be displayed.

Figure 32:
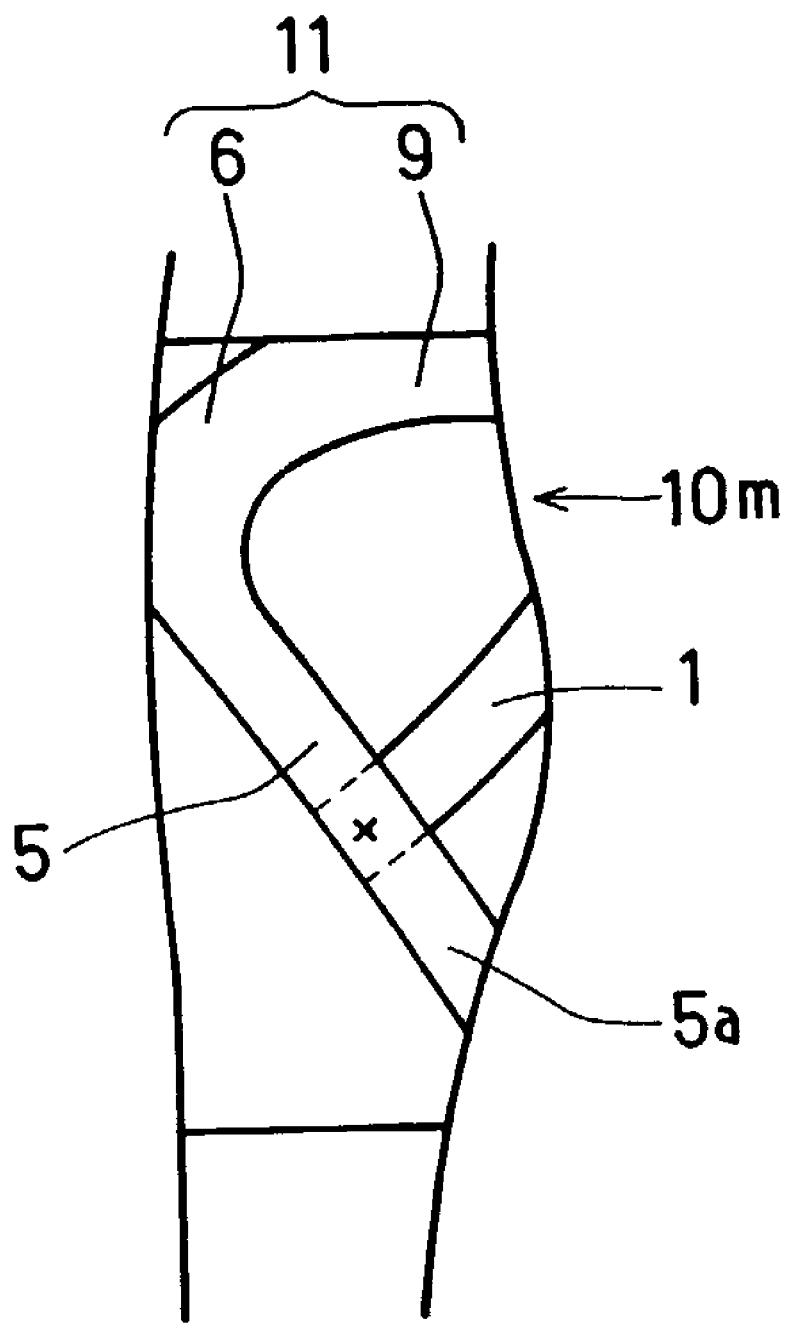
FIG. 32 is a left side view of still another embodiment of a long type girdle as a garment of the present invention in wearing condition.
Figure 33:
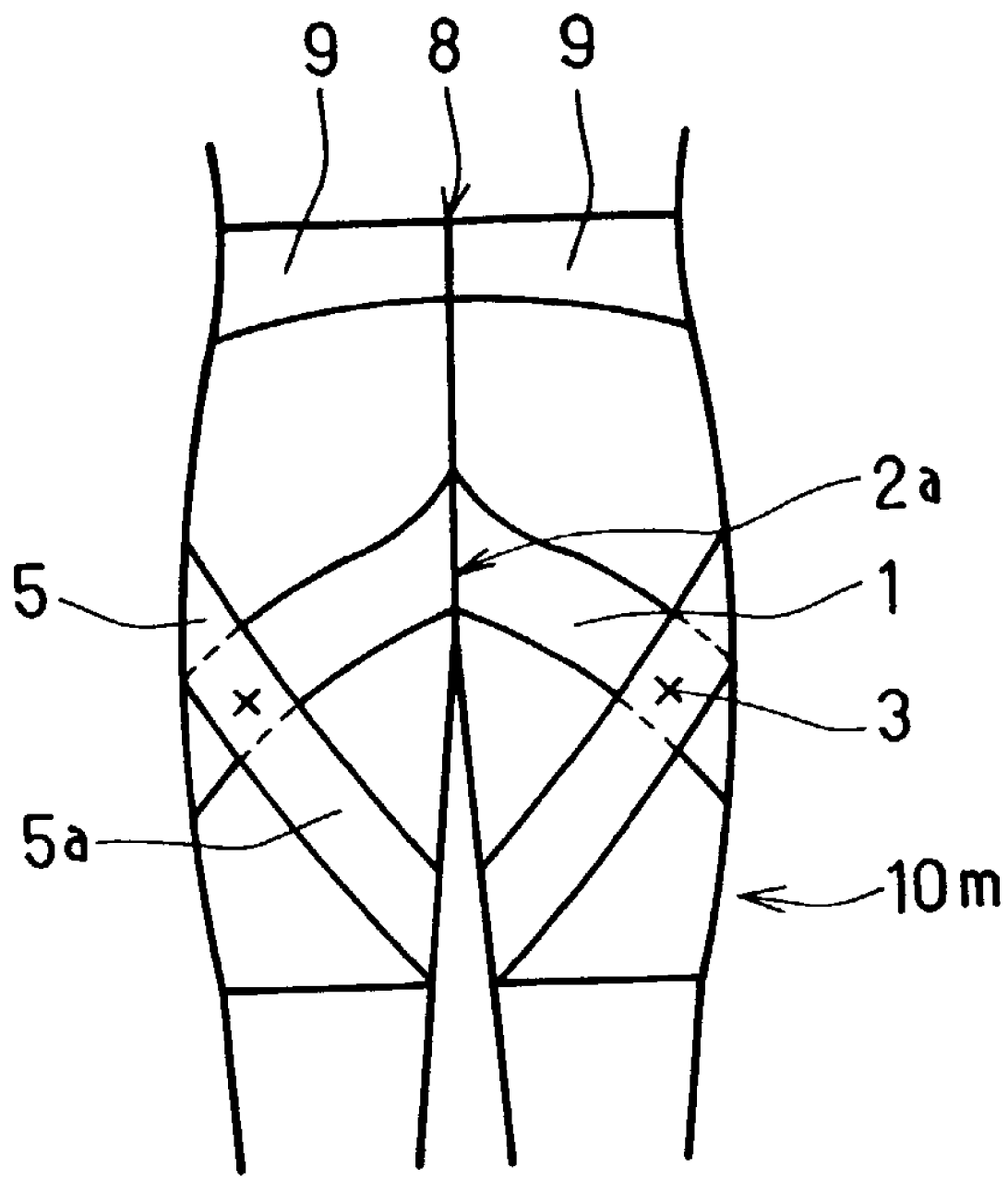
FIG. 33 is a rear view of the long type girdle of FIG. 32 in wearing condition.

Next, FIGS. 32 and 33 show a left side view and a rear view of still another embodiment of a long type girdle as a garment of the present invention in wearing condition, respectively. Because the front view of this girdle is the same as FIG. 27, illustration is omitted. The long type girdle 10m shown in FIGS. 32 to 33 is compared with the girdle 10j shown in FIGS. 27 to 29 as follows. In the girdle 10j shown in FIGS. 27 to 29, the strong straining portions 1 is united with the strong straining portion 5 at the position of trochanter major 3, and it further has the strong straining portion 1b extending downward from the position of trochanter major 3 approximately in the direction of muscle fibers of tractus iliotibialis to patella. On the other hand, in the long type girdle 10m shown in FIGS. 32 to 33, the strong straining portion 1 is united with the strong straining portion 5 at the position of trochanter major 3, and in the same manner as in the girdle of FIGS. 23 and 24, the strong straining portion 5 further extends from the vicinity of trochanter major 3 to the vicinity of the upper end of fibula, covering at least a part of hamstrings in regio femoralis posterior. The strong straining portions 5 and 5a are united to form a strong straining portion (B3). Because the strong straining portions 5a support musculus quadriceps femoris and hamstrings approximately in the direction of muscle contraction, when playing sports, the function of encouraging recovery from muscle fatigue by a massage effect on these muscles in legs, the function of pressing the ground strongly backward in a running action, the function of jumping higher, the function of rising a foot, etc. are enhanced further. When an elderly person wears it, the functions of preventing falling down and increasing walking stability are enhanced further. For other functions, approximately the same functions as those of the girdle 10j in FIGS. 27 to 29 can be displayed.

Figure 34:
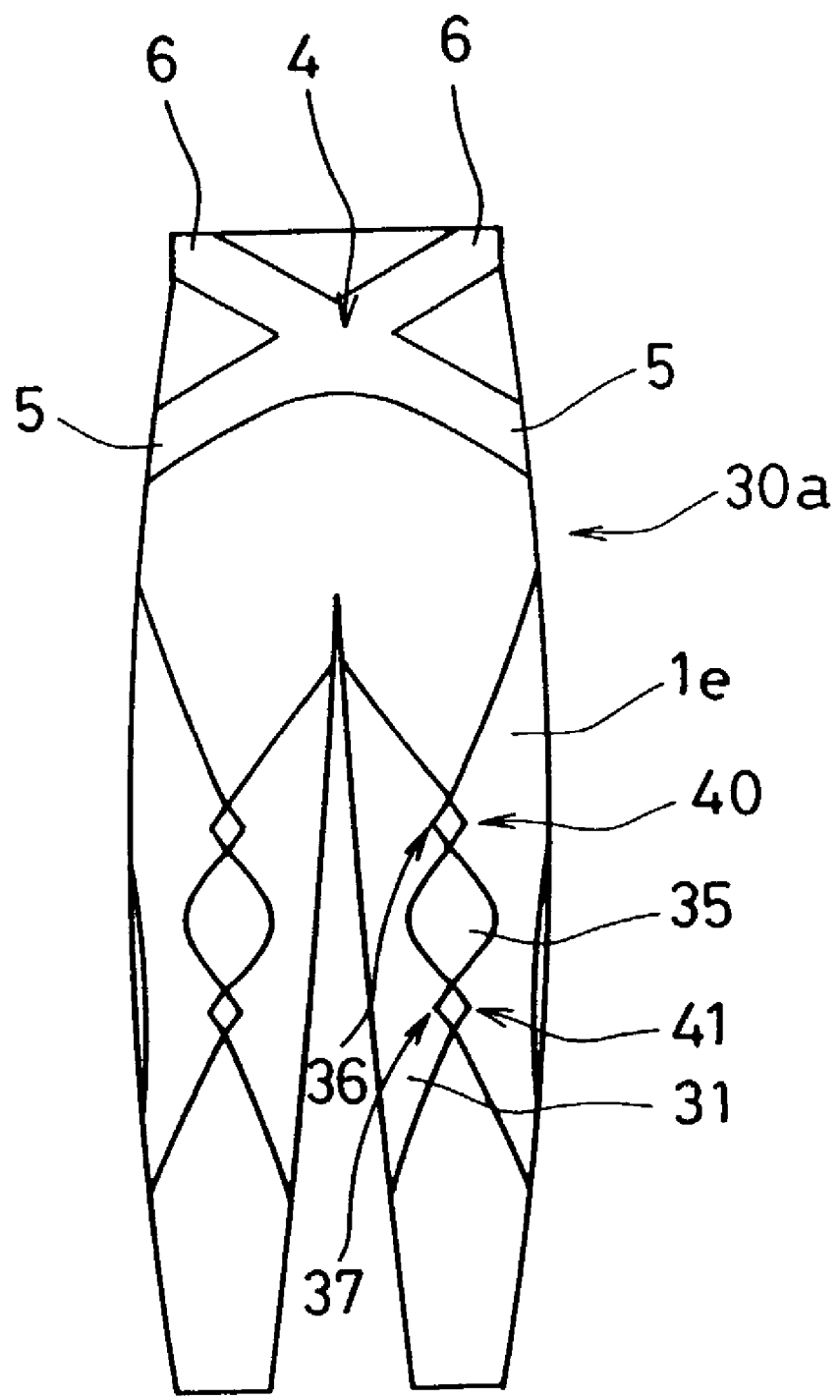
FIG. 34 is a front view of sports tights as a garment of the present invention.
Figure 35:
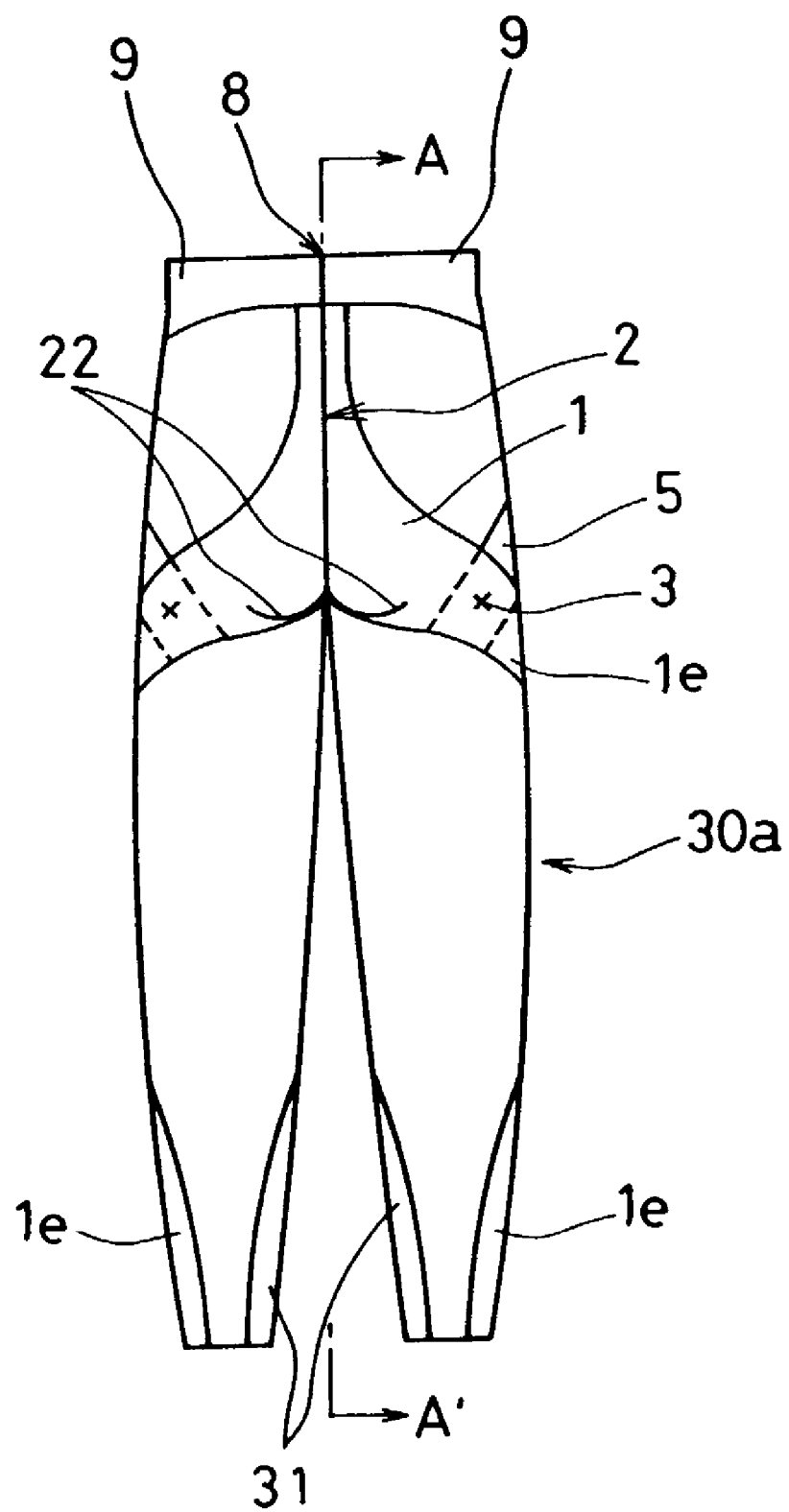
FIG. 35 is a rear view of the sports tights of FIG. 34.
Figure 36:
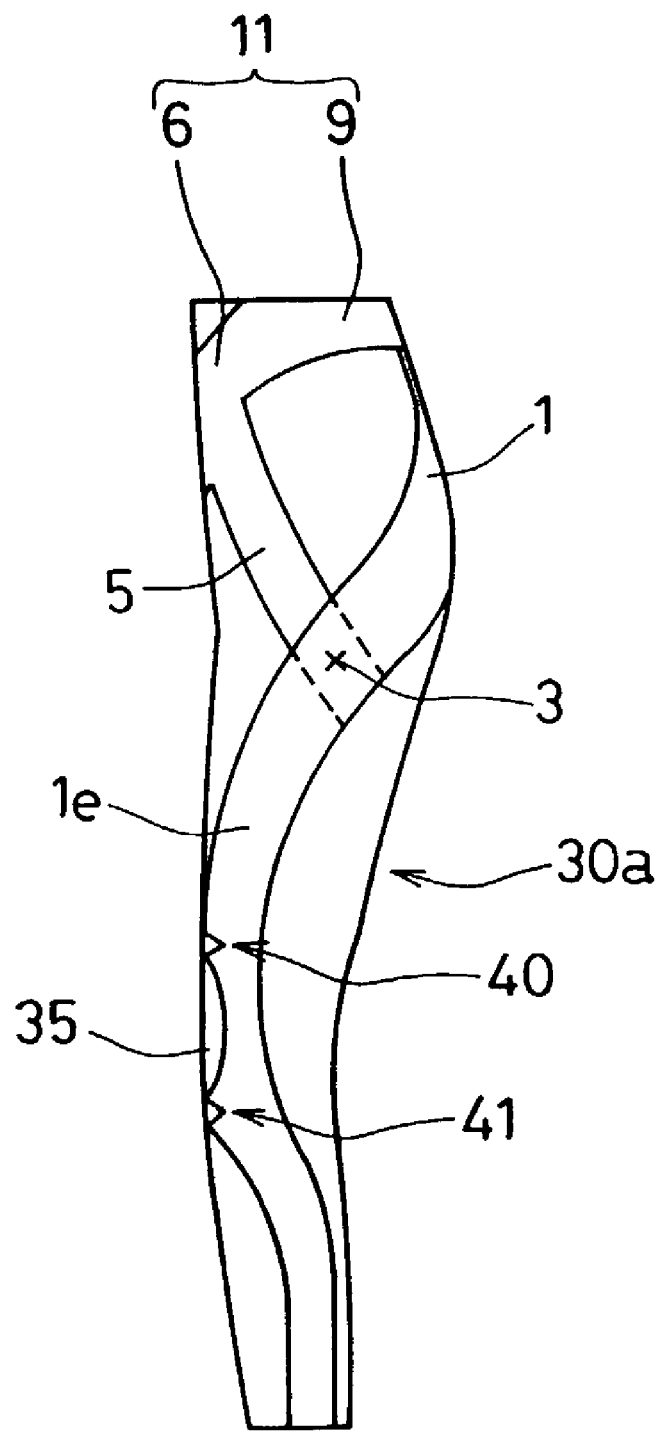
FIG. 36 is a left side view of the sports tights of FIG. 34.
Figure 37:
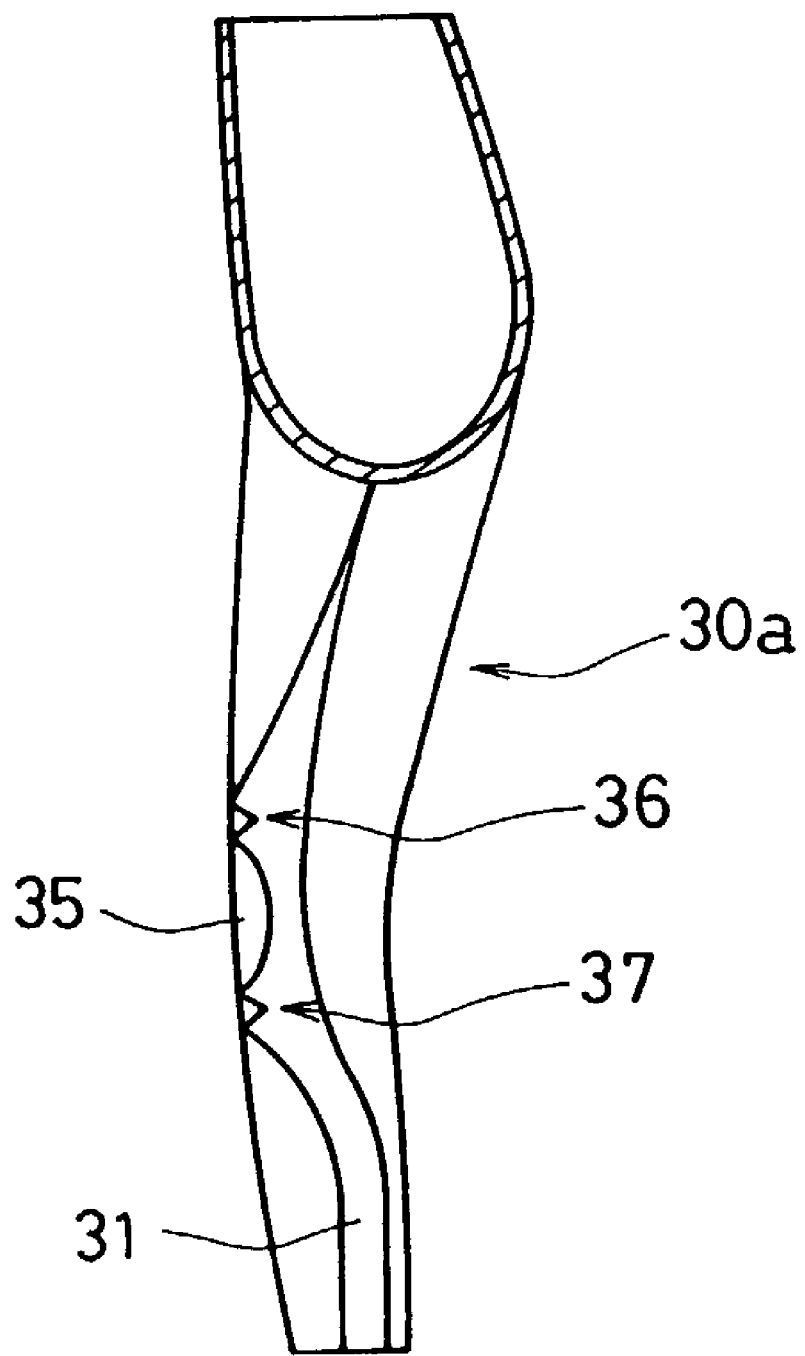
FIG. 37 is a schematic sectional view of the sports tights of FIG. 35 taken along the line A–A'.

Next, FIGS. 34 to 36 show a front view, a rear view and a left side view of sports tights as a garment of the present invention in wearing condition, respectively. FIG. 37 is a schematic sectional view of FIG. 35 taken along the line A–A'. In the sports tights 30a shown in FIGS. 34 to 37, the strong straining portions 6, 5 and 9 are the same as those of the girdle 10k shown in FIGS. 30 to 31. In the sports tights 30a shown in FIGS. 34 to 37, the strong straining portion 1 has a strong straining portion 1e covering a region further from the vicinity of trochanter major 3 through the vicinity of tractus iliotibialis and musculus vastus lateralis approximately in the direction of their muscle fibers to a side of patella 35, and further from the side of patella 35 through the vicinity of musculus gastrocnemius and musculus soleus in regio cruris lateralis approximately in the direction of their muscle fibers to the vicinity of an upper part of malleolus lateralis so as to support musculus gastrocnemius and musculus soleus. The strong straining portion comprising the strong straining portions 1 and 1e is referred to as a strong straining portion (A4). Furthermore, as shown in FIG. 37, the sports tights 30a further have a strong straining portion (E) 31 extending further from regio femoralis medialis through musculus vastus medialis approximately in the direction of its muscle fibers to a side of patella 35 so as to support musculus vastus medialis, and further from the side of patella 35 through the vicinity of musculus gastrocnemius and musculus soleus in regio cruris medialis approximately in the direction of their muscle fibers to the vicinity of an upper part of malleolus medialis so as to support musculus gastrocnemius and musculus soleus.

Describing the genu region in more detail with reference to FIG. 34, it is preferable that in the strong straining portion 1e on the lateral side, two mountains 36 and 37 are formed on the medial sides of the upper and lower parts with respect to patella 35 so as to avoid patella 35, and in the strong straining portion 31 on the medial side, two mountains 40 and 41 are formed on the lateral sides of the upper and lower parts with respect to patella 35 so as to avoid patella 35, while the opposing two mountains 40 and 41 and two mountains and 36 and 37 cross each other. By having such a structure in the genu region, the sports tights have the function of supporting ligamentum patellae and ligamentum collaterale. The arrangement of the strong straining portions in the genu region is not limited to the above-described embodiment. Other parts of the main body of the sports tights 30a comprise a stretch fabric having a smaller straining force than those of the above-mentioned strong straining portions. In FIG. 35, numeral 22 schematically shows the position of sulcus gluteus.

In the sports tights 30a shown in FIGS. 34 to 37, musculus gluteus maximus can be supported firmly in the direction of its muscle fibers by the strong straining portion 1. Therefore, it can play a large role in extending the hip joint, particularly for the stability of the pelvis in anterior-posterior direction. Furthermore, it is effective in preventing a decrease in the rotating angle of the hips to the right and left, and for an elderly person in preventing falling down. Furthermore, it can play a large role in extending the hip joint in anterior-posterior direction when running, jumping, and climbing up a slope. Furthermore, because the strong straining portions 1, 1e and 5 cover the vicinity of trochanter major 3 from three directions, the joint between caput ossis femoris 204 and acetabulum can be improved further, and the stability of the hip joint can be increased. Furthermore, in this sports tights 30a, because the strong straining portions 5 and 6 are united at the position 4 on musculus rectus abdominis in hypogastric region, the functions of supporting abdominal muscles more strongly, reducing lumbar lordosis, maintaining good posture, making youthful figure, and preventing generation of pains such as lumbar pains are displayed more easily. Furthermore, because the strong straining portions 6 and 9 are united to form the strong straining portion 11, the functions of strongly supporting the region from the vicinity of the position 8 at the back center of the waist through musculus latissimus dorsi 308 and musculus gluteus medius 309 at right and left and musculus obliquus externus abdominis 302 more strongly, preventing backward inclination of the pelvis, and maintaining a stable position of the pelvis are displayed more easily. Furthermore, because the sports tights 30a have a strong straining portion (A4) comprising the strong straining portions 1 and 1e and a strong straining portion (E) comprising the strong straining portion 31, when playing sports, a massage effect is generated on the muscles in leg regions supported by these strong straining portions, and the function of encouraging the recovery from fatigue of these muscles is displayed. Furthermore, when an elderly person wears it, its functions of preventing falling down and increasing walking stability are enhanced further.

Figure 38:
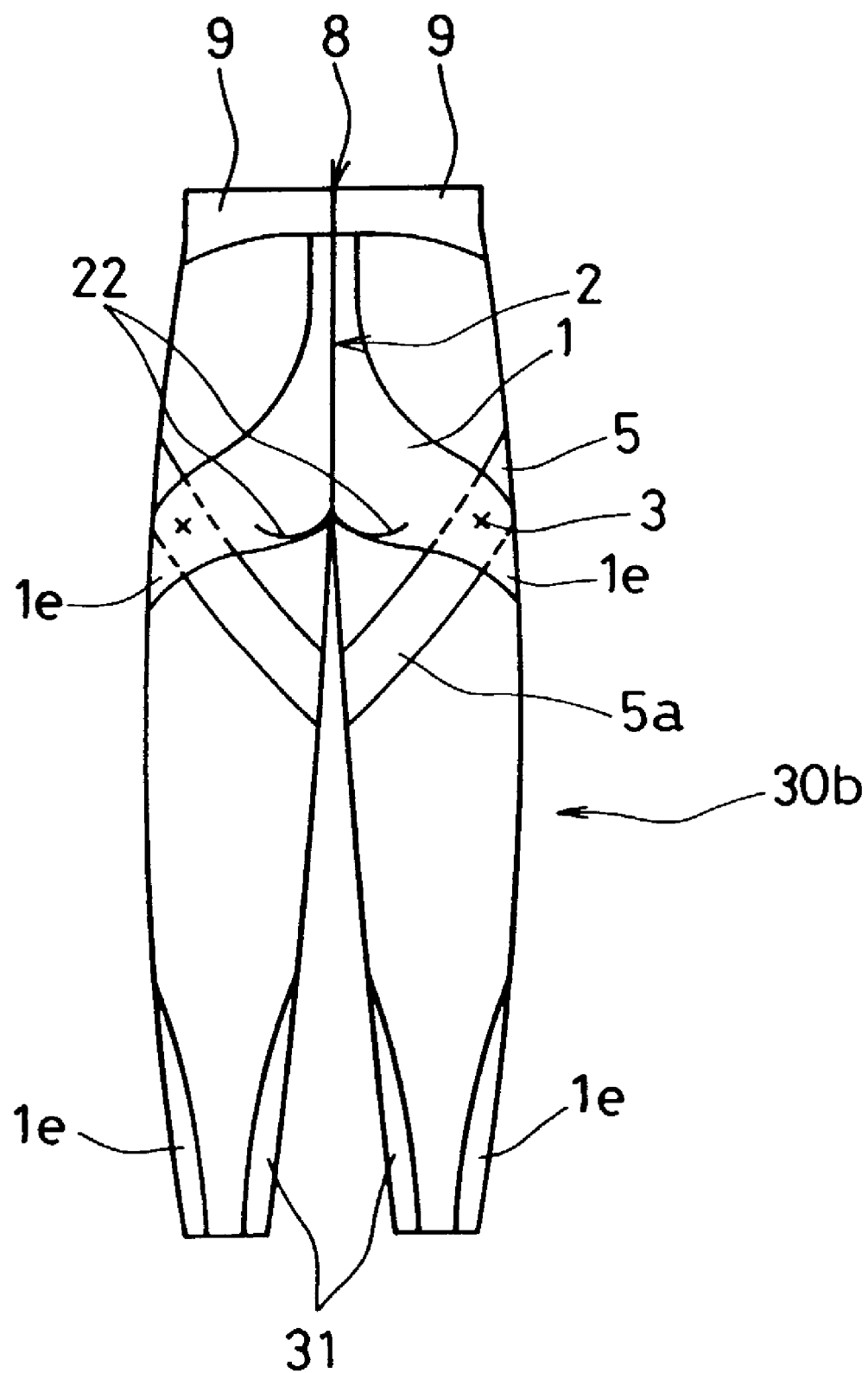
FIG. 38 is a rear view of another embodiment of sports tights as a garment of the present invention.
Figure 39:
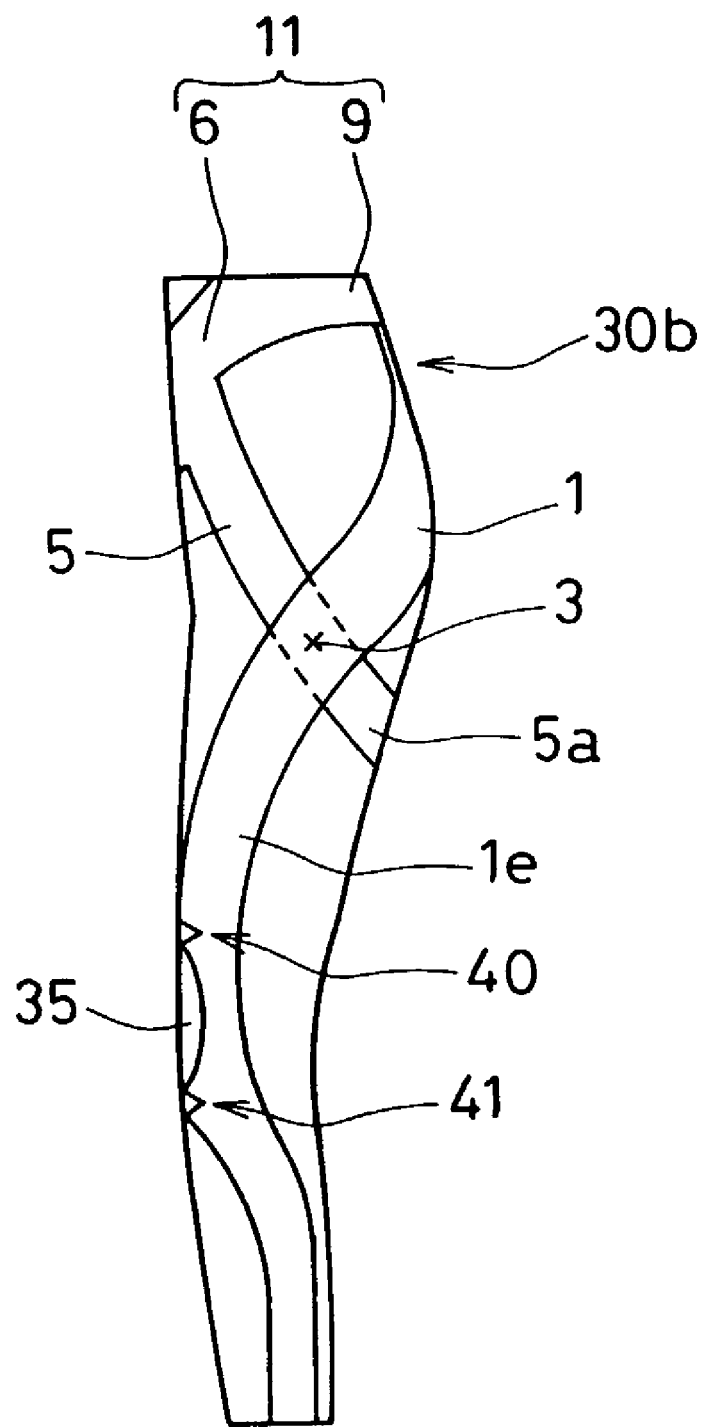
FIG. 39 is a left side view of the sports tights of FIG. 38.

Next, FIGS. 38 to 39 show a rear view and a left side view of another embodiment of sports tights as a garment of the present invention, respectively. Because its front view is the same as FIG. 34, illustration is omitted.

The sport tights 30b shown in FIGS. 38 to 39 is compared with the sports tights 30a shown in FIGS. 34 to 37 as follows. In the sports tights 30a shown in FIGS. 34 to 37, the lower end of the portion indicated by the strong straining portion 5 is located in the vicinity of trochanter major 3. On the other hand, in the sports tights 30b shown in FIGS. 38 to 39, the portion indicated by the strong straining portion 5 further extends from the vicinity of trochanter major 3 to a part a little higher than patella on the side where fibula (207 in FIG. 70) is present, covering at least a part of hamstrings in regio femoralis posterior. The strong straining portions 5 and 5a are united to form a strong straining portion (B3). Because other points are the same as those in the sports tights 30a shown in FIGS. 34 to 37, the same signs are applied to the same parts, and detailed descriptions are omitted.

Because the sports tights 30b have the same functions as those of the sports tights 30a shown in FIGS. 34 to 37, and also has a strong straining portion (B3) in which the strong straining portions 5 and 5a are united in the vicinity of trochanter major 3, the function of pressing trochanter major 3 is enhanced further, and the functions of improving the joint between caput ossis femoris 204 and acetabulum and increasing the stability of the hip joint are enhanced further. Furthermore, because the strong straining portion 5a supports musculus biceps femoris, musculus semitendinosus and musculus semimembranosus, which are also called hamstrings, approximately in the direction of their muscle contraction, when playing sports, etc., the function of pressing the ground strongly backward in a running action, the function of jumping higher, the function of rising a foot, etc. are enhanced further. Furthermore, a massage effect is generated on these muscles, and the recovery from fatigue of these muscles is encouraged. Furthermore, when an elderly person wears it, its functions of preventing falling down and increasing walking stability are enhanced further.

Figure 40:
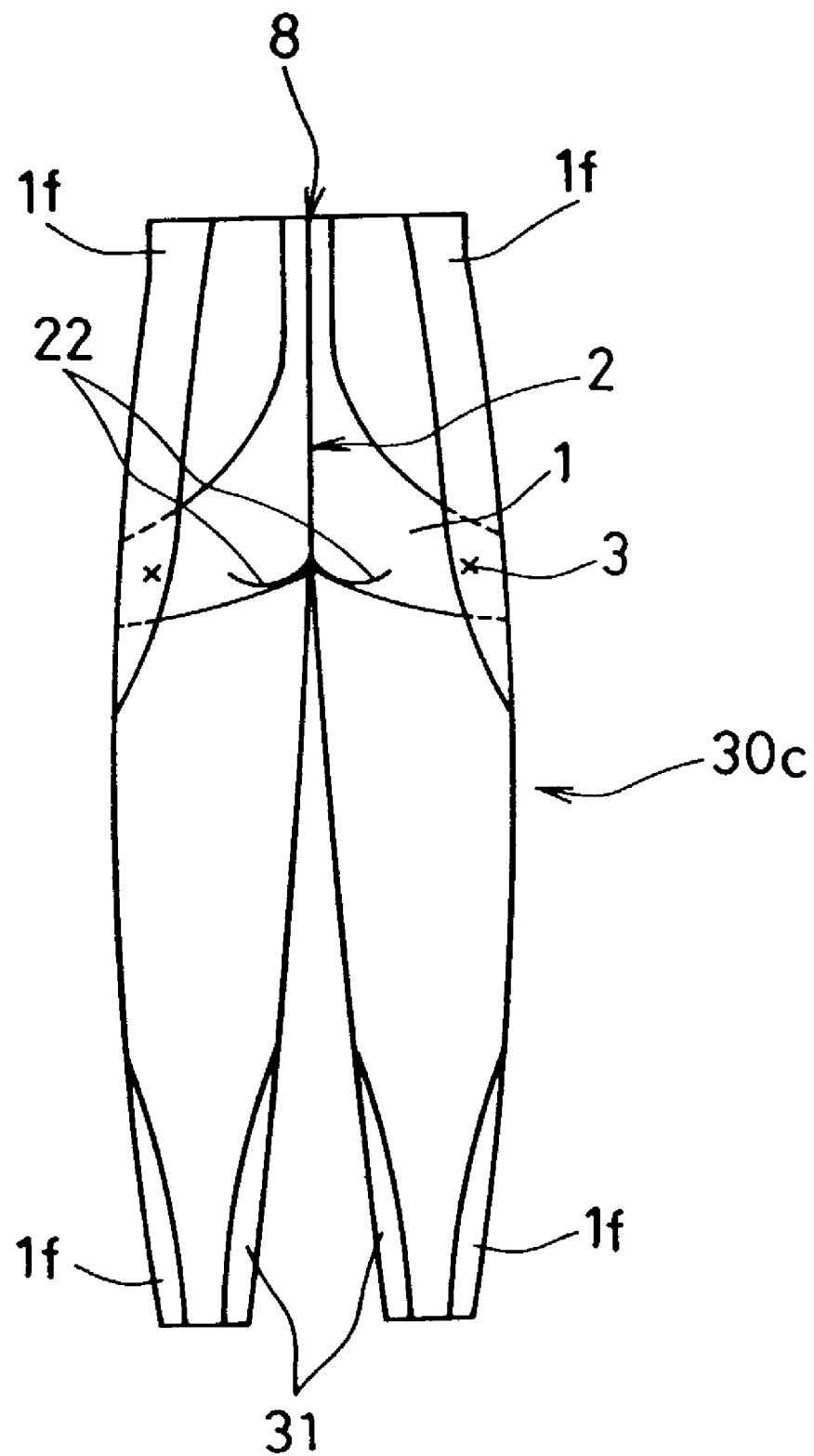
FIG. 40 is a rear view of still another embodiment of sports tights as a garment of the present invention.
Figure 41:
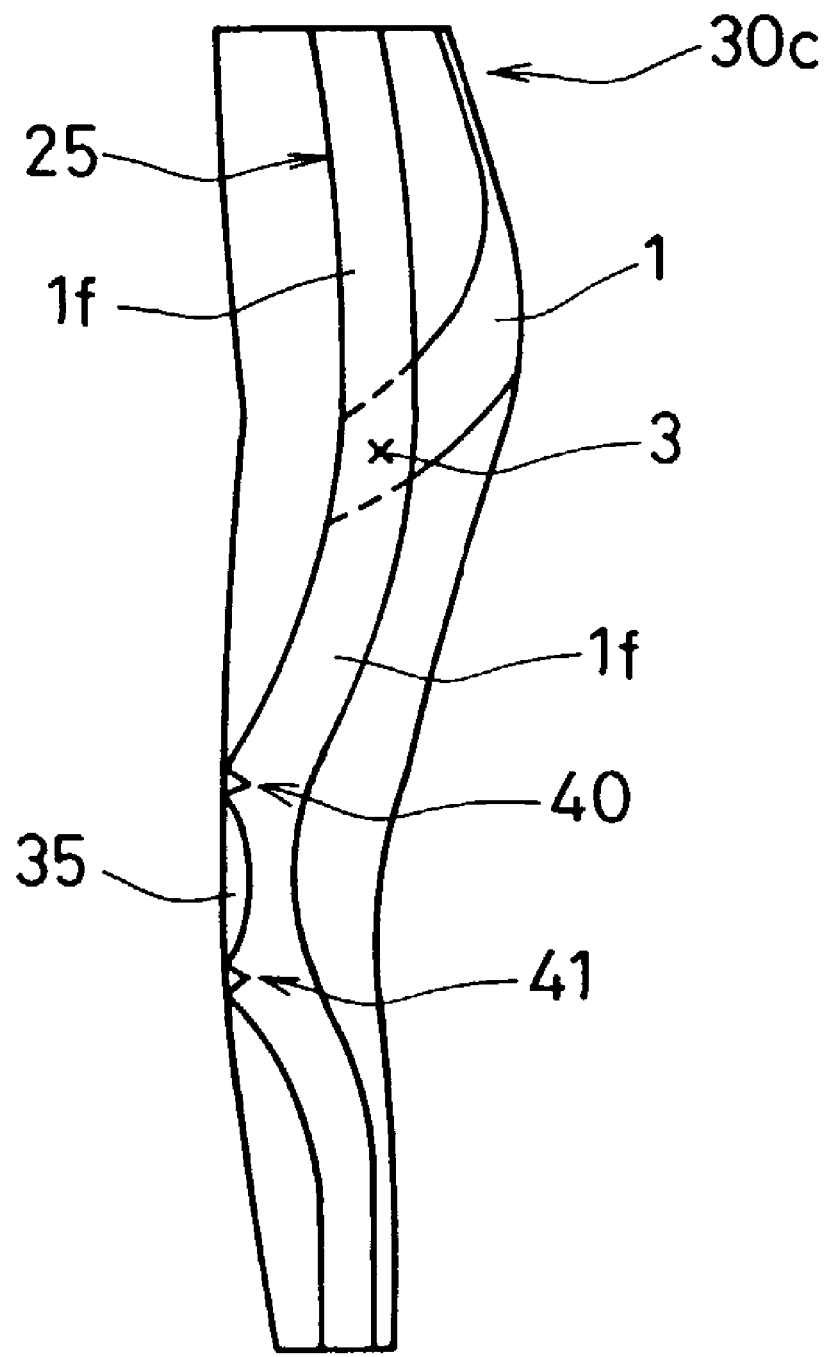
FIG. 41 is a left side view of the sports tights of FIG. 40.

FIGS. 40 to 41 show a rear view and a left side view of still another embodiment of sports tights as a garment of the present invention, respectively. The front view of the sports tights is approximately the same as FIG. 34 except that the strong straining portions 5 and 6 do not exist.

The sports tights 30c shown in FIGS. 40 to 41 has, as a strong straining portion (A), a strong straining portion 1 in which right and left parts are connected at a position 2 on the back side of the sports tights corresponding to the region from the fourth vertebra lumbalis to os sacrum of the wearer's body and which covers a region from the position 2 through the tops of the bulges of the buttocks or vicinities thereof in an approximately middle part of musculus gluteus maximus at right and left approximately in the direction of muscle fibers of musculus gluteus maximus to at least the vicinity of trochanter major 3. Furthermore, the sports tights 30c has a strong straining portion 1f that covers a region extending from a part corresponding to a side of the waist of the wearer's body to the vicinity of trochanter major 3 approximately in the direction of muscle fibers of musculus gluteus medius (this part is indicated by numeral 25), further from the vicinity of trochanter major 3 through the vicinity of tractus iliotibialis and musculus vastus lateralis approximately in the direction of their muscle fibers to a side of patella 35, and further from the side of patella 35 through the vicinity of musculus gastrocnemius and musculus soleus in regio cruris lateralis approximately in the direction of their muscle fibers to the vicinity of an upper part of malleolus lateralis so as to support musculus gastrocnemius and musculus soleus. Furthermore, in regio cruris medialis, in the same way as shown in FIG. 37, the sports tights 30c has a strong straining portion (E) 31 extending from regio femoralis medialis through musculus vastus medialis approximately in the direction of its muscle fibers to a side of patella 35 so as to support musculus vastus medialis, and further from the side of patella 35 through the vicinity of musculus gastrocnemius and musculus soleus in regio cruris medialis in the direction of their muscle fibers to the vicinity of an upper part of malleolus medialis so as to support musculus gastrocnemius and musculus soleus. Because the features in genu region are the same as those described with reference to FIG. 34, the same signs are applied to the same parts, and descriptions are omitted.

In the sports tights 30c shown in FIGS. 40 to 41, musculus gluteus maximus can be supported in the direction of its muscle fibers by the strong straining portion 1. Furthermore, musculus gluteus medius can be supported in the direction of its muscle fibers by the part in the strong straining portion 1f indicated by 25. Therefore, it can play a large role in extending the hip joint, particularly for the stability of the pelvis in anterior-posterior direction. It is effective in supporting a rotating motion of the hips, preventing a decrease in rotatable angle of the hips, and for an elderly person in preventing falling down. Furthermore, it can play a large role in extending the hip joint in anterior-posterior direction when running, jumping, and climbing up a slope. Furthermore, because the strong straining portions 1 and 1f cover the vicinity of trochanter major 3 from three directions, and the part in the strong straining portion 1f indicated by 25 pulls the force applied to trochanter major 3 upwardly approximately in a straight line, the joint between caput ossis femoris 204 and acetabulum can be improved further, and the stability of the hip joint can be increased. Furthermore, with the part lower than trochanter major 3 in the strong straining portion 1f and the strong straining portion (E) 31 in regio cruris medialis, when playing sports, the sports tights 30c exhibit the functions of generating a massage effect on the muscles supported by these strong straining portions and encouraging the recovery from fatigue of these muscles.

Figure 42:
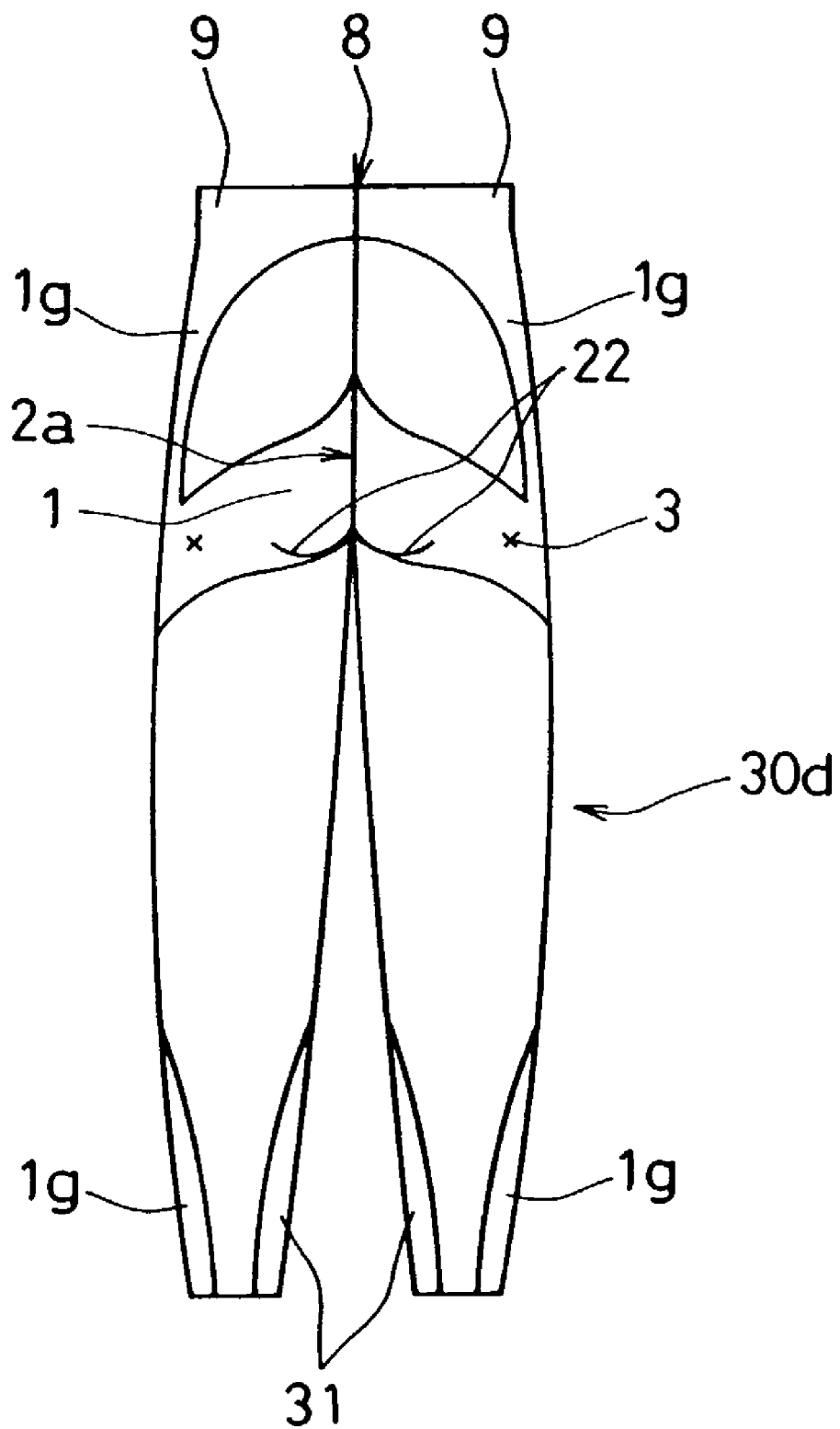
FIG. 42 is a rear view of still another embodiment of sports tights as a garment of the present invention.
Figure 43:
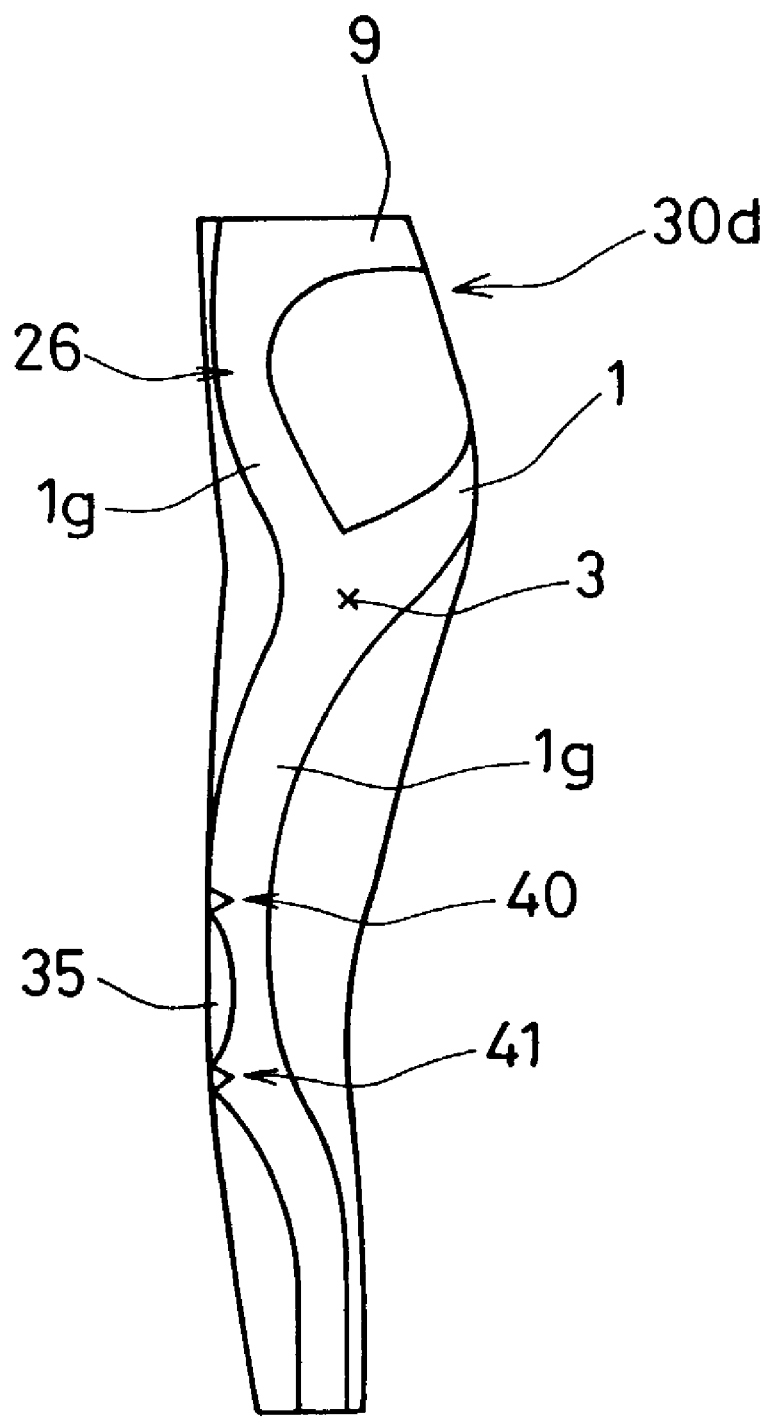
FIG. 43 is a left side view of the sports tights of FIG. 42.

Next, FIGS. 42 to 43 show a rear view and a left side view of still another embodiment of sports tights as a garment of the present invention, respectively. The front view of these sports tights is approximately the same as FIG. 34 except that the strong straining portions 5 and 6 do not exist. Comparing the sport tights 30d shown in FIGS. 42 to 43 with the sports tights 30c shown in FIGS. 40 to 41, main differences are as follows:

(1) In the sports tights 30c shown in FIGS. 40 to 41, right and left parts of the strong straining portion 1 are connected at the position 2 on the back side of the sports tights corresponding to the region from the fourth vertebra lumbalis to os sacrum of the wearer's body. On the other hand, in the sports tights 30d shown in FIGS. 42 to 43, right and left parts of the strong straining portion 1 are connected at the position 2a on the back side of the sports tights corresponding to os sacrum of the wearer's body.

(2) Comparing with the upper part 25 of the strong straining portion 1f in the sports tights 30c shown in FIGS. 40 to 41, an upper part 26 of the strong straining portion 1g in the sports tights 30d shown in FIGS. 42 to 43 is curved slightly toward the front side of the wearer's body, and covers musculus tensor faciae latae and a lateral part of musculus gluteus medius approximately in the direction of their muscle fibers.

(3) The sports tights 30d shown in FIGS. 42 to 43 further has, as a strong straining portion (D), a strong straining portion 9 in which right and left parts are connected approximately in the vicinity of the position 8 at the back center of the waist and which covers a region from the vicinity of the position 8 at the back center of the waist to musculus latissimus dorsi and musculus gluteus medius at right and left and a part of musculus obliquus externus abdominis. The strong straining portion 9 is united with the strong straining portion 1g.

Although there are some differences in the points (1) and (2) between the sports tights 30c and 30d, there are few differences in function based on the differences in these points, and these sports tights have approximately the same functions. However, because the sports tights 30d further has the strong straining portion 9 as described in (3), compared with the sports tights 30c, it further has the functions of preventing backward inclination of the pelvis and assisting to keep a stable position of the pelvis.

Figure 44:
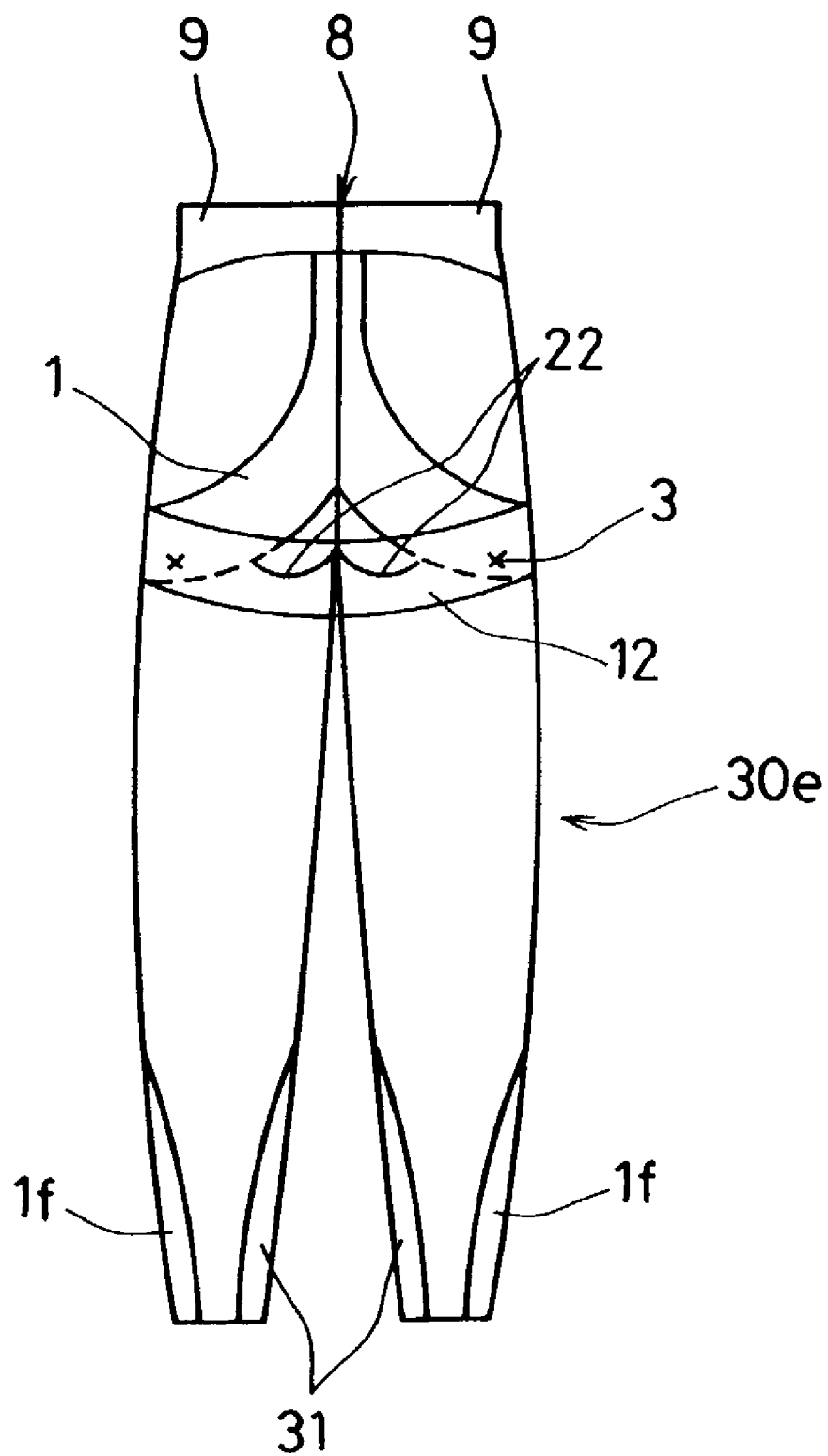
FIG. 44 is a rear view of still another embodiment of sports tights as a garment of the present invention.
Figure 45:
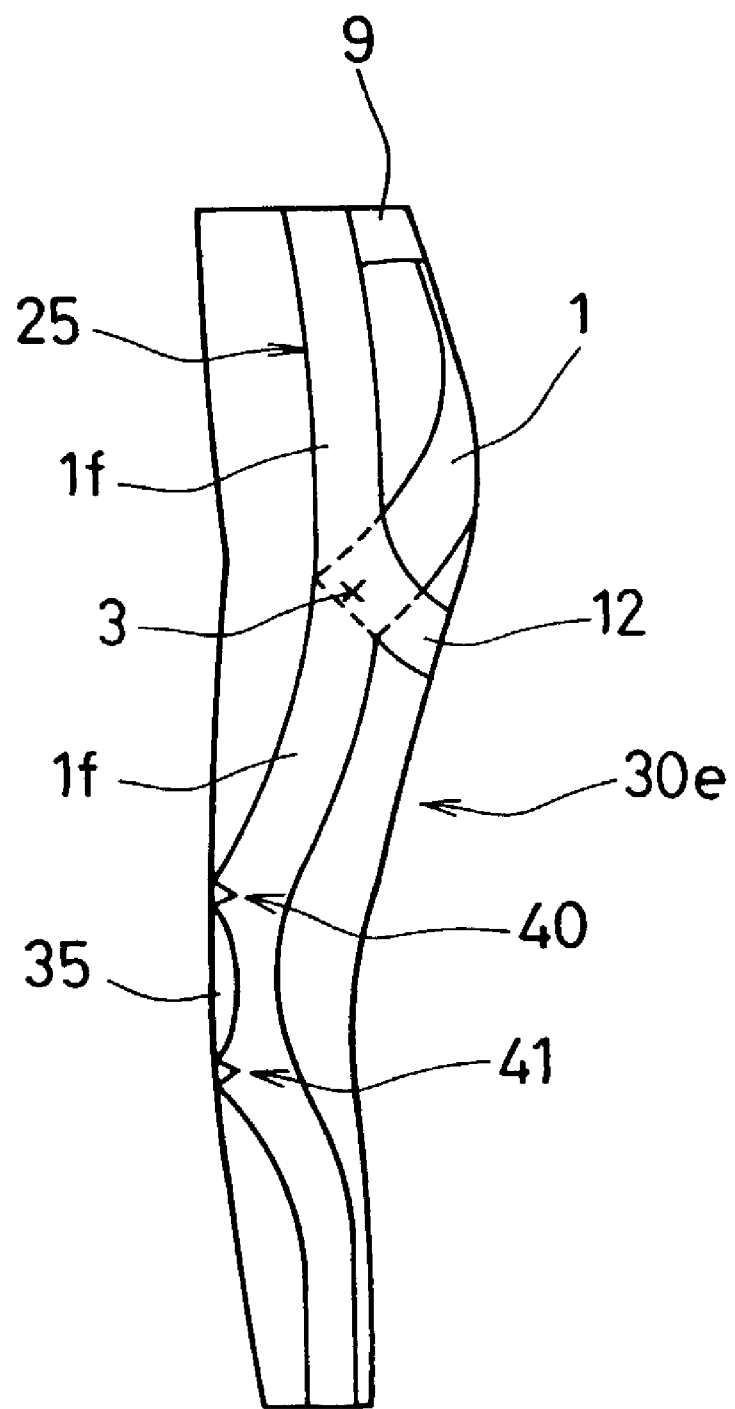
FIG. 45 is a left side view of the sports tights of FIG. 44.

Next, FIGS. 44 to 45 show a rear view and a left side view of still another embodiment of sports tights as a garment of the present invention, respectively. The front view of these sports tights is approximately the same as FIG. 34 except that the strong straining portions 5 and 6 do not exist. Comparing the sports tights 30e shown in FIGS. 44 to 45 with the sports tights 30c shown in FIGS. 40 to 41, main differences are as follows:

(1) The sports tights 30e shown in FIGS. 44 to 45 further has a strong straining portion 12 extending from the vicinity of trochanter major 3 through a lower part of the bulges of the buttocks.

(2) The sports tights 30e shown in FIGS. 44 to 45 further has, as a strong straining portion (D), a strong straining portion 9 in which right and left parts are connected approximately in the vicinity of a position 8 at the back center of the waist and which covers a region from the vicinity of the position 8 at the back center of the waist through musculus latissimus dorsi and musculus gluteus medius at right and left and a part of musculus obliquus externus abdominis. The strong straining portion 9 is connected to the upper end of the strong straining portion 1f.

Therefore, this sports tights 30e has the same functions as those of the sports tights 30c shown in FIGS. 40 to 41. In addition, because the sports tights 30e has the strong straining portion 12, its function of pressing trochanter major 3 is enhanced further, and is functions of improving the joint between caput ossis femoris 204 and acetabulum and increasing the stability of the hip joint are enhanced further. Furthermore, this strong straining portion 12 can provide the function of keeping the bulges of the hips in a high position. Furthermore, because the sport tights 30e has the strong straining portion 9, and the strong straining portion 9 is connected to the upper end of the strong straining portion 1f, compared with the sports tights 30c, the sports tights 30e further has the functions of preventing backward inclination of the pelvis and assisting to keep a stable position of the pelvis.

Figure 46:
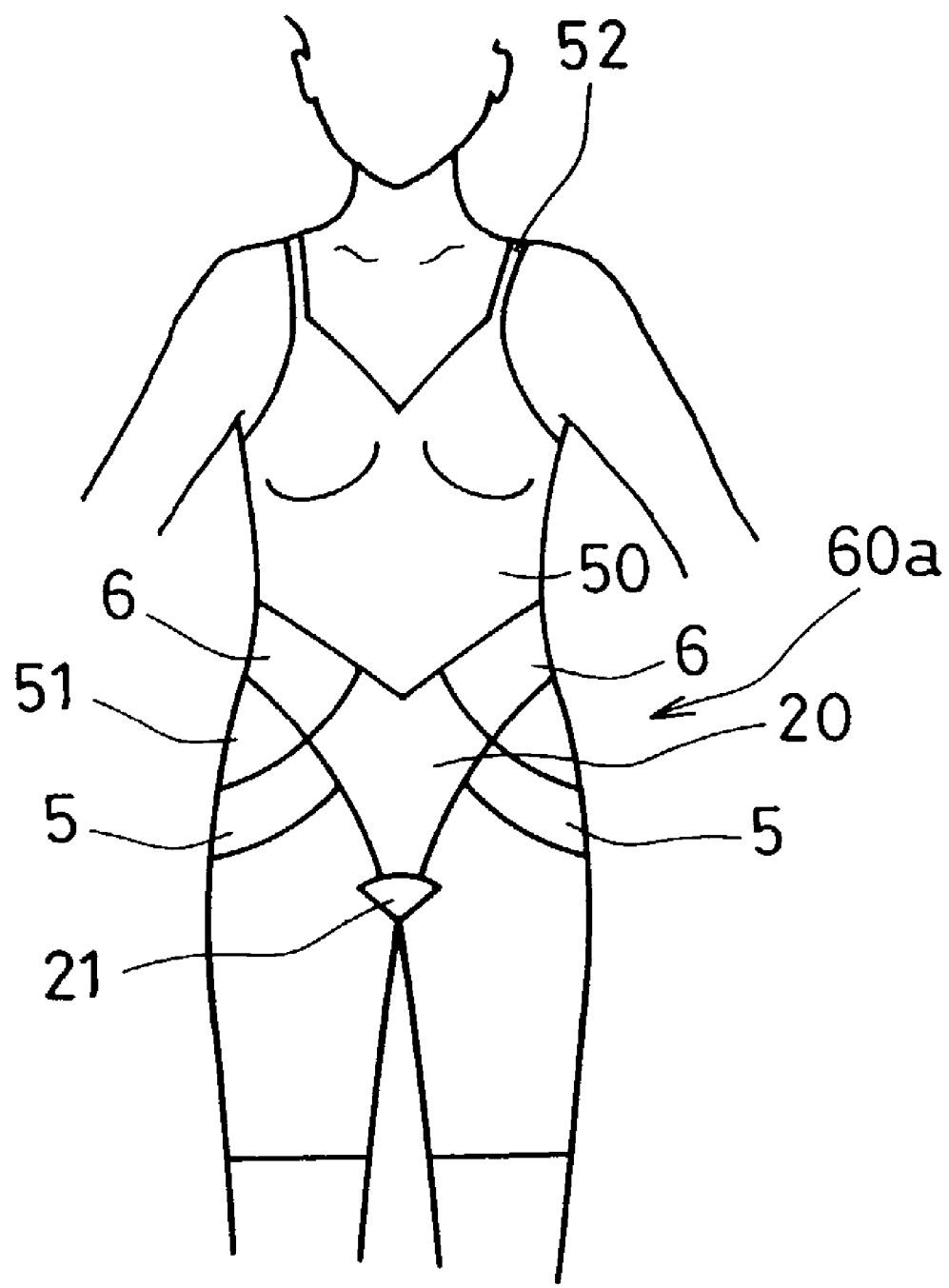
FIG. 46 is a front view of a bodysuit as a garment of the present invention in wearing condition.
Figure 47:
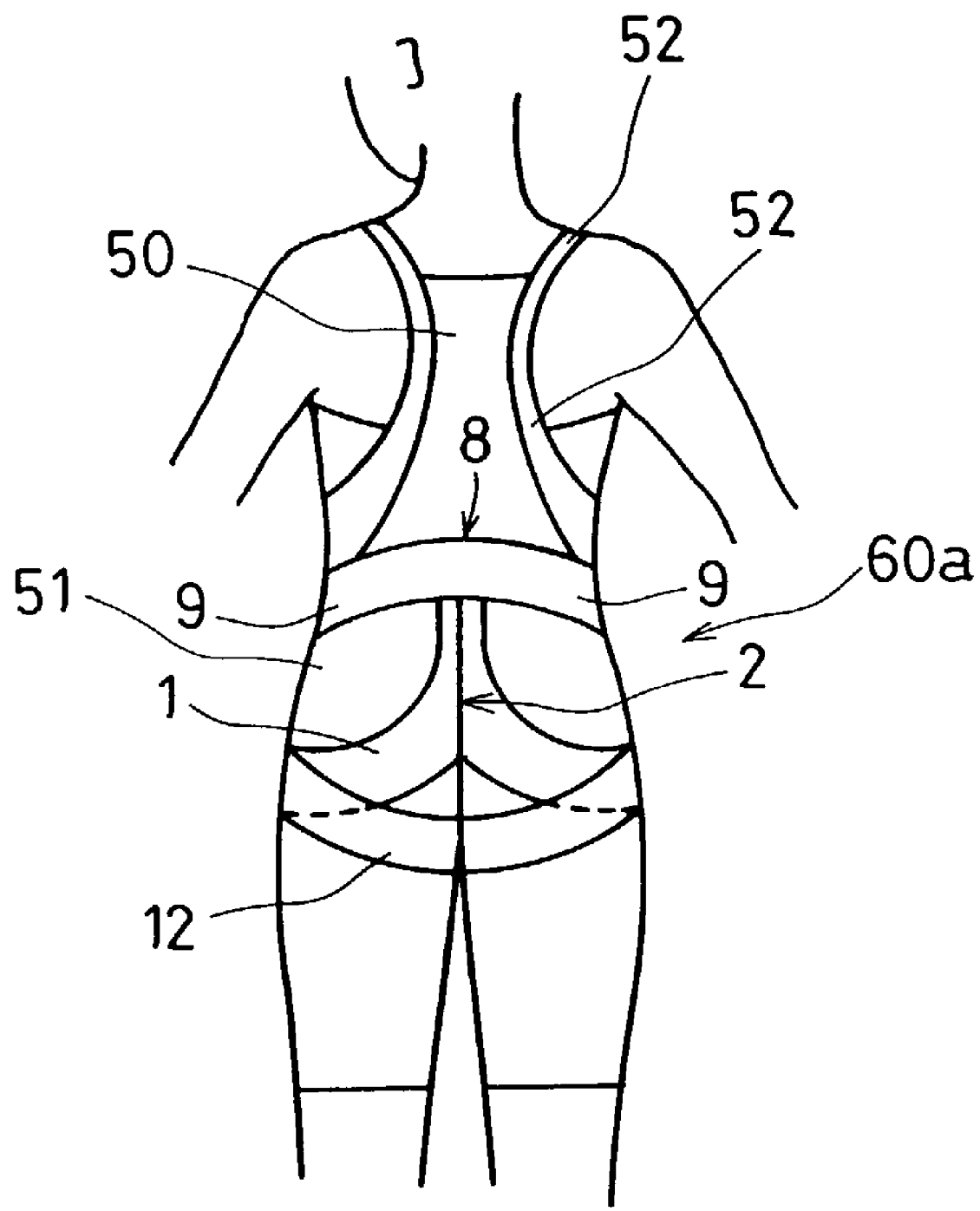
FIG. 47 is a rear view of the bodysuit of FIG. 46 in wearing condition.
Figure 48:
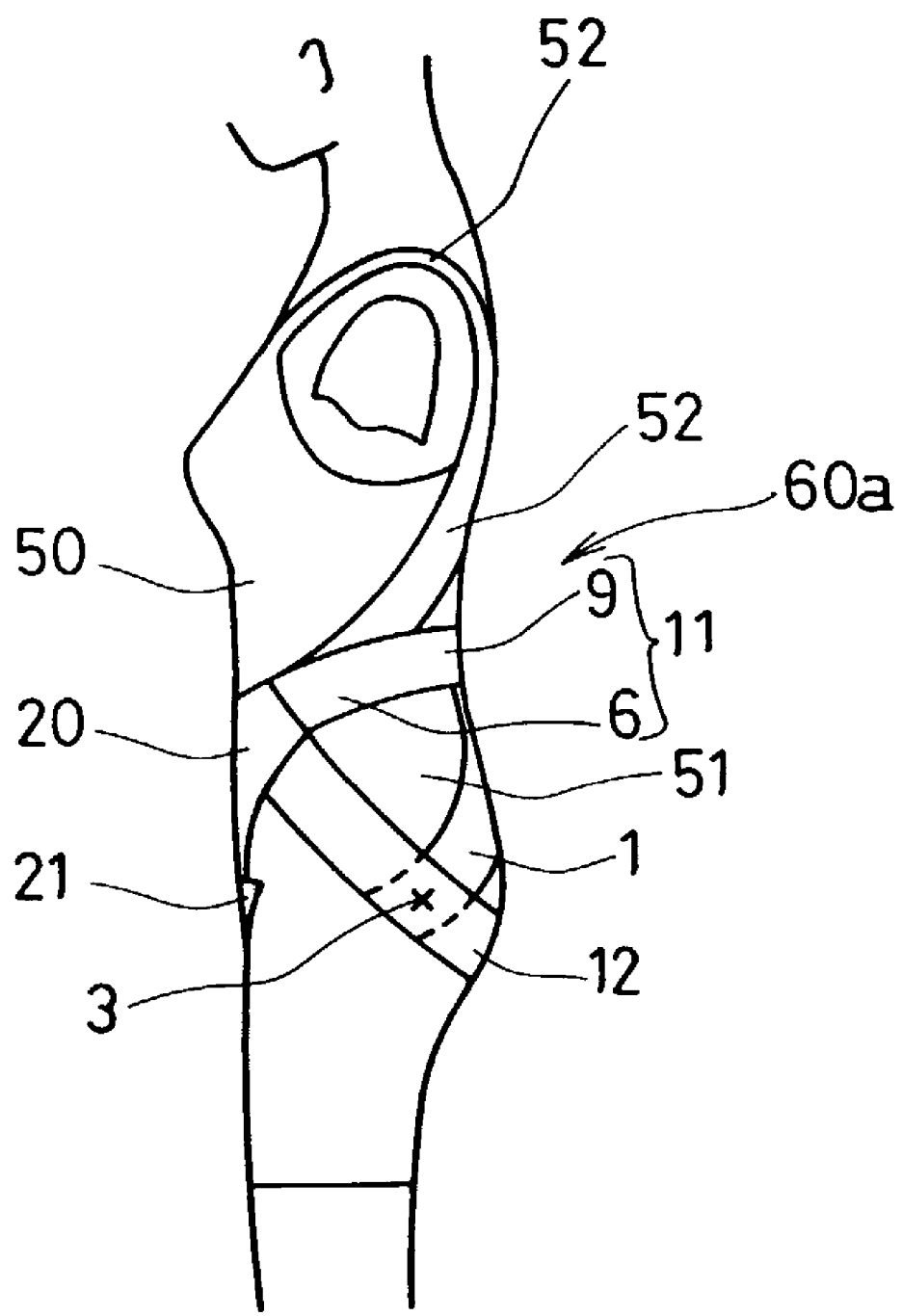
FIG. 48 is a left side view of the bodysuit of FIG. 46 in wearing condition.

Next, FIGS. 46 to 48 show a front view, a rear view and a left side view of a bodysuit as a garment of the present invention in wearing condition, respectively.

In the bodysuit 60a shown in FIGS. 46 to 48, the upper body section is indicated by numeral 50, and the lower body section is indicated by numeral 51. This bodysuit 60a is of the type in which the lower body section 51 has a relatively long length to the lower end. The upper body section has cloth pieces 52 covering a part of the back region of the wearer while serving as straps. The arrangement of each strong straining portion in the lower body section 51 is substantially the same as that in the girdle 10g shown in FIGS. 19 to 21. Therefore, the same signs are applied to the same parts as in the girdle 10g, and descriptions thereof are omitted. Thus, this bodysuit 60a can display substantially the same functions as in the case of the girdle 10g shown in FIGS. 19 to 21.

Figure 49:
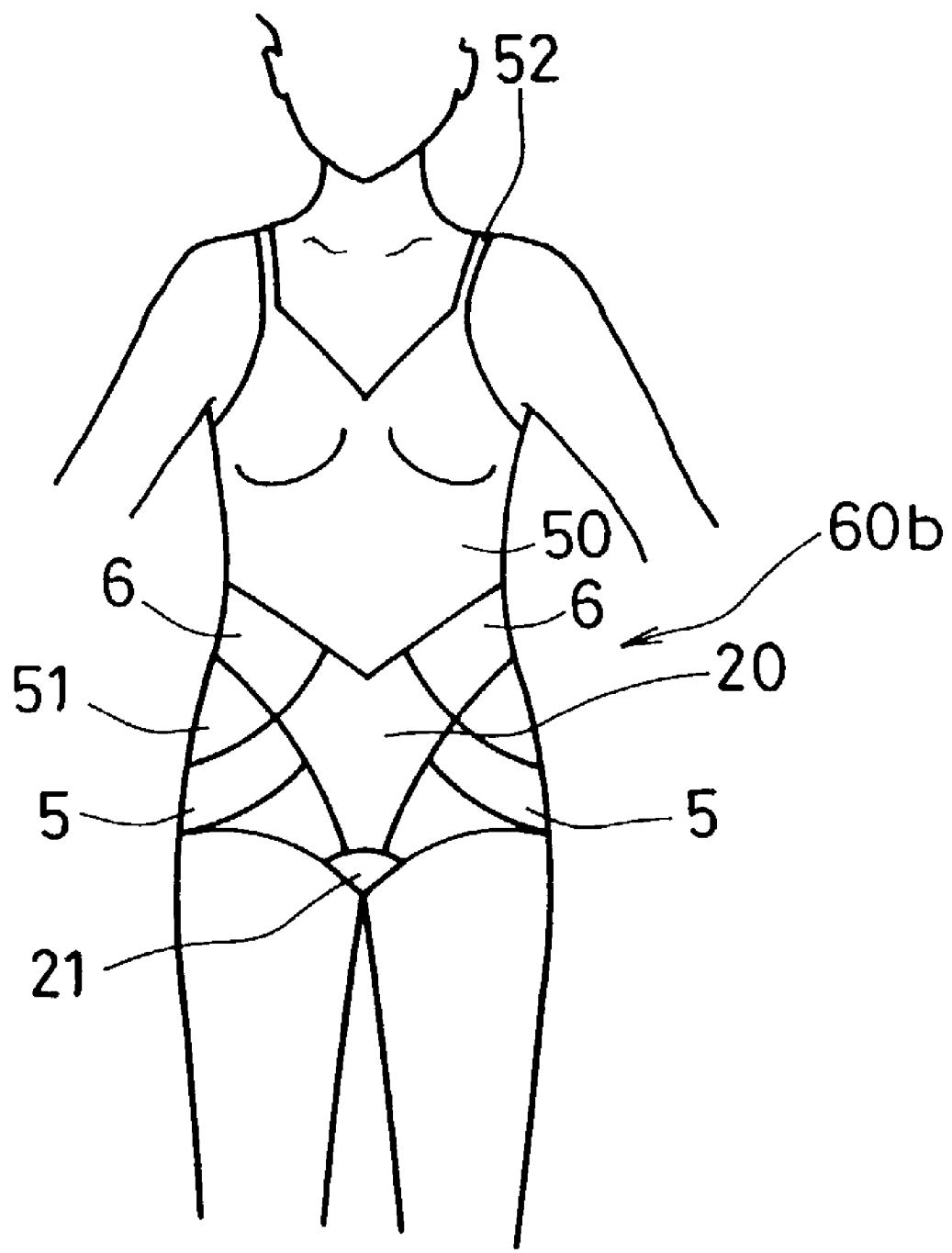
FIG. 49 is a front view of still another embodiment of a bodysuit as a garment of the present invention in wearing condition.
Figure 50:
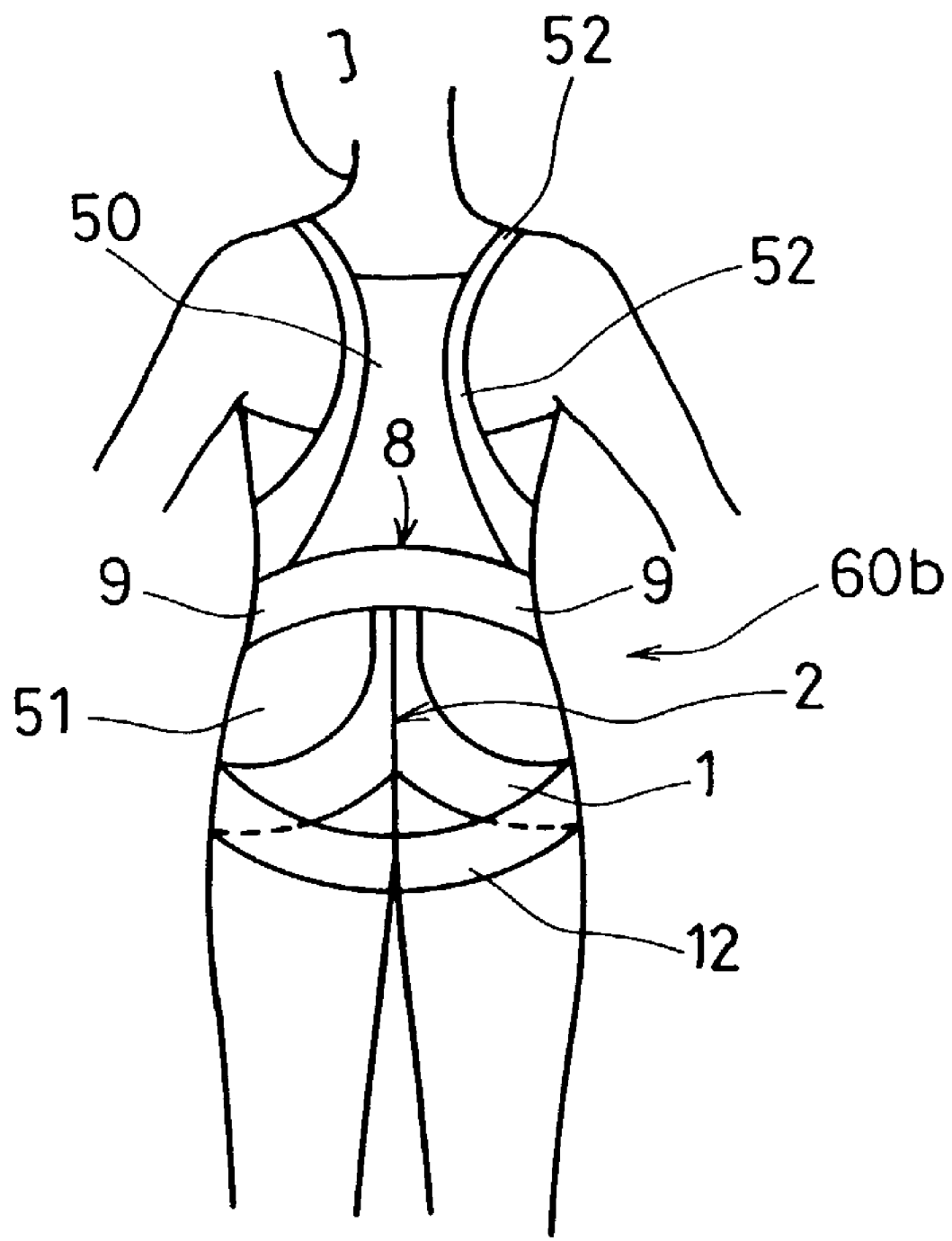
FIG. 50 is a rear view of the bodysuit of FIG. 49 in wearing condition.
Figure 51:
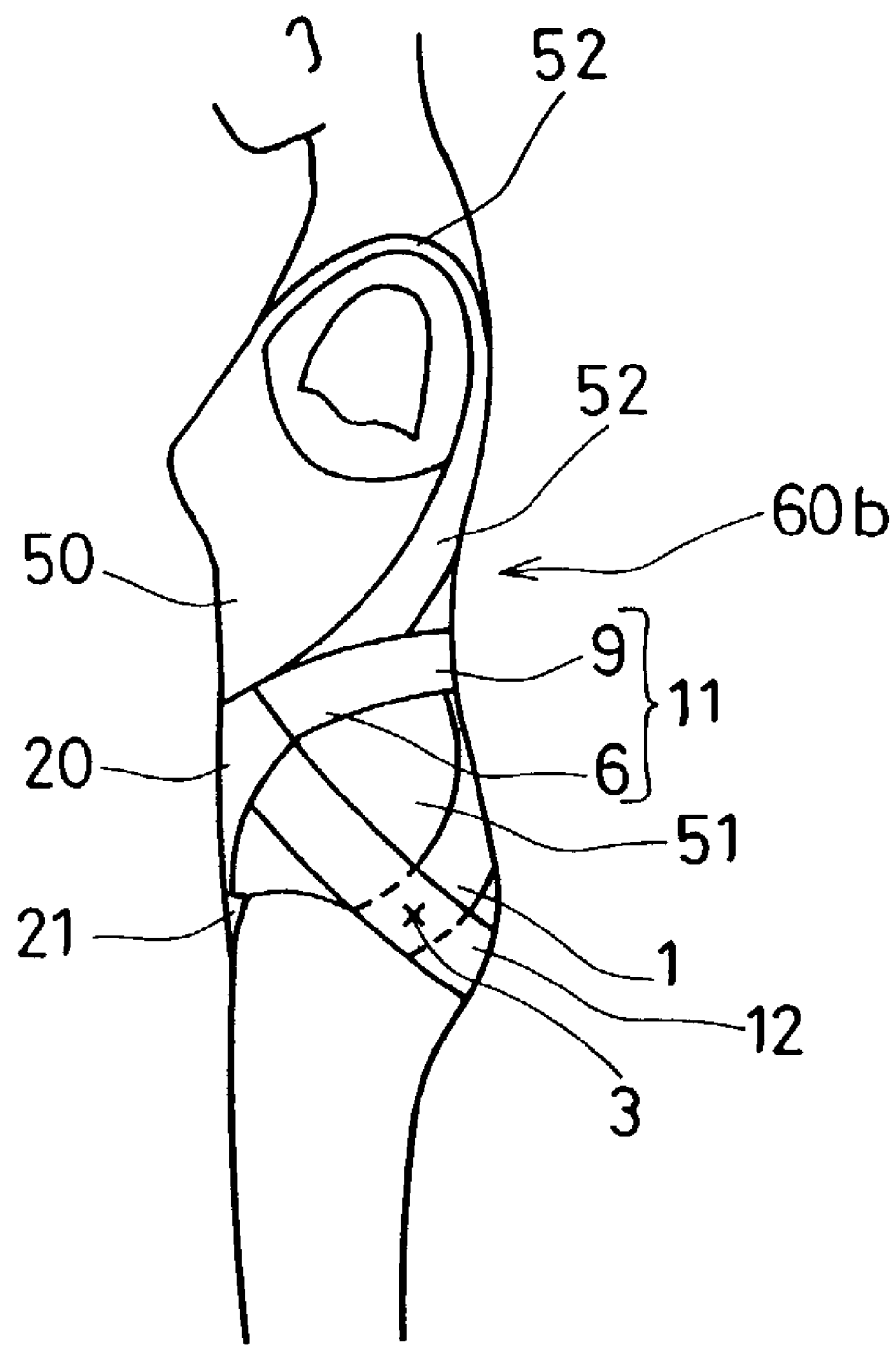
FIG. 51 is a left side view of the bodysuit of FIG. 49 in wearing condition.

Next, FIGS. 49 to 51 show a front view, a rear view and a left side view of still another embodiment of a bodysuit as a garment of the present invention in wearing condition, respectively.

The bodysuit 60b is different from the bodysuit 60a shown in FIGS. 46 to 48 only in that while the bodysuit 60a shown in FIGS. 46 to 48 is of the type in which the lower body section 51 has a relatively long length to the lower end, the bodysuit 60b shown in FIGS. 49 to 51 is of the type in which the lower body section 51 has a short length to the lower end. They are substantially the same in other parts. Therefore, the same signs are applied to the same parts as in the bodysuit 60a shown in FIGS. 46 to 48, and descriptions thereof are omitted. Thus, this bodysuit 60b can display substantially the same functions as in the bodysuit 60a shown in FIGS. 46 to 48.

Next, an example of a garment formed by knitting strong straining portions and weak straining portions in predetermined patterns differently by changing stitches is shown.

In the following example, an embodiment is described for each of a long type girdle (FIGS. 52 to 54) and a short type girdle (FIGS. 55 to 57) among garments formed by knitting different portions with four grades of straining forces: that is, three types of strong straining portions, namely, a strong straining portion with most strong straining force (hereinafter referred to as the first strong straining portion); a portion with second most strong straining force (hereinafter referred to as the second strong straining portion); and a portion with third most strong straining force (hereinafter referred to as the third strong straining portion), which has a straining force weaker than that of the second strong straining portion but is stronger than that of a weak straining portion; and other portions as a weak straining portion.

Figure 52:
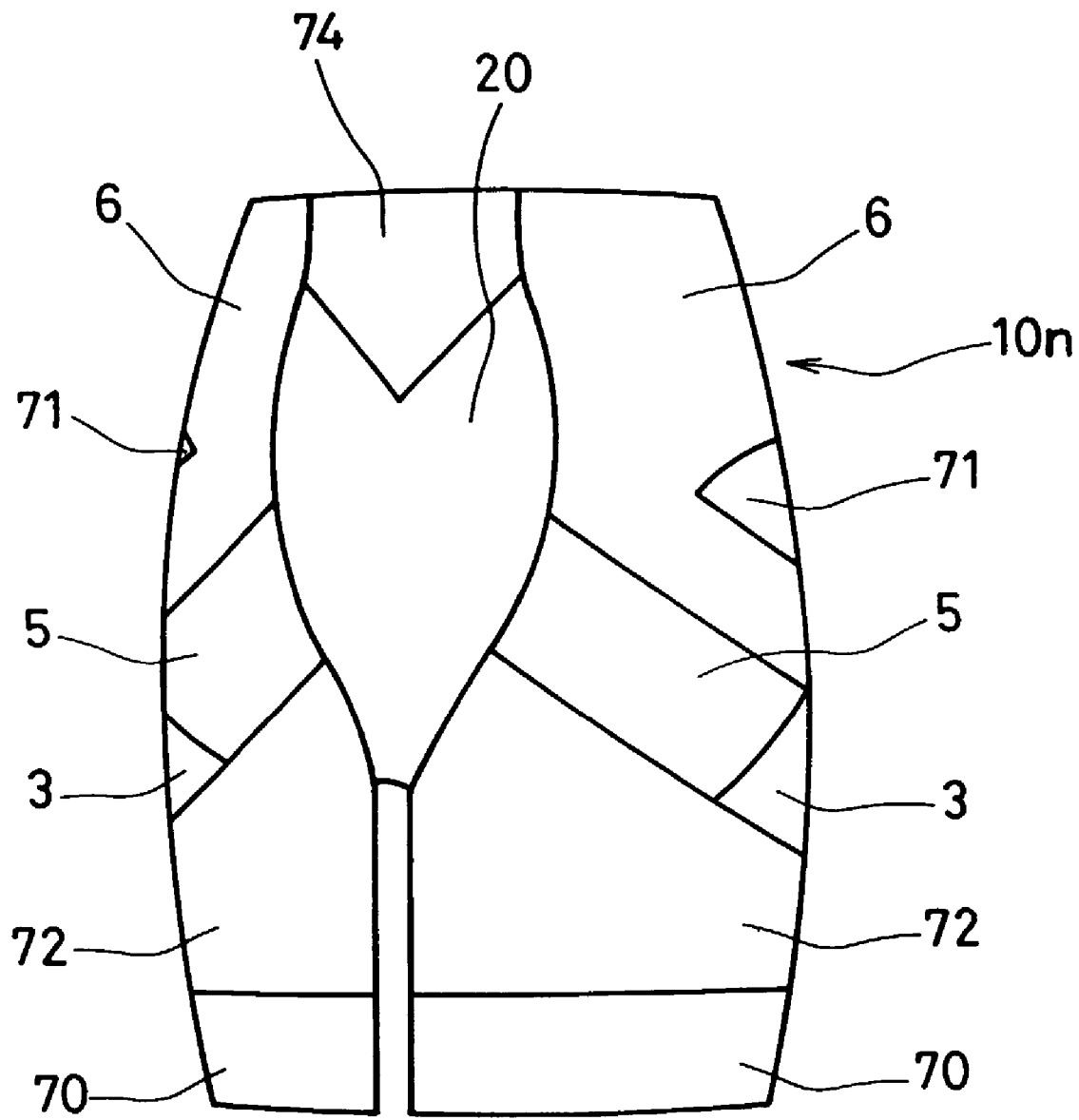
FIG. 52 is a perspective view of a long type girdle of the present invention from the front side.
Figure 53:
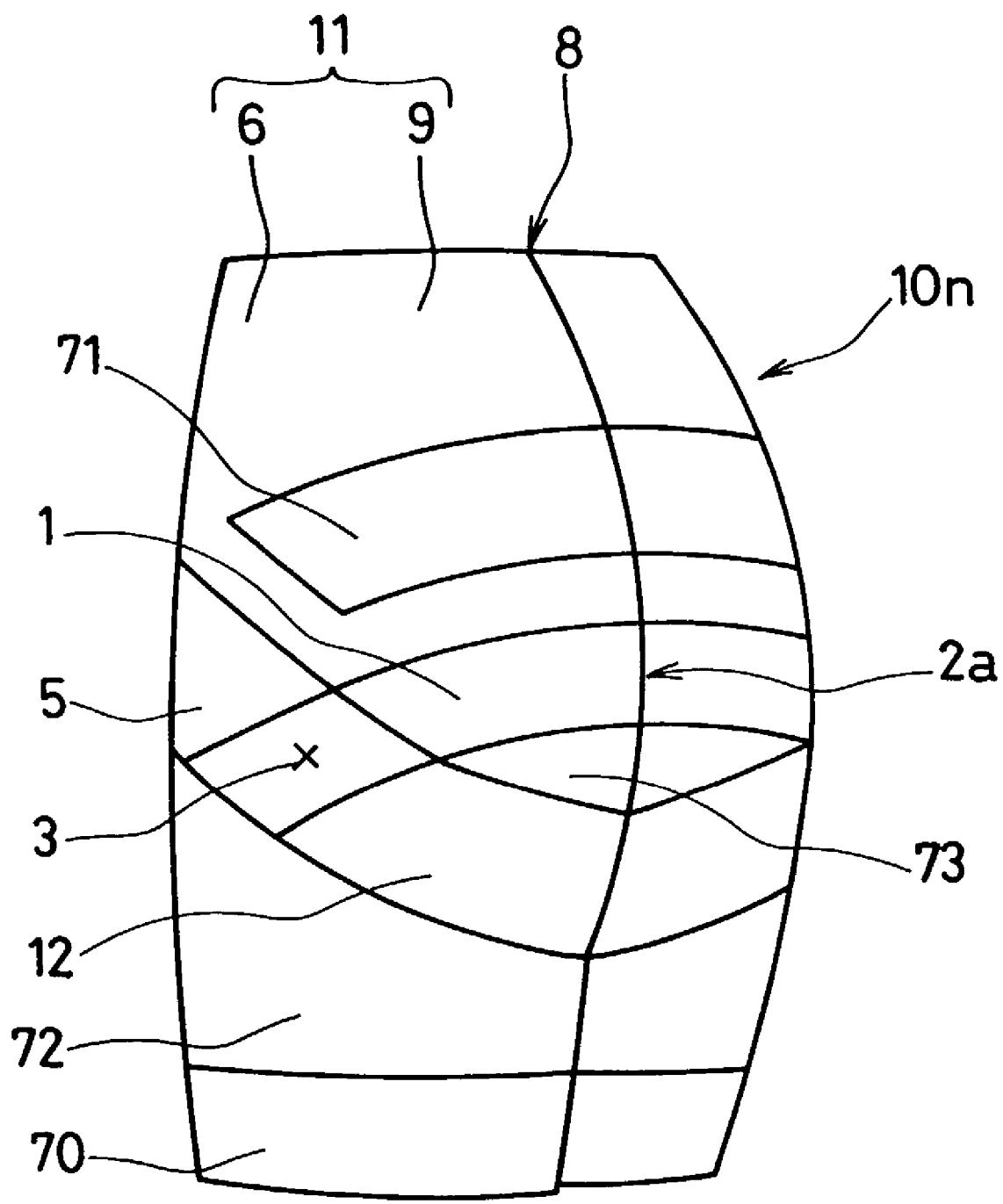
FIG. 53 is a perspective view of the long type girdle of FIG. 52 from the rear side.

FIG. 52 is a perspective view of a long type girdle of the present invention from the front side; FIG. 53 is a perspective view thereof from the rear side; and FIG. 54 is a plan view of a fabric used for a part from the back to the side front and a leg part of this girdle before cutting.

Figure 54:
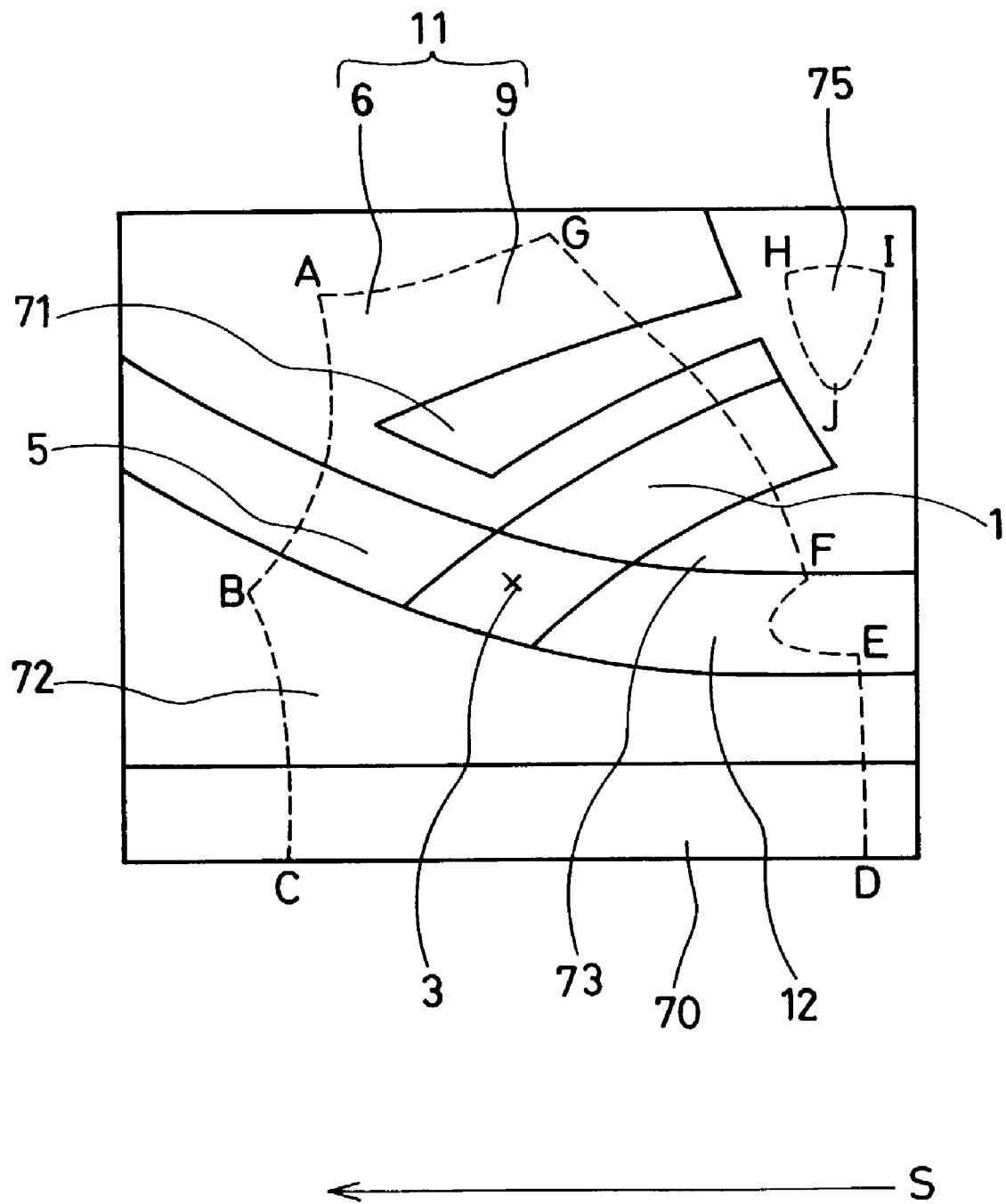
FIG. 54 is a plan view of a fabric used for a part from the back to the side front and a leg part of the girdle shown in FIGS. 52 to 53 before cutting.

The long type girdle 10n shown in FIGS. 52 to 54 is relatively similar to the girdle 10g shown in FIGS. 19 to 21. When compared, in the girdle 10g shown in FIGS. 19 to 21, right and left parts of the strong straining portion 1 are connected at the position 2 on the back side of the girdle corresponding to from the fourth vertebra lumbalis to os sacrum of the wearer's body. On the other hand, in the girdle 10n shown in FIGS. 52 to 54, right and left parts of the strong straining portion 1 are connected at the position 2a on the back side of the girdle corresponding to os sacrum of the wearer's body. Furthermore, in the girdle 10n shown in FIGS. 52 to 54, a strong straining portion 6 is bent downward at the sides of a strong straining portion (F) for pressing abdomen, and further extends along the upper sides of strong straining portions 5 and 1. Furthermore, in the girdle 10n shown in FIGS. 52 to 54, strong straining portions 70 further exist at lower ends. Because other points are substantially the same as those in the long type girdle 10g shown in FIGS. 19 to 21, the same signs are applied to the same parts, and detailed descriptions are omitted.

Furthermore, this long type girdle was formed by knitting and differentiating the strong straining portions into four grades of the first strong straining portion, the second strong straining portion, the third strong straining portion, and the weak straining portion as described above. The knitting of these different portions may use any stitch, and any method of knitting that can adjust the knitted density or the tension of yarn may be employed. In this embodiment, four grades of the first strong straining portion, the second strong straining portion, the third strong straining portion and the weak strong straining portion as described above were differentiated by changing the stitch appearing on the front side of a warp knitted fabric by jacquard knitting, which can knit a portion with a relatively strong straining force with a stronger straining force than circular knitting, and has good appearance and is resistant to fraying due to a run, etc.

That is, the ground knitted fabric formed by jacquard knitting comprises a warp knitted fabric knitted with an inelastic yarn using an elastic yarn as insert yarn. By changing the stitch appearing on the front side of the ground knitted fabric depending on the requirement of the strength of the straining force thereby to form predetermined portions with relatively strong straining forces and relatively weak straining forces in patterns in predetermined parts, different portions with desired straining forces can be knitted at predetermined positions in predetermined patterns depending on the requirement of the strength of straining forces.

In this embodiment, knitting was carried out by varying power net stitches as described above. The first strong straining portion, the second strong straining portion, and the third strong straining portion were knitted with respective satin-like net stitches, and the weak straining portion was knitted with a mesh-like net stitch.

This ground knitted fabric can be produced, for example, by the method as follows: using a warp knitting machine having a jacquard control apparatus (for example, see U.S. Pat. No. 5,390,512 (corresponding to JP 6(1994)-166934 A)), or specifically, a high-speed jacquard raschel machine "RSJ 4/1" having deflecting transducers mounted to yarn guide bars, which is manufactured by Karl Mayer Textilmaschinenfabrik GmbH (marketed by Japan Mayer Ltd.), commands are inputted into the computer of the warp knitting machine having a jacquard control apparatus so that predetermined stitches are formed at predetermined positions with respect to each wale and each course.

In this embodiment, the strong straining portions were differentiated into three grades of the first strong straining portion, the second strong straining portion and the third strong straining portion by having a racking of at least two needles (two needles in this case) in a large, medium or small proportion in one repeat knitted unit. A racking of two needles can be accomplished by the method as follows: when knitting a wale, (1) the stitch is racked to the adjacent wale, (2) and then the stitch is returned to the original wale. The straining force of a strong straining portion can be enhanced further by having more of above (1) and (2) in one repeat knitted unit. Furthermore, in this embodiment, a mesh-like net stitch having a larger space and a lower density of yarn per unit than a satin-like net stitch was used in the weak straining portion.

Such knitting of different portions is described in detail, for example, in WO99/53779, which can be referenced if necessary.

In this embodiment, as the yarn forming the ground knitted fabric, a nylon yarn of 20 denier was used for both the yarn appearing on the front side and the yarn appearing on the back side. As insert yarn, one polyurethane elastic yarn of 280 denier and one polyurethane elastic yarn of 40 denier were used for each wale. The polyurethane elastic yarn of 40 denier was inserted while winding with respect to the wale direction, in other words, to reach a plurality of wales so that stretchability was expressed in two directions, namely, not only in the wale direction, but also in the course direction in perpendicular to the wale direction. The polyurethane elastic yarn of 280 denier was inserted approximately on the same wale, and contributes mainly to the stretchability in the wale direction. Regardless of the change in the stitch appearing on the front side of the ground knitted fabric, these polyurethane elastic yarns were inserted approximately uniformly in the entire ground knitted fabric by the above-described method and proportion. The ratio of the nylon yarn and the polyurethane elastic yarns used in the entire fabric was 80 wt. % of the nylon yarn to 20 wt. % of the polyurethane elastic yarns.

The long type girdle shown in FIGS. 52 to 53 has, as a strong straining portion (A), the strong straining portion 1 in which right and left parts are connected at the position 2a on the back side of the girdle corresponding to os sacrum of the wearer's body and which covers a region from the position 2a through the tops of the bulges of the buttocks or vicinities thereof in an approximately middle part of musculus gluteus maximus at right and left approximately in the direction of muscle fibers of musculus gluteus maximus to at least the vicinity of trochanter major 3. In the strong straining portion 1, the section corresponding to the region where trochanter major 3 is present is formed of the first strong straining portion having a racking of two needles in a large proportion, and the strong straining portion 1 other than the section corresponding to the region where trochanter major 3 is present is formed of the second strong straining portion having a racking of two needles in a medium proportion. The strong straining portion (F) indicated by numeral 20 for pressing abdomen at the center of hypogastric region is formed of the second strong straining portion.

The strong straining portion 5 connected to right and left slightly lower sides of the strong straining portion (F) 20 and the strong straining portion 12 connected to the strong straining portion 5 through the section corresponding to the region where trochanter major 3 is present are united to form a strong straining portion (B2). Other than the section corresponding to the region where trochanter major 3 is present, the strong straining portions 5 and 12 are formed of the second strong straining portion.

Furthermore, the strong straining portions 6 as one embodiment of the strong straining portion (C), and the portion indicated by the strong straining portion 9 as the strong straining portion (D) that covers the waist region at the rear of the strong straining portion 6 integrally are formed of the third strong straining portion. The strong straining portions 70 at the lower ends of the girdle are formed of the second strong straining portion.

Other parts, namely, an upper part of the buttocks indicated by 71, parts of leg regions indicated by 72, a part a little higher than gluteal cleft at right and left indicated by 73, and an upper part of the abdomen indicated by 74 are formed of a mesh-like net stitch as the weak straining portion.

This girdle also has, as a strong straining portion (A), the strong straining portion 1 in which right and left parts are connected at the position 2a on the back side of the girdle corresponding to os sacrum of the wearer's body and which covers the region from the position 2a through the tops of the bulges of the buttocks or vicinities thereof in an approximately middle part of musculus gluteus maximus at right and left approximately in the direction of muscle fibers of musculus gluteus maximus to at least the vicinity of trochanter major 3. Therefore, musculus gluteus maximus can be supported firmly in the direction of its muscle fibers. Thus, it can play a large role in supporting the rotating motion of the hips, preventing a decrease in the rotating angle of the hips, and stabilizing the pelvis in anterior-posterior direction. For an elderly person, it is effective in preventing falling down. Furthermore, it can play a large role in extending the hip joint in anterior-posterior direction when running, jumping, and climbing up a slope.

Furthermore, the portion indicated by the strong straining portion 5 is united with the strong straining portion 12 extending further from the vicinity of trochanter major 3 to a lower part of the bulges of the buttocks to form a strong straining portion (B2). Thus, in this girdle, because of the presence of the strong straining portion (B2), the function of pressing trochanter major 3 is enhanced further, and the functions of improving the joint between caput ossis femoris 204 and acetabulum and increasing the stability of the hip joint are enhanced further. Furthermore, with the strong straining portion 12, the function of keeping the bulges of the hips in a high position can be provided.

Furthermore, because right and left parts of the strong straining portion 5 and right and left parts of the strong straining portion 6 are connected to each other through the strong straining portion (F) 20, the functions of supporting abdominal muscles more strongly, reducing lumbar lordosis, maintaining good posture, making youthful figure, and preventing generation of pains such as lumbar pains can be displayed more easily. Furthermore, because the strong straining portions 6 and 9 are united to form the strong straining portion 11, the functions of supporting the region from the vicinity of the position 8 at the back center of the waist through musculus latissimus dorsi 308 and musculus gluteus medius 309 at right and left and musculus obliquus externus abdominis 302 more strongly, preventing backward inclination of the pelvis, and keeping a stable position of the pelvis are displayed more easily.

Furthermore, because the strong straining portions 70 at the lower ends are formed of the second strong straining portion, sliding-up of the lower ends can be prevented. Because these portions press the thighs in the form of a sheet, compared with the case in which a rubber tape or the like is attached to the lower ends, the thighs are not compressed linearly to cut into flesh, and it has excellent wearing comfort.

Moreover, in this girdle, because the strong straining portions are not formed by lining with a cloth or the like but are formed by changing stitches, there is substantially no difference in level at a boundary between strong straining portions and weak straining portions. Therefore, there is no possibility that such a difference in level at the boundary is reflected into an outer wear and appears on the outer wear, deteriorating the appearance of the wearer.

FIG. 54 is a plan view of a fabric used for a part from the back to the side front and a leg part of this girdle before cutting. The section enclosed by a broken line A-B-C-D-E-F-G-A indicates a cutting line of a body fabric (fabric for covering) for the region from the front to the back on the right side other than the strong straining portion 20 and the upper abdomen part 74 in FIG. 52. The section 75 enclosed by a broken line H-I-J is a cutting line of a piece corresponding to the crotch. The G-F line is the center line at the back of the girdle. Because the same signs are applied to the same parts in FIG. 54 as in FIGS. 52 and 53, it is easy to understand which of the respective parts shown in FIG. 54 constitutes any part in FIGS. 52 and 53. In FIG. 54, the direction in which the yarn forming this jacquard raschel warp knitted fabric is supplied, namely, the wale direction, is indicated by an arrow S.

The girdle shown in this embodiment is comprised of a total of four fabrics, namely, two for right and left body sides of the fabric shown in FIG. 54, which is used for a part from the back to the side front and a leg part of the girdle; the crotch cloth piece indicated by 75; and an abdomen cloth in which the upper abdomen part 74 and the strong straining portion (F) 20 for pressing abdomen in FIG. 52 are knitted differently and united.

Figure 55:
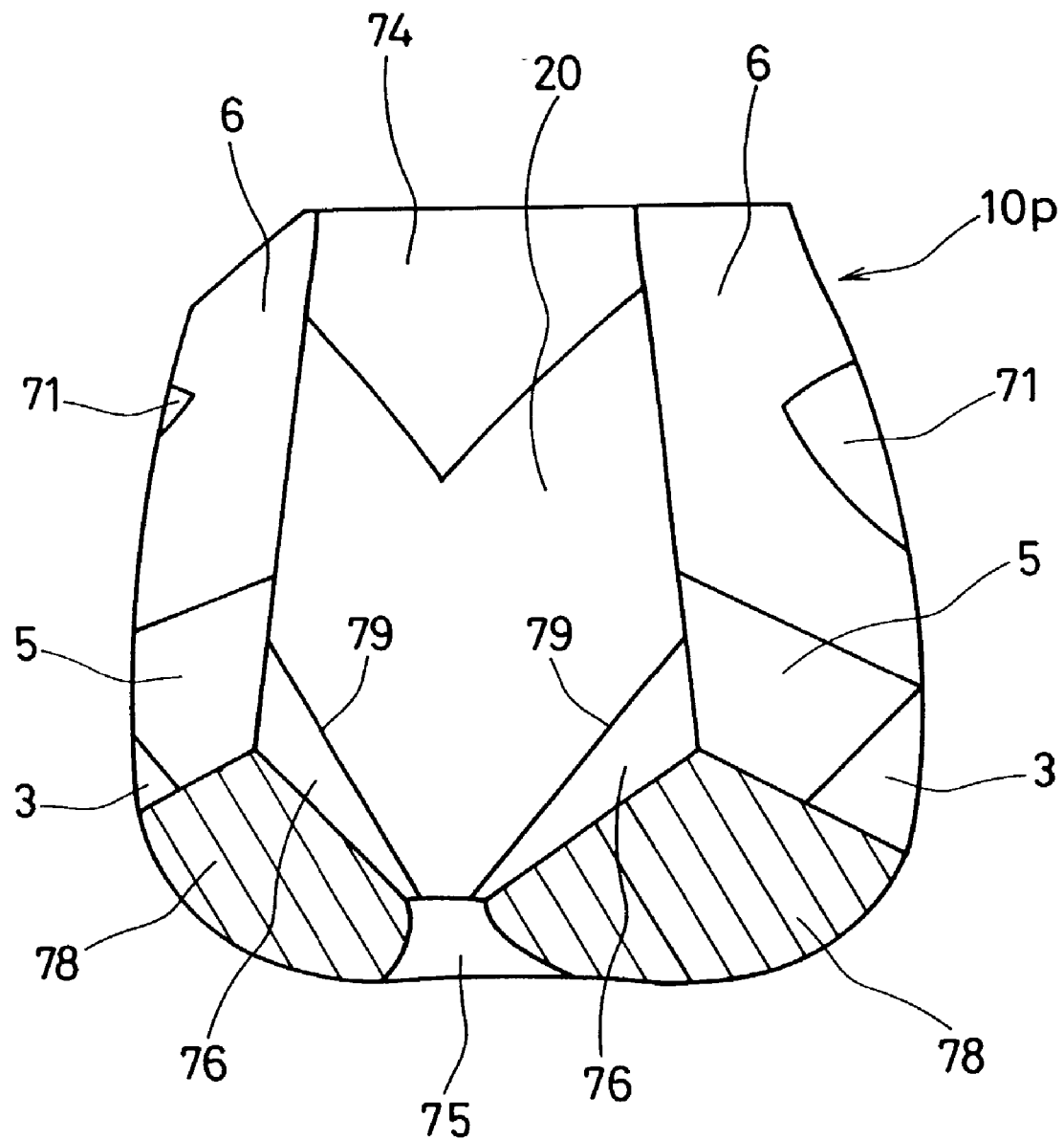
FIG. 55 is a perspective view of a short type girdle of the present invention from the front side.
Figure 56:
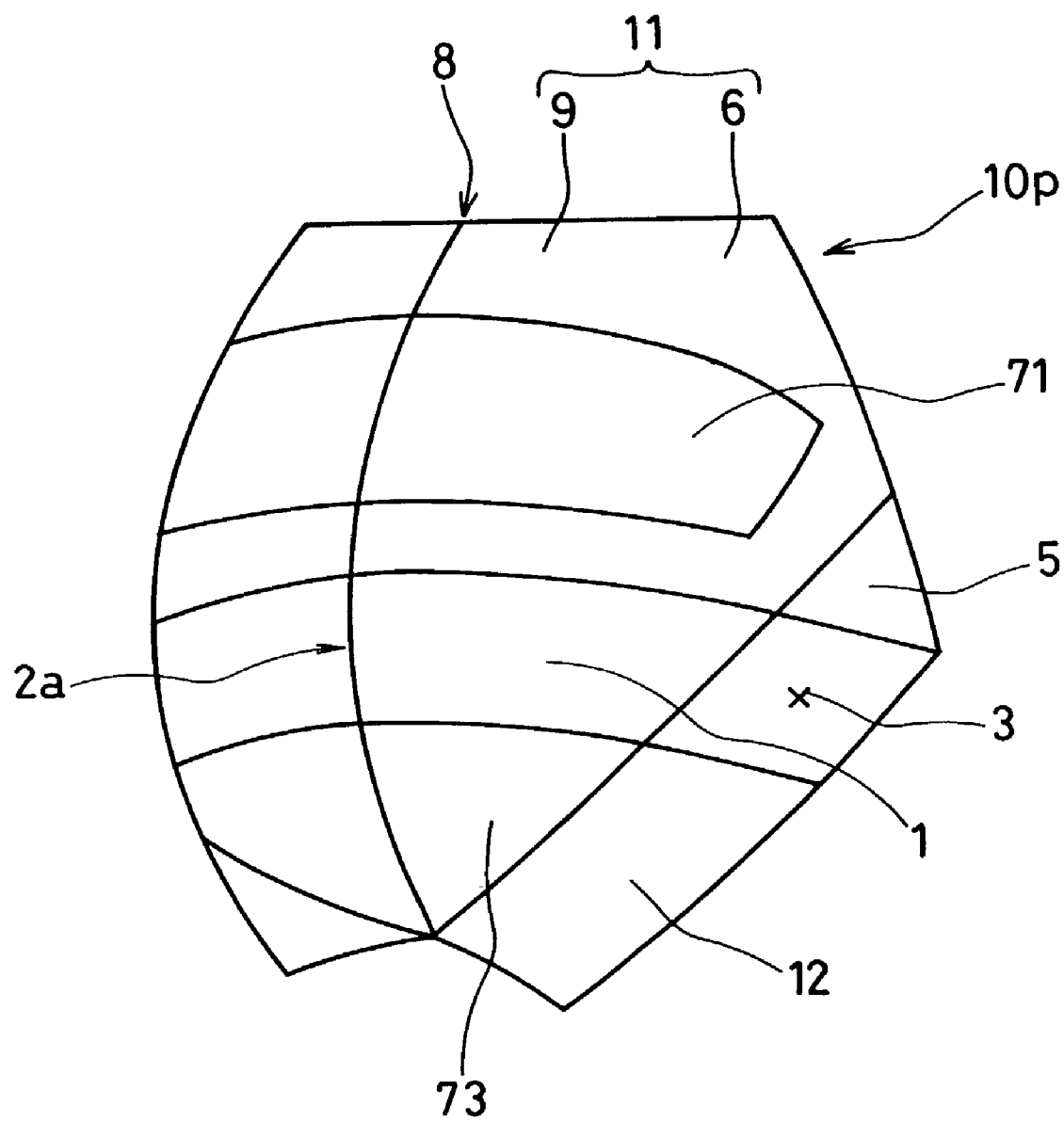
FIG. 56 is a perspective view of the short type girdle of FIG. 55 from the rear side.
Figure 57:
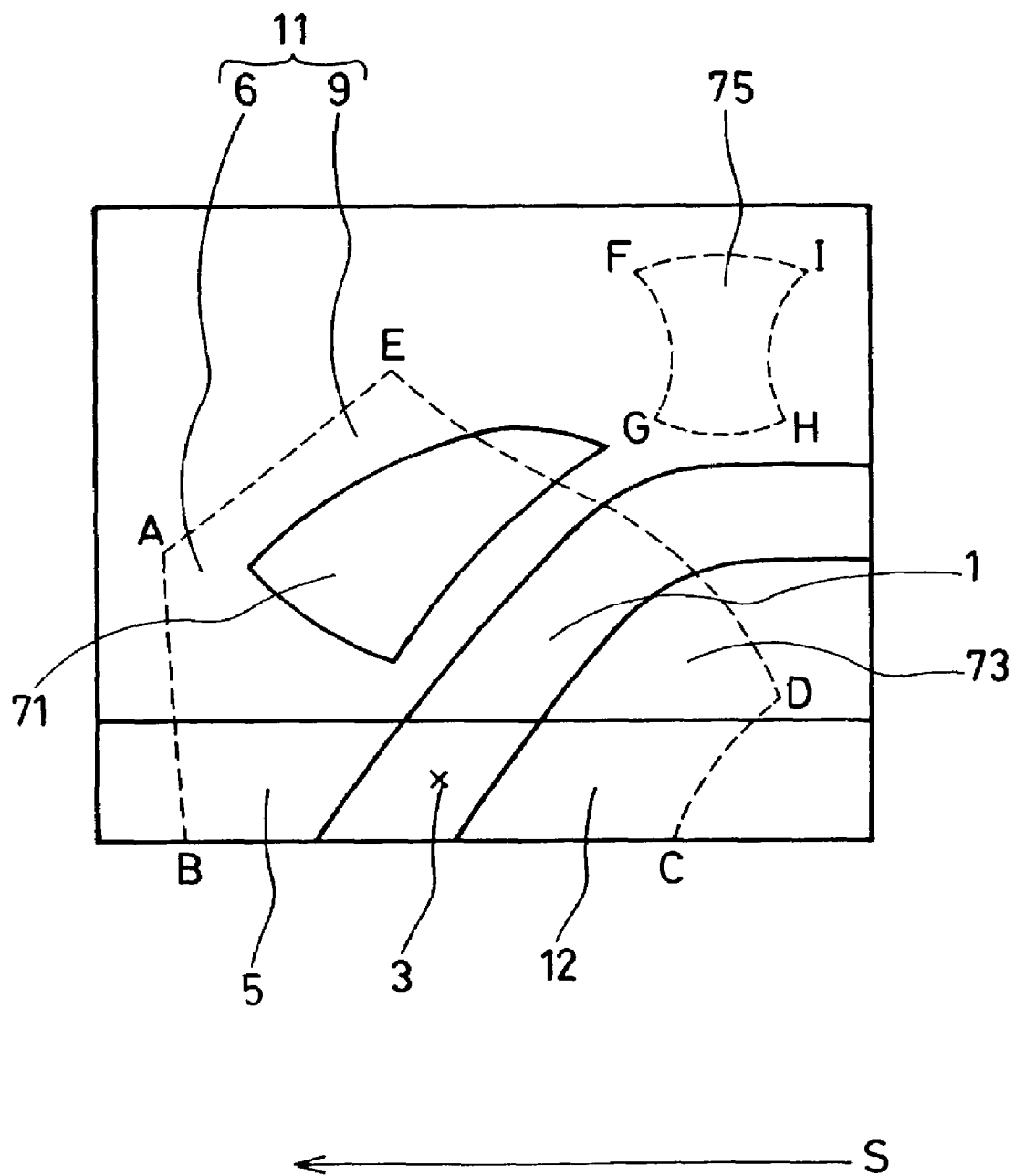
FIG. 57 is a plan view of a fabric used for a part from the back to the side front of the girdle shown in FIGS. 55 and 56 before cutting.

Next, referring to FIGS. 55 to 57, a short type girdle as an embodiment of a garment of the present invention is described.

FIG. 55 is a perspective view of a short type girdle of the present invention from the front side; FIG. 56 is a perspective view thereof from the back side; and FIG. 57 is a plan view of a fabric used for a part from the back to the side front of this girdle before cutting.

The short type girdle 10*p* shown in FIGS. 55 to 57 has relatively similar parts to those in the long type girdle 10*n* shown in FIGS. 52 to 54. Therefore, the same signs are applied to the same parts as in the long type girdle 10*n*, and detailed descriptions are omitted.

In this short type girdle 10*p*, right and left parts of the strong straining portion 1 also are connected at a position 2*a* on the back side of the girdle corresponding to os sacrum of the wearer's body. Furthermore, in the same manner as in the girdle 10*n* shown in FIGS. 52 to 54, a strong straining portion 6 is bent downward at the sides of a strong straining portion (F) for pressing abdomen, and further extends along the upper sides of strong straining portions 5 and 1. Front bottom parts 76 are attached to lower sides of the strong straining portion (F) 20 for pressing abdomen shown in FIG. 55 in seam lines 79 by sewing. (Thus, the front bottom parts 76 are not formed by knitting them differently from the power net part of the strong straining portion (F) 20 in abdominal region. This fabric is a power net fabric formed by a usual warp knitting that does not require change of the stitch. Although the straining force of these parts is not particularly limited, it corresponds to the grade of the third strong straining portion.) Numeral 78 indicates leg holes.

This short type girdle was formed by knitting and differentiating the strong straining portions into four grades of the first strong straining portion, the second strong straining portion, the third strong straining portion, and the weak straining portion as described above. Four grades of the first strong straining portion, the second strong straining portion, the third strong straining portion, and the weak straining portion as described above were differentiated by changing the stitch appearing on the front side of the ground knitted fabric by jacquard warp knitting in the same manner as used in the long type girdle shown in FIGS. 52 to 54.

That is, the ground knitted fabric formed by jacquard knitting comprises a warp knitted fabric knitted with an inelastic yarn and using an elastic yarn as insert yarn. By changing the stitch appearing on the front side of the ground knitted fabric depending on the requirement of the strength of straining force thereby to form predetermined portions with relatively strong straining forces and relatively weak straining forces in patterns in predetermined parts, different portions with desired straining forces are formed at predetermined positions in predetermined patterns depending on the requirement of the strength of straining forces.

In this example, knitting also was carried out by varying power net stitches as described above. The first strong straining portion, the second strong straining portion and the third strong straining portion were knitted with respective satin-like net stitches, and the weak straining portion was knitted with a mesh-like net stitch.

In this embodiment, in the same manner as in the above embodiment, the strong straining portions were differentiated into three grades of the first strong straining portion, the second strong straining portion and the third strong straining portion by having a racking of two needles in a large, medium or small proportion in one repeat knitted unit. Furthermore, in this example, a mesh-like net stitch having a larger space and a lower density of yarn per unit than a satin-like net stitch was used in the weak straining portion.

In this embodiment, as the yarn forming the ground knitted fabric, a nylon yarn of 20 denier was used for both the yarn appearing on the front side and the yarn appearing on the back side. As insert yarn, one polyurethane elastic yarn of 280 denier and one polyurethane elastic yarn of 40 denier were used for each wale. The polyurethane elastic yarn of 40 denier was inserted while winding with respect to the wale direction, in other words, so as to reach a plurality of wales, so that stretchability was expressed in two directions, namely, not only in the wale direction, but also in the course direction in perpendicular to the wale direction. The polyurethane elastic yarn of 280 denier was inserted approximately on the same wale, and contributes mainly to the stretchability in the wale direction. Regardless of the change in the stitch of the ground knitted fabric, these polyurethane elastic yarns were inserted approximately uniformly in the entire ground knitted fabric by the above-described method and proportion. The ratio of the nylon yarn and the polyurethane elastic yarns used in the entire fabric was 80 wt. % of the nylon yarn to 20 wt. % of the polyurethane elastic yarns.

The power net stitch fabric of the front bottom parts 76 comprises 80 wt. % of a nylon yarn of 20 denier and 20 wt. % of a polyurethane elastic yarn. The polyurethane elastic yarn was used as insert yarn, and one polyurethane yarn of 40 denier was inserted for each wale. The polyurethane elastic yarn of 40 denier was inserted on approximately the same wale, and contributes mainly to the stretchability in the wale direction.

The short type girdle shown in FIGS. 55 to 57 has, as a strong straining portion (A), the strong straining portion 1 in which right and left parts are connected at the position 2a on the back side of the girdle corresponding to os sacrum of the wearer's body and which covers a region from the position 2a through the tops of the bulges of the buttocks or vicinities thereof in an approximately middle part of musculus gluteus maximus at right and left approximately in the direction of muscle fibers of musculus gluteus maximus to at least the vicinity of trochanter major 3. In the strong straining portion 1, the section corresponding to the region where trochanter major 3 is present is formed of the first strong straining portion having a racking of two needles in a large proportion, and the strong straining portion 1 other than the section corresponding to the region where trochanter major 3 is present is formed of the second strong straining portion having a racking of two needles in a medium proportion. The strong straining portion (F) for pressing abdomen indicated by numeral 20 at the center of hypogastric region is formed of the second strong straining portion.

The strong straining portion 5 connected to right and left slightly lower sides of the strong straining portion (F) 20 and the strong straining portion 12 connected to the strong straining portion 5 through the section corresponding to the region where trochanter major 3 is present are united to form a strong straining portion (B2). Other than the section corresponding to the region where trochanter major 3 is present, the strong straining portions 5 and 12 are formed of the second strong straining portion.

Furthermore, the strong straining portions 6 as one embodiment of the strong straining portion (C), and the portion indicated by the strong straining portion 9 of the strong straining portion (D) that covers the waist region at the rear of the strong straining portion 6 integrally are formed of the third strong straining portion.

Other portions, namely, an upper part of the buttocks indicated by 71, a part a little higher than gluteal cleft at right and left indicated by 73, and an upper part of the abdomen indicated by 74 are formed of a mesh-like net stitch as the weak straining portion.

This girdle also has, as a strong straining portion (A), the strong straining portion 1 in which right and left parts are connected at the position 2a on the back side of the girdle corresponding to os sacrum of the wearer's body and which covers the region from the position 2a through the tops of the bulges of the buttocks or vicinities thereof in an approximately middle part of musculus gluteus maximus at right and left approximately in the direction of muscle fibers of musculus gluteus maximus to at least the vicinity of trochanter major 3. Therefore, musculus gluteus maximus can be supported firmly in the direction of its muscle fibers. Thus, it can play a large role in supporting the rotating motion of the hips, preventing a decrease in the rotating angle of the hips, and stabilizing the pelvis in anterior-posterior direction. For an elderly person, it is effective in preventing falling down. Furthermore, it can play a large role in extending the hip joint in anterior-posterior direction when running, jumping, and climbing up a slope.

Furthermore, the portion indicated by the strong straining portion 5 is united with the strong straining portion 12 extending further from the vicinity of trochanter major 3 to a lower part of the bulges of the buttocks to form a strong straining portion (B2). Thus, in this girdle, because of the presence of the strong straining portion (B2), the function of pressing trochanter major 3 is enhanced further, and the functions of improving the joint between caput ossis femoris 204 and acetabulum and increasing the stability of the hip joint are enhanced further. Furthermore, with the strong straining portion 12, the function of keeping the bulges of the hips in a high position can be provided.

Furthermore, because right and left parts of the strong straining portion 5 and right and left parts of the strong straining portion 6 are connected to each other through the strong straining portion (F) 20, the functions of supporting abdominal muscles more strongly, reducing lumbar lordosis, maintaining good posture, making youthful figure, and preventing generation of pains such as lumbar pains can be displayed more easily. Furthermore, because the strong straining portions 6 and 9 are united to form the strong straining portion 11, the functions of supporting the region from the vicinity of the position 8 at the back center of the waist through musculus latissimus dorsi 308 and musculus gluteus medius 309 at right and left and musculus obliquus externus abdominis 302 more strongly, preventing backward inclination of the pelvis, and keeping a stable position of the pelvis are displayed more easily.

Moreover, in this girdle, because the strong straining portions are not formed by lining with a cloth or the like but are formed by changing stitches, there is substantially no difference in level at a boundary between strong straining portions and weak straining portions. Therefore, there is no possibility that such a difference in level at the boundary is reflected into an outer wear and appears on the outer wear, deteriorating the appearance of the wearer.

FIG. 57 is a plan view of a fabric used for a part from the back to the side front of this girdle before cutting. The section enclosed by a broken line A-B-C-D-E-A indicates a cutting line of a body fabric (fabric for covering) for the region from the front to the back on the right side other than the strong straining portion 20 for pressing abdomen and the upper abdomen part 74 in FIG. 55. The section 75 enclosed by a broken line F-G-H-I is a cutting line of a piece corresponding to the crotch 75. The E-D line is the center line at the back of the girdle. Because the same signs are applied to the same parts in FIG. 57 as those in FIGS. 55 and 56, it is easy to understand that which of the respective parts shown in FIG. 57 constitutes any part in FIGS. 55 and 56. In FIG. 57, the direction in which the yarn forming this jacquard raschel warp knitted fabric is supplied, namely, the wale direction, is indicated by an arrow S.

The girdle shown in this embodiment is comprised of a total of six fabrics, namely, two for right and left body sides of the fabric shown in FIG. 57, which is used for a part from the back to the side front; the crotch cloth piece indicated by 75; an abdomen cloth in which the upper abdomen part 74 and the strong straining portion (F) 20 in FIG. 55 are knitted differently and united; and lower front end parts 76 for right and left.

Figure 58:
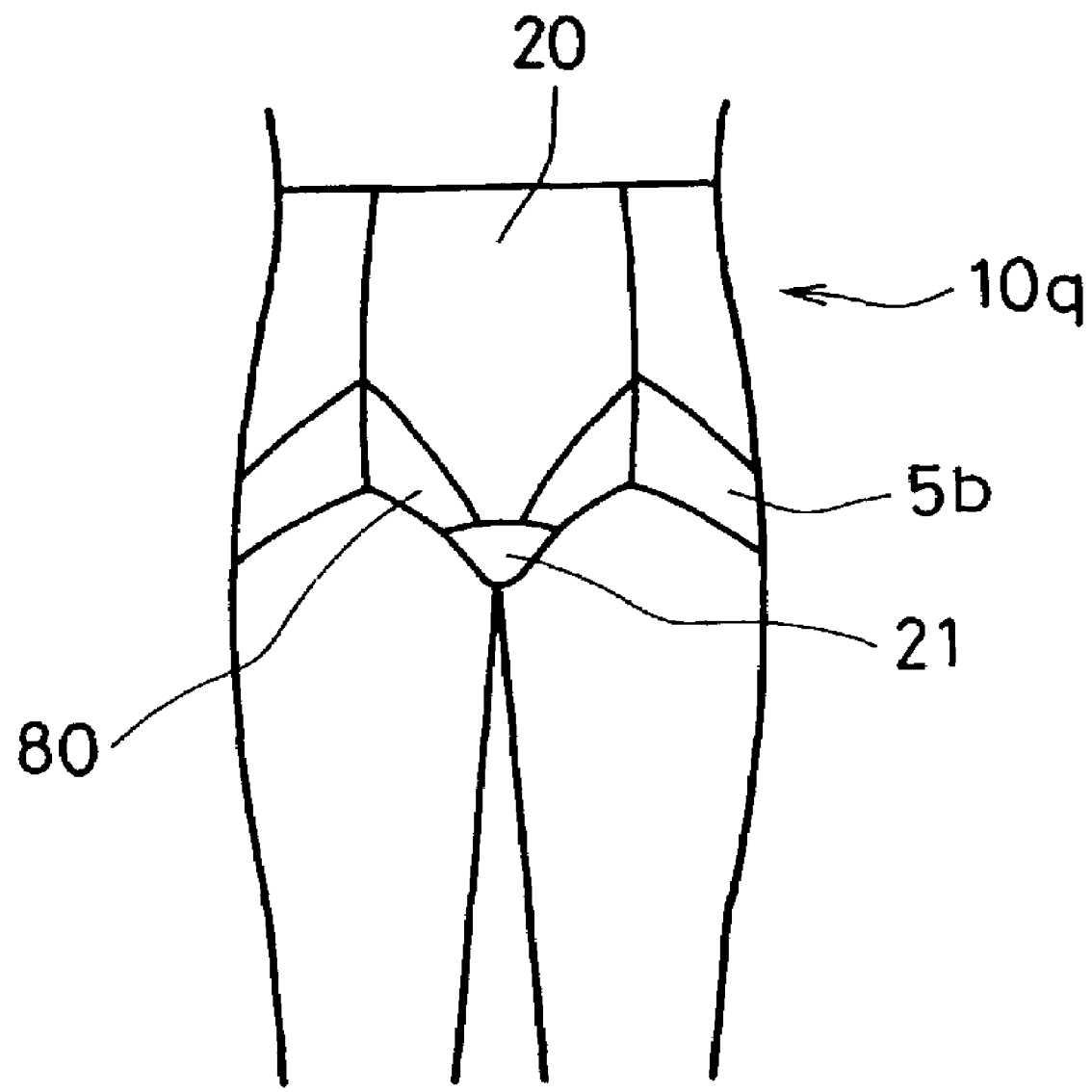
FIG. 58 is a front view of still another embodiment of a short type girdle as a garment of the present invention in wearing condition.
Figure 59:
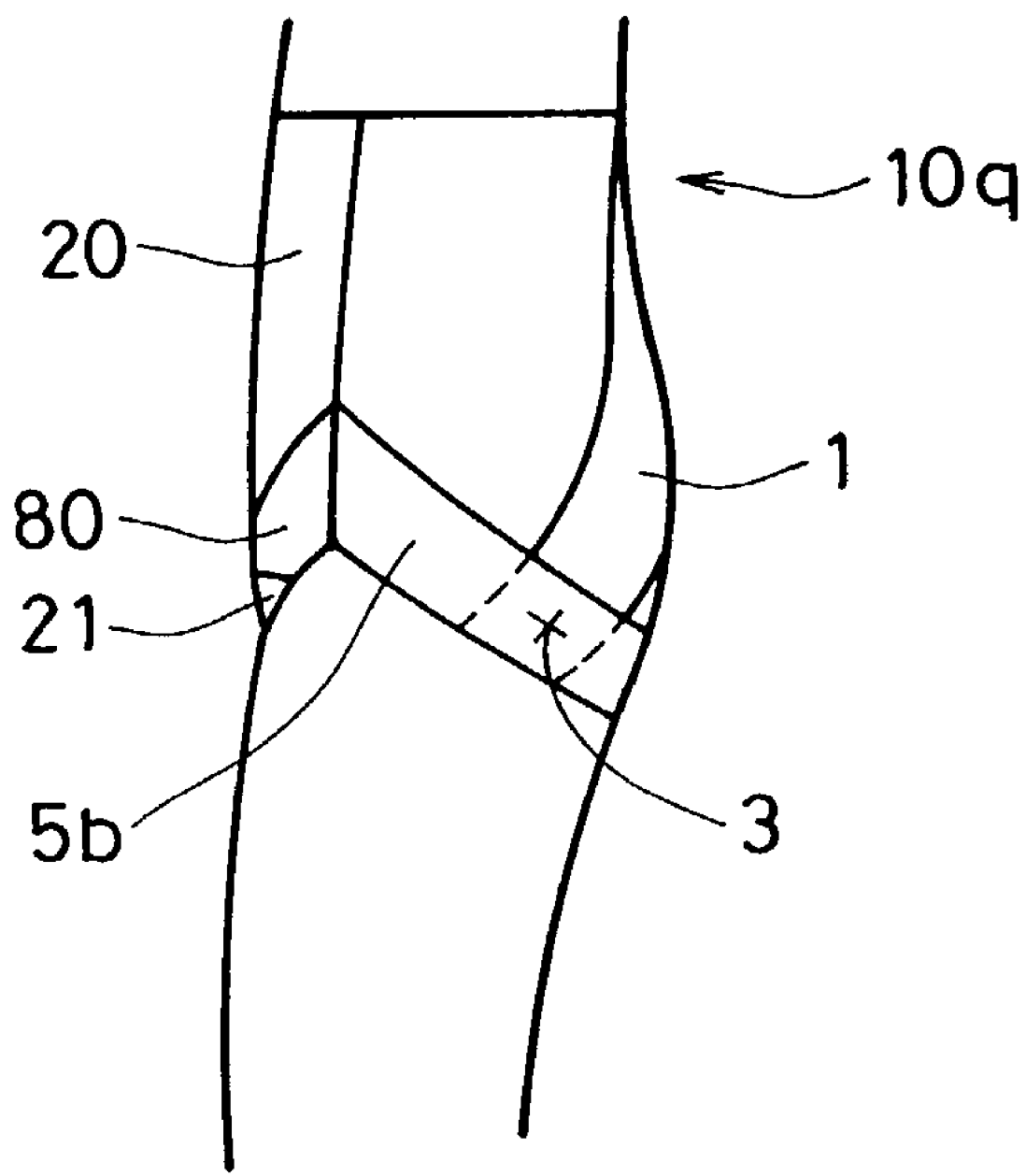
FIG. 59 is a left side view of the short type girdle of FIG. 58 in wearing condition.
Figure 60:
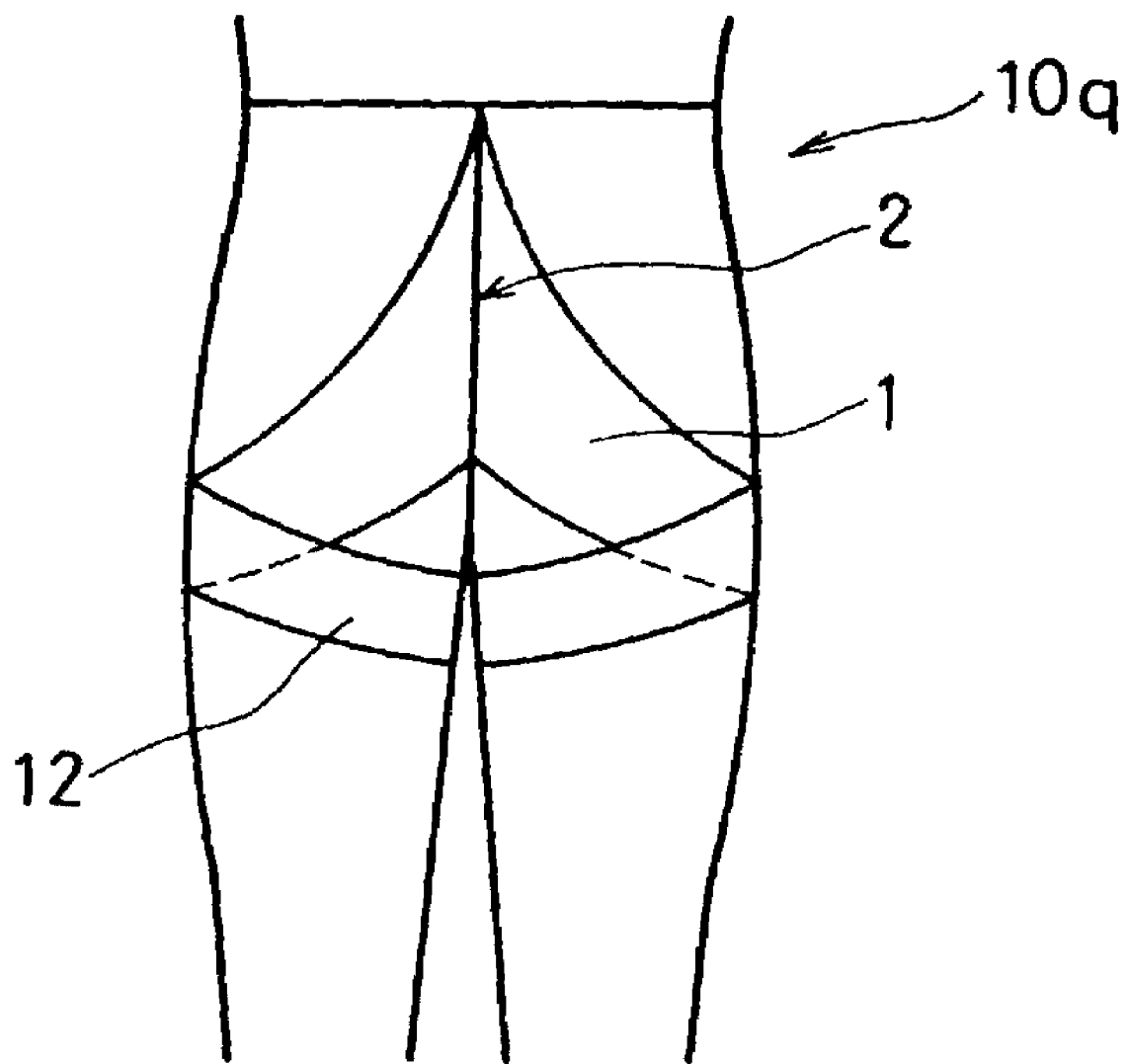
FIG. 60 is a rear view of the short type girdle of FIG. 58 in wearing condition.

Next, FIGS. 58 to 60 show a front view, a left side view and a rear view of still another embodiment of a short type girdle as a garment of the present invention in wearing condition, respectively. The short type girdle 10q shown in FIGS. 58 to 60 has, as a strong straining portion (A), a strong straining portion 1 in which right and left parts are connected at a position 2 on the back side of the girdle corresponding to from fourth vertebra lumbalis to os sacrum of the wearer's body and which covers the region from the position 2 through the tops of the bulges of the buttocks or vicinities thereof in an approximately middle part of musculus gluteus maximus at right and left approximately in the direction of muscle fibers of musculus gluteus maximus to the vicinity of trochanter major 3. Furthermore, in the same way as in FIG. 19, the girdle 10q has a strong straining portion (F) 20 for pressing abdomen at the center of hypogastric region, which has a main stretch direction in the longitudinal direction of the garment. At the periphery of the lower end of the girdle 10q, there are front bottom clothes indicated by 80. In this embodiment, for these front bottom clothes, a power net knitted fabric that is a stretch fabric having its edge processed for fraying prevention and does not need, what is called, a hem finish (thus, a fabric having a flat edge that is not subjected to a hem finish in which an edge is folded back and sewn), which has a strong straining force so that it is fitted to the body of the wearer, is used. This girdle also has strong straining portions 5b connected to the strong straining portions of these front bottom clothes 80 and extending from the sides of the front bottom clothes along the lower end at the sides of the girdle to the vicinity of trochanter major 3, and a strong straining portion 12 extending from the strong straining portions 5b along the lower end at the back of the girdle through a lower part of the bulges of the buttocks. Because the front bottom clothes 80 as strong straining portions are connected to the strong straining portion (F) 20, when considering the front bottom clothes 80 as extensions of the strong straining portion for pressing abdomen, it is possible to consider that the front bottom clothes 80 and the strong straining portions 5b are approximately equivalent to a strong straining portion 5 that covers a region extending obliquely downward from a position on musculus rectus abdominis in hypogastric region approximately in the direction of the muscle fibers of musculus obliquus internus abdominis at right and left to the vicinity of trochanter major 3, which has approximately the same effect as that of the combination of the strong straining portion (F) 20 and the strong straining portions 5 of the girdle shown in FIGS. 16 to 18.

Thus, in the short type girdle 10q of this embodiment, the strong straining portion 1 passes through the tops of the bulges of the buttocks or vicinities thereof in the direction of muscle fibers of musculus gluteus maximus, and moreover, right and left parts of the strong staining portion 1 are connected at the position 2 on the back side of the girdle corresponding to the region from the fourth vertebra lumbalis to os sacrum of the wearer's body. Therefore, musculus gluteus maximus can be supported firmly in the direction of its muscle fibers. Thus, it can play a large role in supporting the rotating motion of the hips, preventing a decrease in the rotating angle of the hips, and stabilizing the pelvis in anterior-posterior direction. For an elderly person, it is effective in preventing falling down. Furthermore, it can play a large role in extending the hip joint in anterior-posterior direction when running, jumping, and climbing up a slope. Furthermore, because the strong straining portions 1, 5b and 12 cover the vicinity of trochanter major 3, the functions of improving the joint between caput ossis femoris 204 and acetabulum and increasing the stability of the hip joint are displayed. Furthermore, considering the front bottom clothes 80 as extensions of the strong straining portion (F) 20 for pressing abdomen as described above, with these parts and the strong straining portions 5b, the functions of supporting musculus rectus abdominis 301 in part and musculus obliquus internus abdominis, reducing lumbar lordosis, maintaining good posture, making youthful figure, and preventing generation of pains such as lumbar pains can be displayed. Furthermore, with the strong straining portion 12, the function of keeping the bulges of the hips in a high position can be provided.

Figure 61:
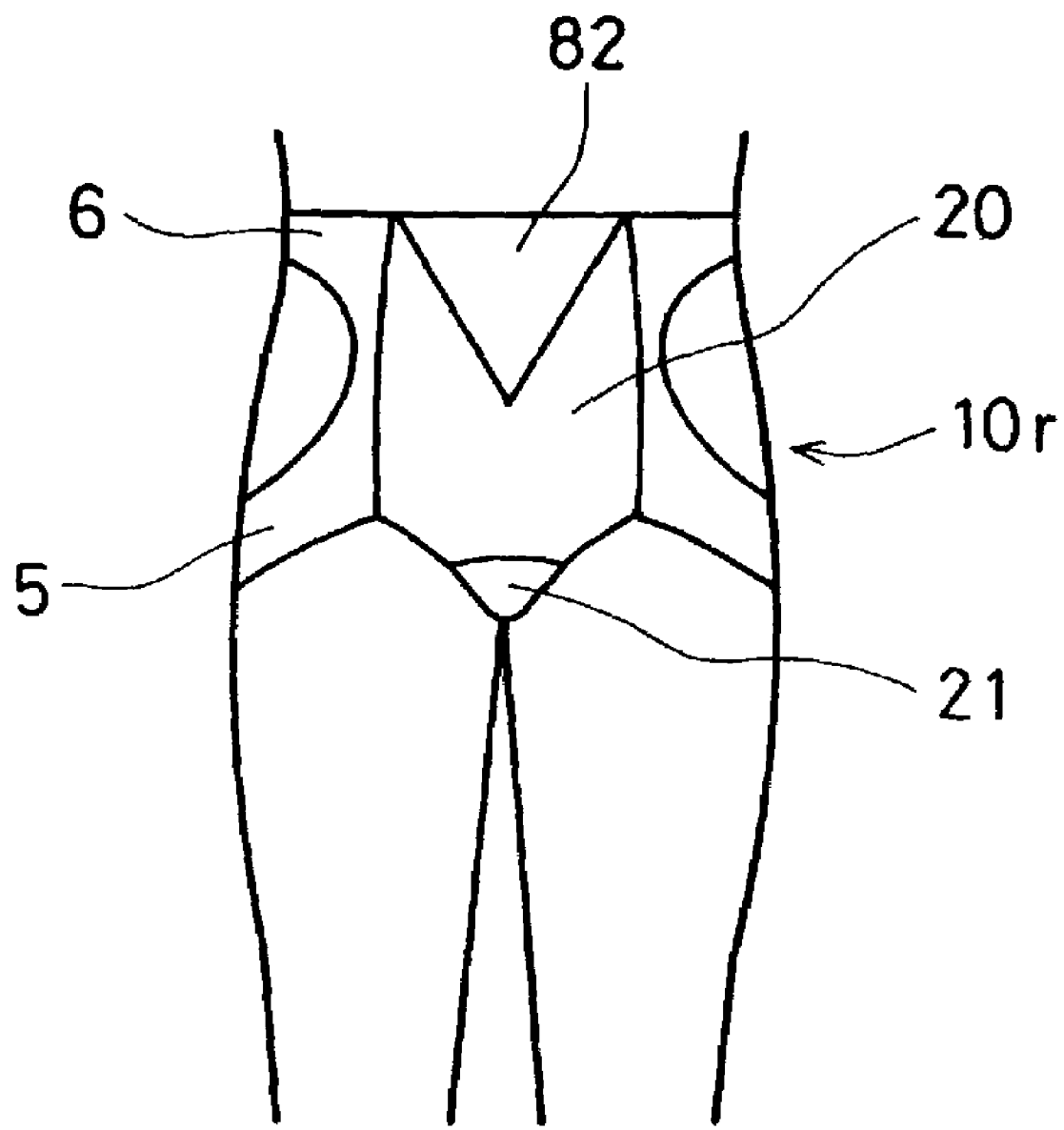
FIG. 61 is a front view of still another embodiment of a short type girdle as a garment of the present invention in wearing condition.
Figure 62:
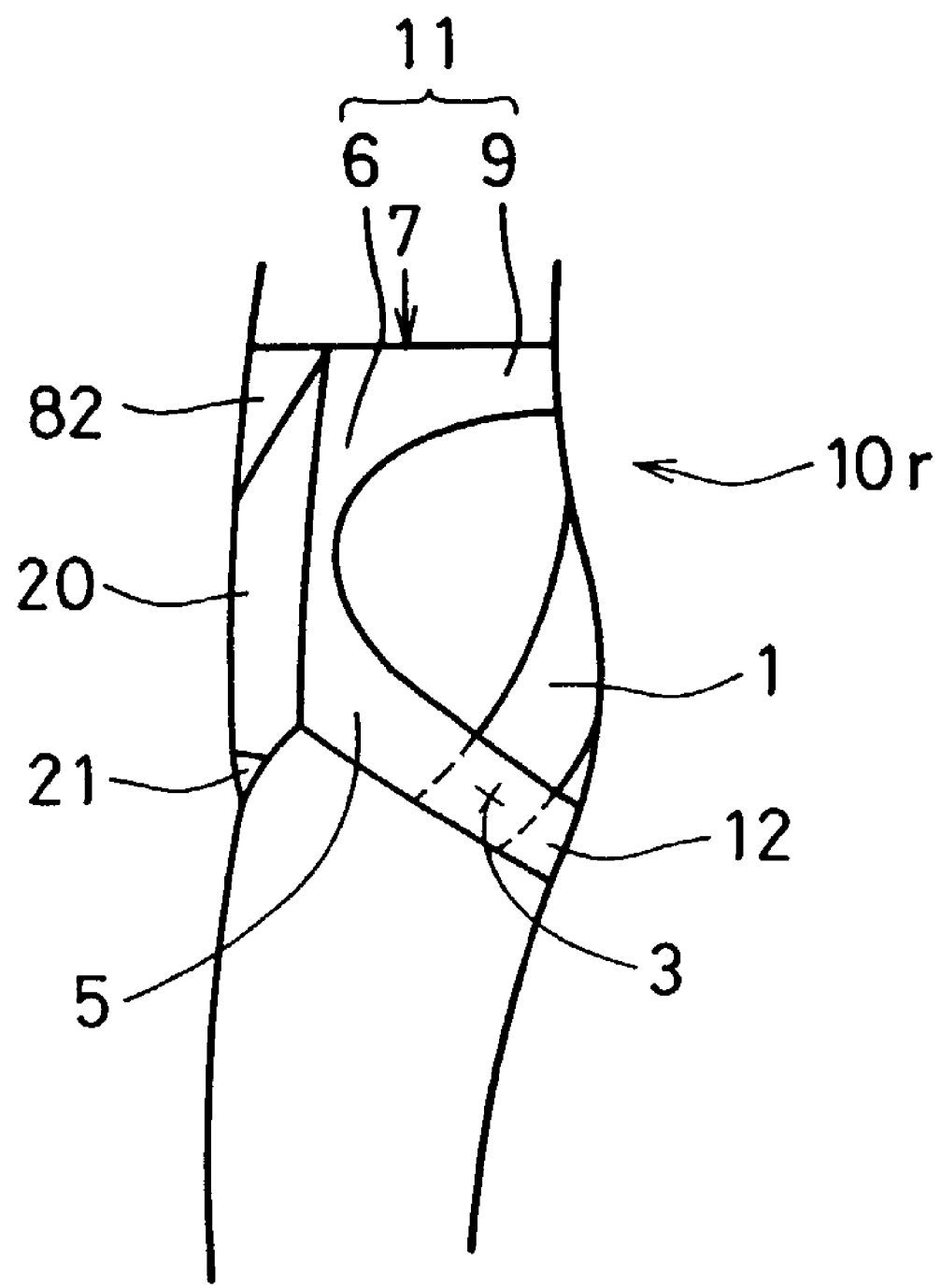
FIG. 62 is a left side view of the short type girdle of FIG. 61 in wearing condition.
Figure 63:
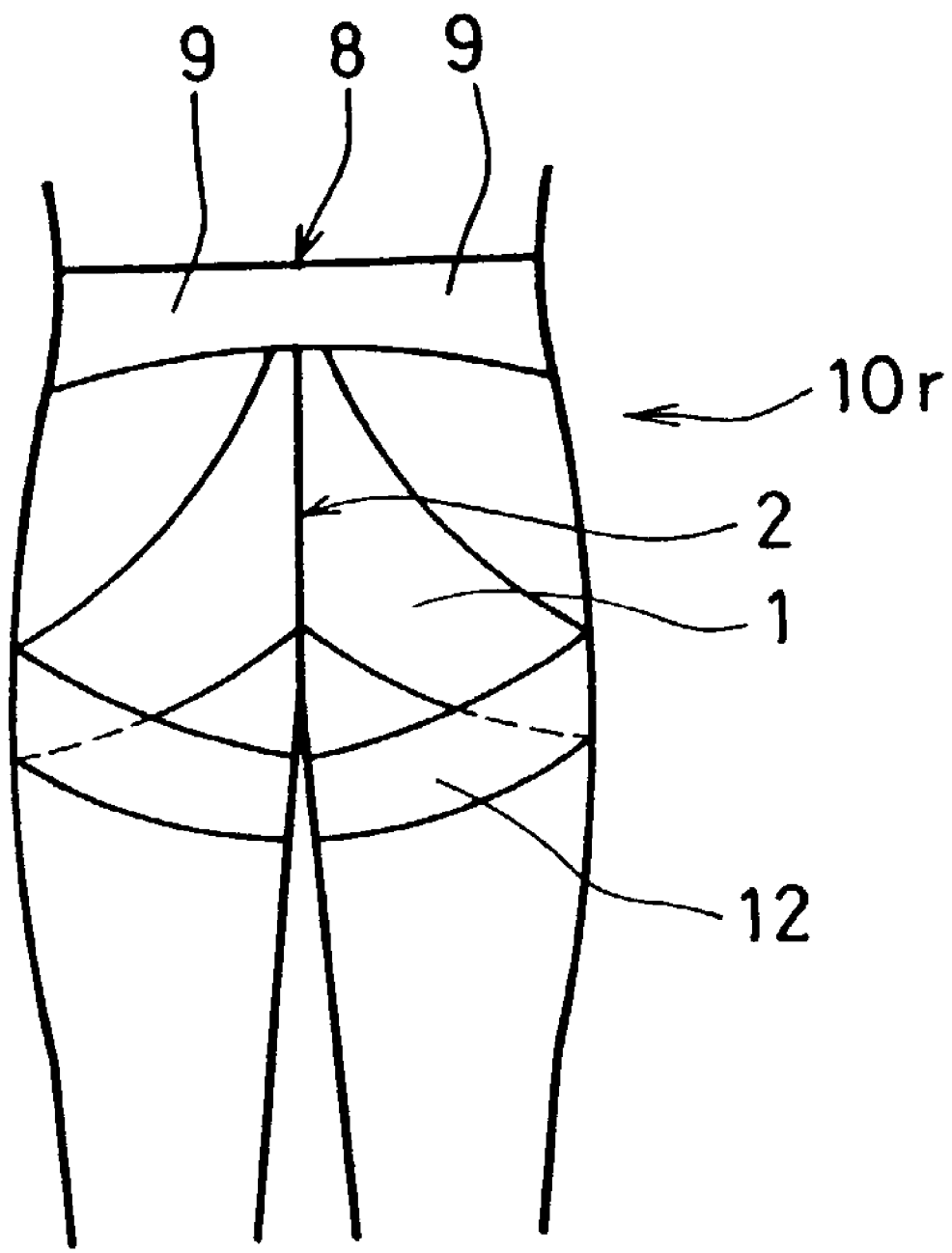
FIG. 63 is a rear view of the short type girdle of FIG. 61 in wearing condition.

Next, FIGS. 61 to 63 show a front view, a left side view and a rear view of still another embodiment of a short type girdle as a garment of the present invention in wearing condition, respectively. The short type girdle 10r shown in FIGS. 61 to 63 has, as a strong straining portion (A), a strong straining portion 1 in which right and left parts are connected at the position 2 on the back side of the girdle corresponding to the region from the fourth vertebra lumbalis to os sacrum of the wearer's body and which covers a region from the position 2 through the tops of the bulges of the buttocks or vicinities thereof in an approximately middle part of musculus gluteus maximus at right and left approximately in the direction of muscle fibers of musculus gluteus maximus to the vicinity of trochanter major 3. This girdle further has a strong straining portion (F) 20 for pressing abdomen at the center of hypogastric region, which has a main stretch direction in the longitudinal direction of the garment. One end of each of right and left parts of a straining portion 5 is connected to each of right and left slightly lower sides of the strong straining portion (F) 20. One end of each of right and left parts of a strong straining portion 6 is connected to each of right and left upper sides of the strong straining portion (F) 20. A slight difference from FIG. 19 is that the strong straining portions 5 and 6 are connected on the sides of the garment. The portion indicated by the strong straining portion 5 further extends from the vicinity of trochanter major 3 through a lower part of the bulges of the buttocks along the lower end at the back as indicated by the strong straining portion 12. The strong straining portions 5 and 12 are united to form a strong straining portion (B2). Furthermore, this girdle has, as a strong staining portion (D), a strong straining portion 9 in which right and left parts are connected approximately in the vicinity of a position 8 at the back center of the waist and which covers a region extending from the vicinity of the position 8 at the back center of the waist through musculus latissimus dorsi 308 and musculus gluteus medius 309 at right and left and a part of musculus obliquus externus abdominis 302 to at least a position exceeding the sides 7 of the wearer to the front side. This girdle also has the strong straining portion 6 in which right and left parts are connected at a position 4 on musculus rectus abdominis in hypogastric region and which covers a region extending obliquely upward from the position 4 (the strong straining portion (F) 20 for pressing abdomen) on musculus rectus abdominis in hypogastric region approximately in the direction of muscle fibers of musculus obliquus externus abdominis at right and left to at least a position exceeding the sides 7 of the wearer to the back side. The strong straining portions 6 and 9 are united to form a strong straining portion 11. Thus, in this short type girdle 10*r*, the strong straining portions 5, 6, 9 (11) and 12 are connected in series. Although not particularly limited, the method in which the stitch appearing on the front side of the ground knitted fabric by jacquard raschel knitting is changed to form predetermined portions with relatively strong straining forces and relatively weak straining forces in patterns in predetermined parts as shown in the previous embodiment of FIGS. 52 to 57 can be applied easily to the garment of this embodiment.

In this short type girdle 10*r* described above, the strong straining portion 1 passes through the tops of the bulges of the buttocks or vicinities thereof in the direction of muscle fibers of musculus gluteus maximus, and moreover, right and left parts of the strong straining portion 1 are connected at the position 2 on the back side of the girdle corresponding to from the fourth vertebra lumbalis to os sacrum of the wearer's body. Therefore, musculus gluteus maximus can be supported firmly in the direction of its muscle fibers. Thus, it can play a large role in supporting the rotating motion of the hips, preventing a decrease in the rotating angle of the hips, and stabilizing the pelvis in anterior-posterior direction. For an elderly person, it is effective in preventing falling down. Furthermore, it can play a large role in extending the hip joint in anterior-posterior direction when running, jumping, and climbing up a slope. Furthermore, because the strong straining portions 1, 5 and 12 cover the vicinity of trochanter major 3, the functions of improving the joint between caput ossis femoris 204 and acetabulum and increasing the stability of the hip joint can be displayed.

Furthermore, with the strong straining portion (F) 20 for pressing abdomen and the strong straining portion 5, the functions of supporting musculus rectus abdominis 301 in part and musculus obliquus internus abdominis, reducing lumbar lordosis, maintaining good posture, making youthful figure, and preventing generation of pains such as lumbar pains can be displayed. Furthermore, with the strong straining portion 12, the function of keeping the bulges of the hips in a high position can be provided.

Furthermore, with the strong straining portion (F) 20 for pressing abdomen and the strong straining portion 6, the functions of supporting musculus rectus abdominis 301 in part and musculus obliquus externus abdominis 302, reducing lumbar lordosis, maintaining good posture, making youthful figure, and preventing generation of pains such as lumbar pains are displayed. Also, because the strong straining portions 6 and 9 are united to form the strong straining portion 11, the functions of supporting the region from the vicinity of the position 8 at the back center of the waist through musculus latissimus dorsi 308 and musculus gluteus medius 309 at right and left and musculus obliquus externus abdominis 302 more strongly, preventing backward inclination of the pelvis, and maintaining a stable position of the pelvis are displayed more easily.

Moreover, in the short type girdle 10*r*, as a front waist cloth 82, a stretch soft fabric having a small straining force, such as a tricot, is folded double and is arranged so that the folded curved edge (the folded-back portion) is on the side of the upper end of the waist. The strong straining portion 11 in which the strong straining portions 6 and 9 are united applies a strong force to the waist. If the strong straining portion (F) 20 reaches the upper end of the waist, the strong straining portion 11 and the strong straining portion (F) 20 together may have too strong straining force, and wearing comfort may decrease. By the front waist cloth 82, such a decrease in wearing comfort is alleviated by softening the force applied to the front side of the waist corresponding to the upper part of stomach, while applying a strong force to the waist from the sides to the back by the strong straining portion 11. Thus, a garment having a balance between wearing comfort and performances of functions can be provided.

Figure 64:
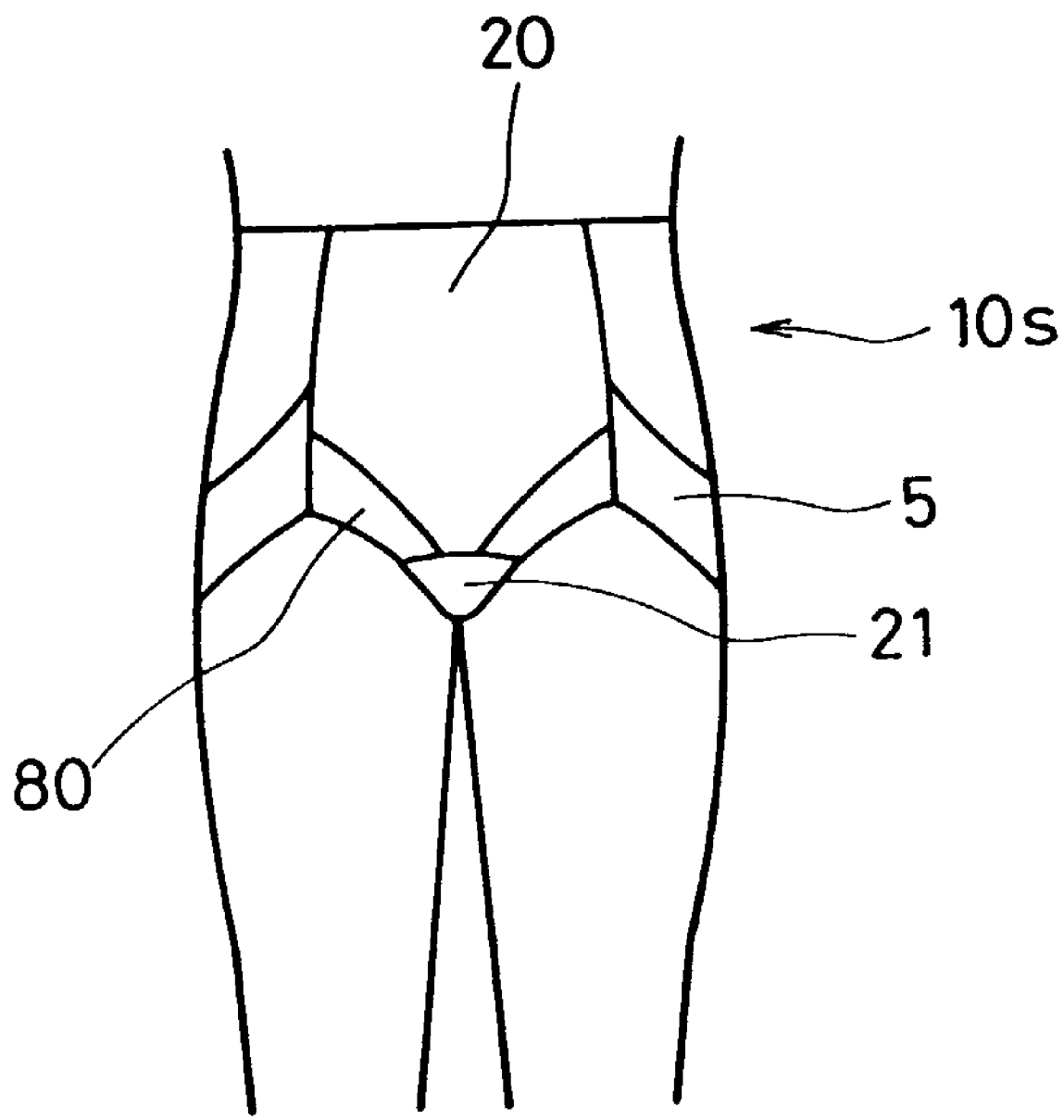
FIG. 64 is a front view of still another embodiment of a short type girdle as a garment of the present invention in wearing condition.
Figure 65:
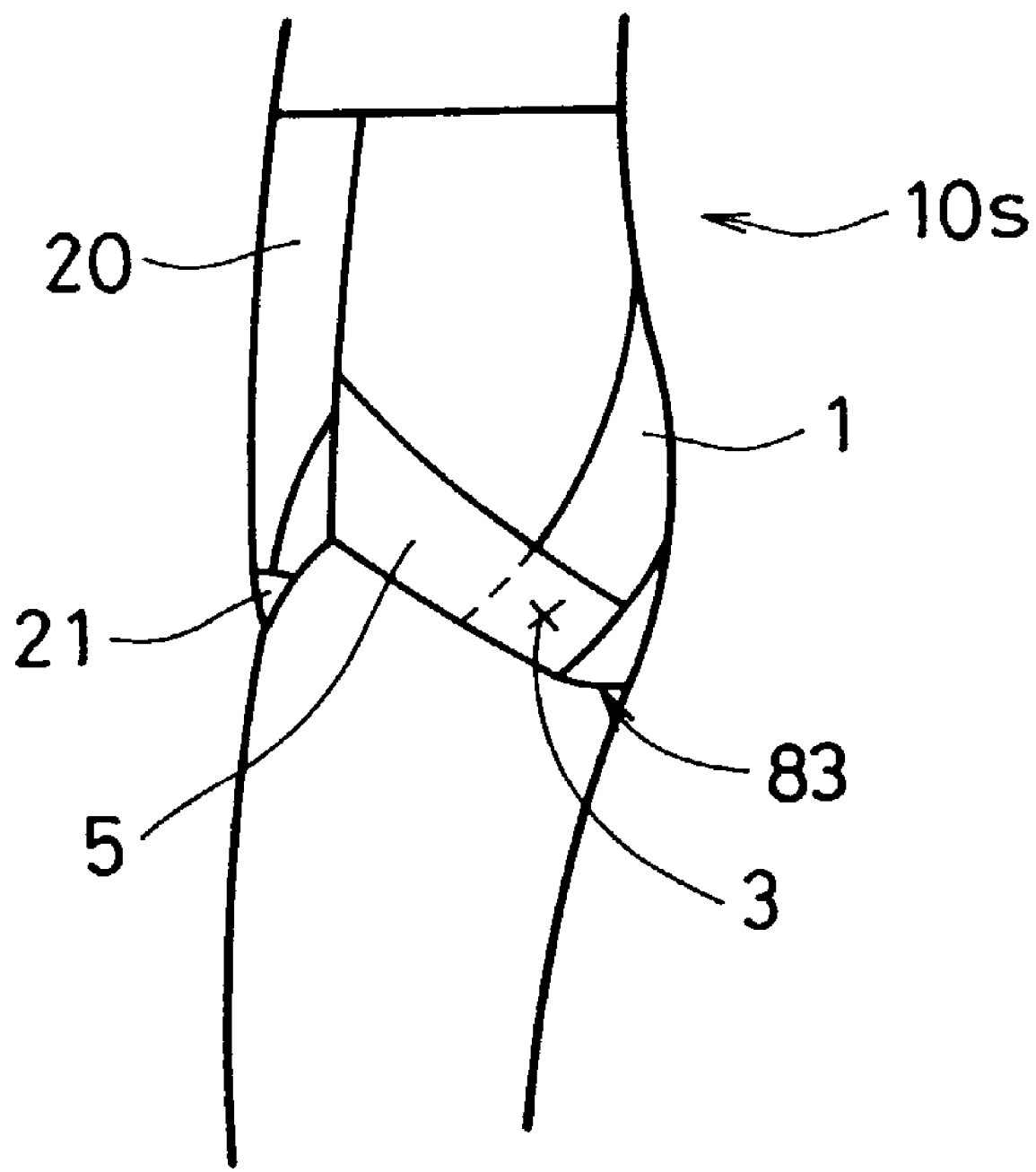
FIG. 65 is a left side view of the short type girdle of FIG. 64 in wearing condition.
Figure 66:
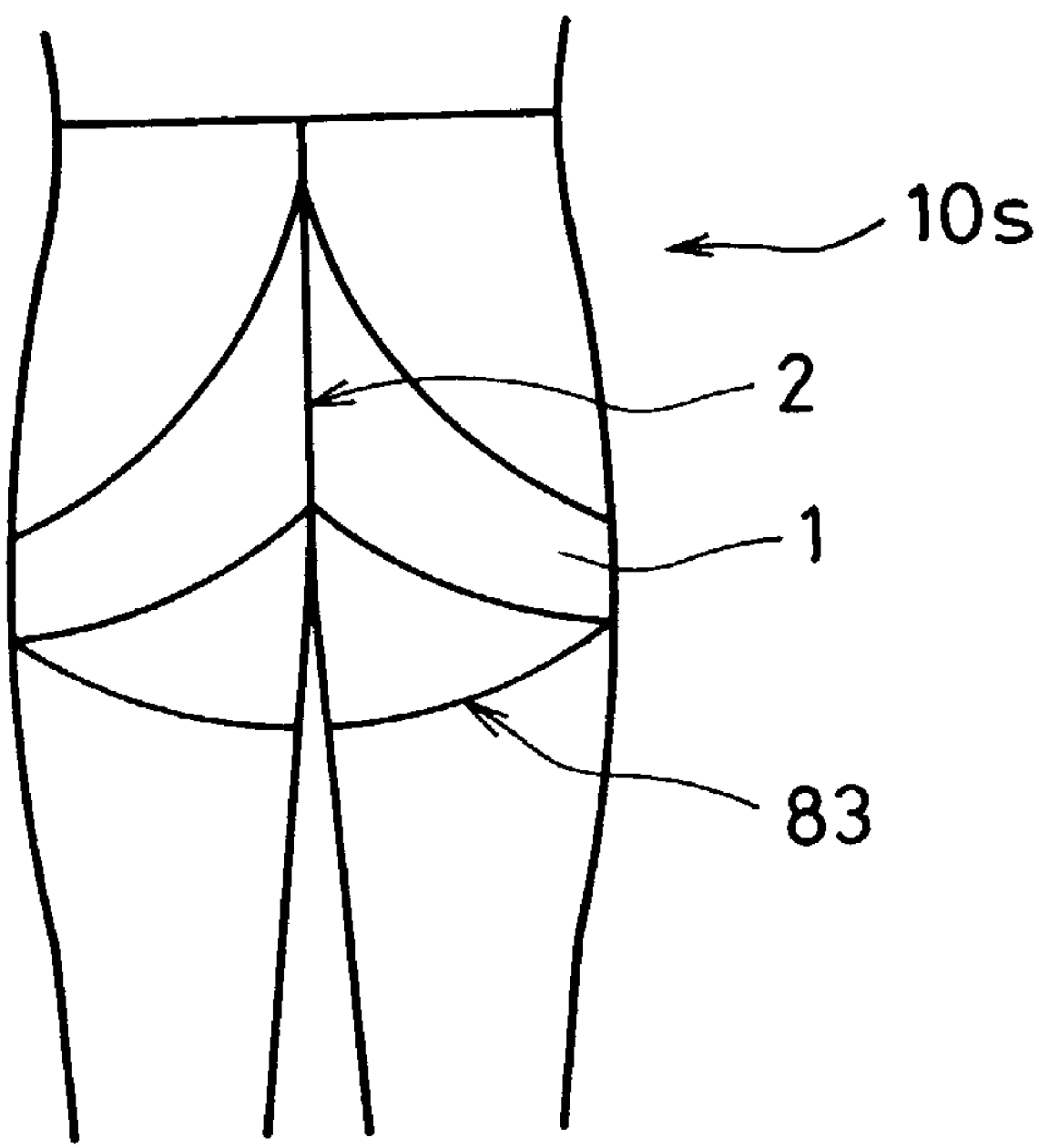
FIG. 66 is a rear view of the short type girdle of FIG. 64 in wearing condition.

Next, FIGS. 64 to 66 show a front view, a left side view and a rear view of still another embodiment of a short type girdle as a garment of the present invention in wearing condition, respectively. The short type girdle 10*s* shown in FIGS. 64 to 66 has, as a strong straining portion (A), a strong straining portion 1 in which right and left parts are connected at a position 2 on the back side of the girdle corresponding to from the fourth vertebra lumbalis to os sacrum of the wearer's body and which covers a region from the position 2 through the tops of the bulges of the buttocks or vicinities thereof in an approximately middle part of musculus gluteus maximus at right and left approximately in the direction of muscle fibers of musculus gluteus maximus to the vicinity of trochanter major 3. Furthermore, in the same way as in FIG. 58, there is a strong straining portion (F) 20 for pressing abdomen at the center of hypogastric region, which has a main stretch direction in the longitudinal direction of the garment. At the periphery of the lower end of the girdle 10*s*, there are front bottom clothes as indicated by numeral 80. In this embodiment, for the front bottom clothes, a power net knitted fabric that is a stretch fabric having its edge processed for fraying prevention and does not need, what is called, a hem finish (thus, a fabric having a flat edge that is not subjected to a hem finish in which an edge is folded back and sewn), which has a strong straining force so that it is fitted to the body of the wearer, is used. This girdle also has a strong straining portion 5 that is connected to the strong straining portion (F) 20 and the strong straining portions as the front bottom clothes 80 and extends from the sides of these portions along the lower end at the sides to the vicinity of trochanter major 3. Because the strong straining portion 5 is connected to the strong straining portion (F) 20, the strong straining portion 5 and the strong straining portion (F) 20 are considered as equivalent to a strong straining portion 5 that covers a region extending obliquely downward from a position on musculus rectus abdominis in hypogastric region approximately in the direction of muscle fibers of musculus obliquus internus abdominis at right and left to the vicinity of trochanter major 3, which has approximately the same functions as those of the strong straining portion (F) 20 for pressing abdomen and the strong straining portion 5 of the girdle shown in FIG. 19.

Thus, in the short type girdle 10s of this embodiment, the strong straining portion 1 passes through the tops of the bulges of the buttocks or vicinities thereof in the direction of muscle fibers of musculus gluteus maximus, and moreover, right and left parts of the strong straining portion 1 are connected at the position 2 on the back side of the girdle corresponding to from the fourth vertebra lumbalis to os sacrum of the wearer's body. Therefore, musculus gluteus maximus can be supported firmly in the direction of its muscle fibers. Thus, it can play a large role in supporting the rotating motion of the hips, preventing a decrease in the rotating angle of the hips, and stabilizing the pelvis in anterior-posterior direction. For an elderly person, it is effective in preventing falling down. Furthermore, it can play a large role in extending the hip joint in anterior-posterior direction when running, jumping, and climbing up a slope. Furthermore, because the strong straining portions 1 and 5 cover the vicinity of trochanter major 3, the functions of improving the joint between caput ossis femoris 204 and acetabulum and increasing the stability of the hip joint are displayed. Furthermore, with the strong straining portion (F) 20 and the strong straining portion 5, the functions of supporting musculus rectus abdominis 301 in part and musculus obliquus internus abdominis, reducing lumbar lordosis, maintaining good posture, making youthful figure, and preventing generation of pains such as lumbar pains can be displayed. Numeral 83 indicates the lower end line on the back side of the main body of the short type girdle.

Figure 67:
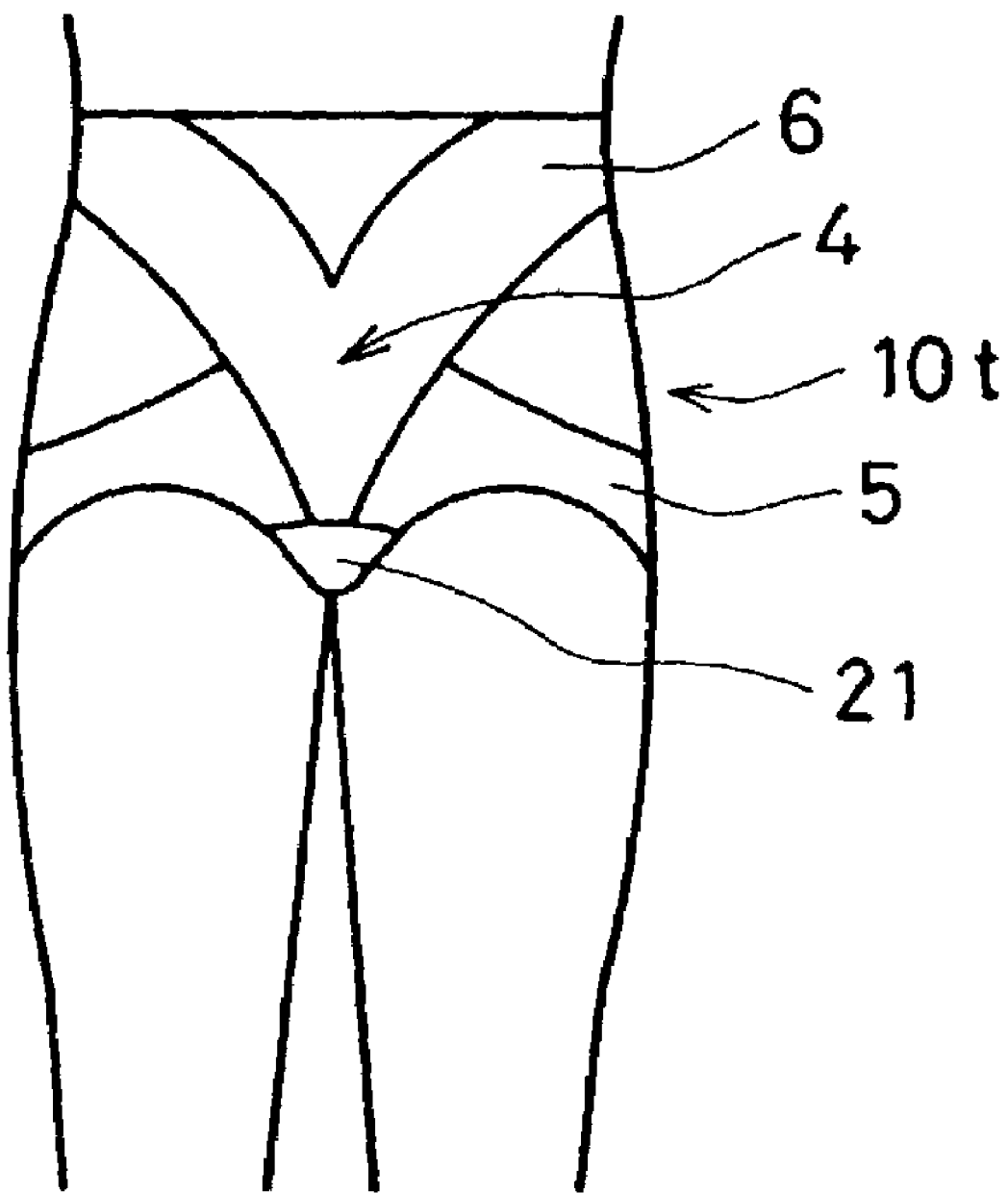
FIG. 67 is a front view of still another embodiment of a short type girdle as a garment of the present invention in wearing condition.
Figure 68:
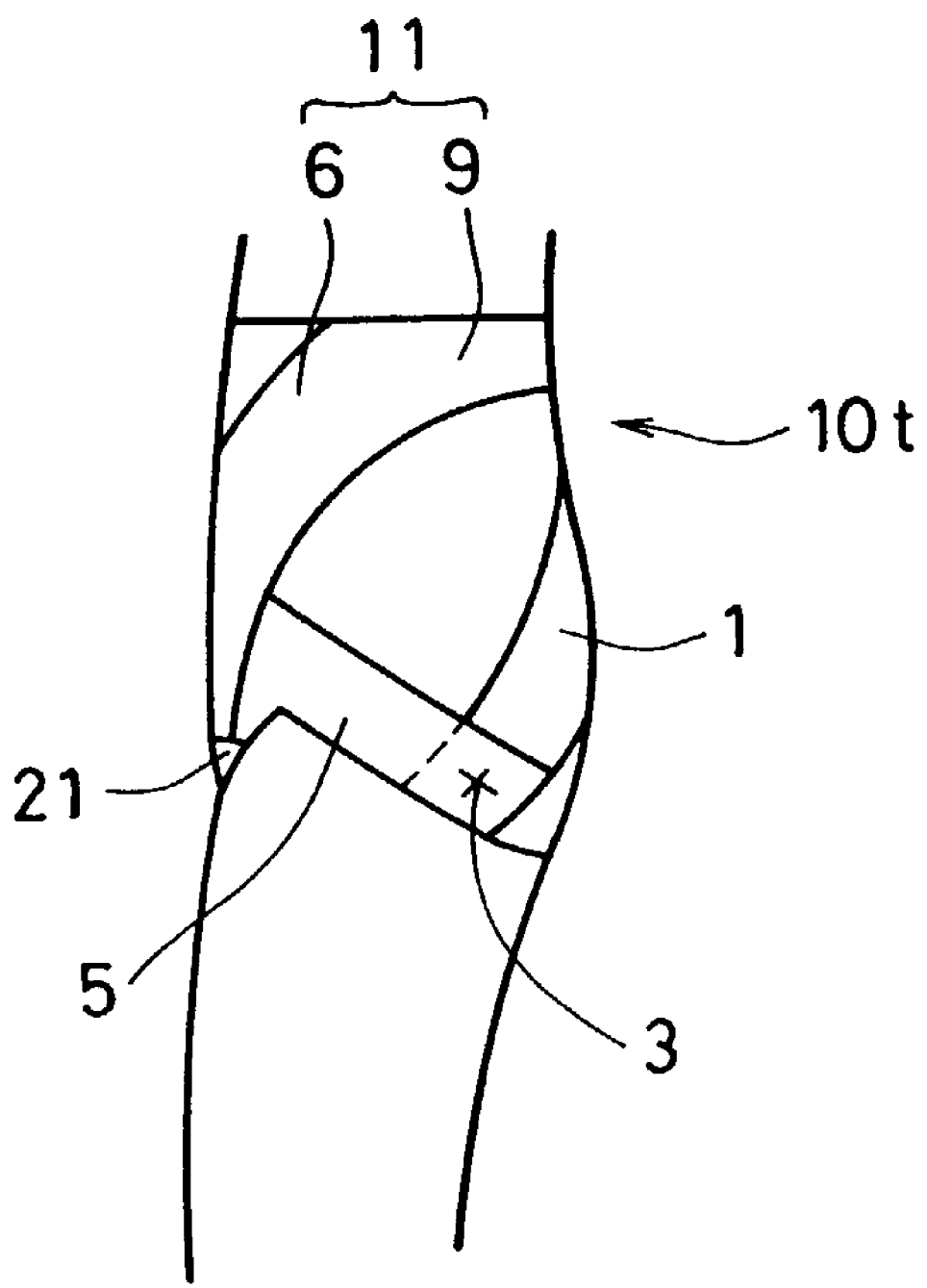
FIG. 68 is a left side view of the short type girdle of FIG. 67 in wearing condition.
Figure 69:
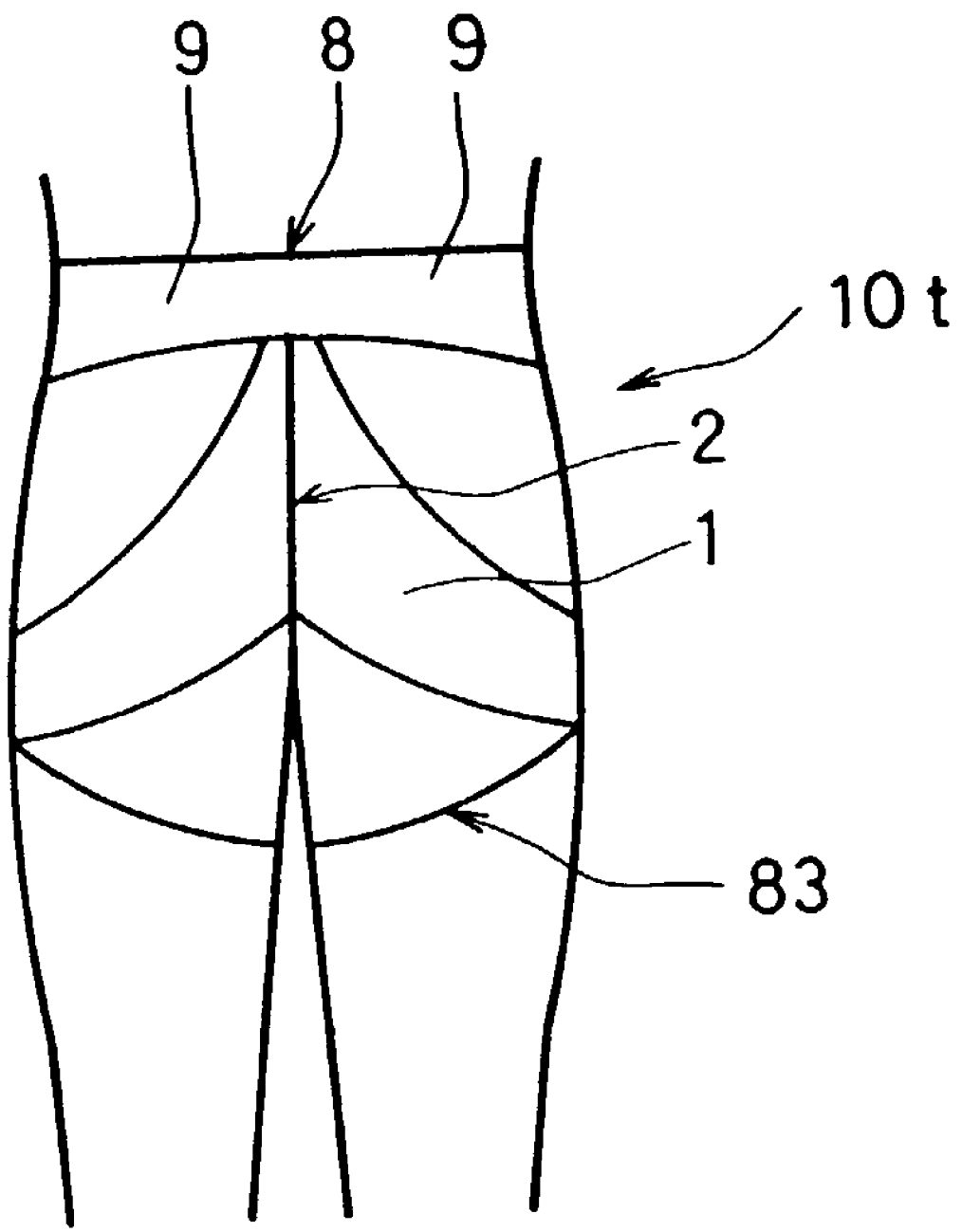
FIG. 69 is a rear view of the short type girdle of FIG. 67 in wearing condition.

Next, FIGS. 67 to 69 show a front view, a left side view and a rear view of still another embodiment of a short type girdle as a garment of the present invention in wearing condition, respectively. The short type girdle 10t shown in FIGS. 67 to 69 has, as a strong straining portion (A), a strong straining portion 1 in which right and left parts are connected at a position 2 on the back side of the girdle corresponding to from the fourth vertebra lumbalis to os sacrum of the wearer's body and which covers a region extending from the position 2 through the tops of the bulges of the buttocks or vicinities thereof in an approximately middle part of musculus gluteus maximus at right and left to the vicinity of trochanter major 3 approximately in the direction of muscle fibers of musculus gluteus maximus. Furthermore, the girdle 10t has, as a strong straining portion (C), a strong straining portion 6 in which right and left parts are connected at a position 4 on musculus rectus abdominis in hypogastric region and which covers a region extending obliquely upward from the position 4 on musculus rectus abdominis in hypogastric region approximately in the direction of muscle fibers of musculus obliquus externus abdominis at right and left to at least a position exceeding the sides of the wearer to the back side. Also, the girdle 10t has, as a strong straining portion (D), a strong straining portion 9 in which right and left parts are connected approximately in the vicinity of a position 8 at the back center of the waist and which covers a region extending from the vicinity of the position 8 at the back center of the waist through musculus latissimus dorsi 308 and musculus gluteus medius 309 at right and left and a part of musculus obliquus externus abdominis 302 to at least a position exceeding the sides of the wearer to the front side. The strong straining portions 6 and 9 are united to form a strong straining portion 11.

Further, the girdle 10t has, as a strong straining portion (B), a strong straining portion 5 that covers a region extending obliquely downward approximately in the direction of muscle fibers of musculus obliquus internus abdominis at right and left to the vicinity of trochanter major 3. Although the strong straining portion 5 of the girdle of this embodiment does not satisfy formally the condition "right and left parts are connected at a position 4 on musculus rectus abdominis in hypogastric region, and the strong straining portion 5 starts from the position 4 on musculus rectus abdominis in hypogastric region", the strong straining portion 5 is connected to the right and left lower sides of the strong straining portion 6, and a lower part of the strong straining portion 6 serves the function of the strong straining portion 5. Therefore, substantially, right and left parts of the strong straining portion 5 are connected at a position 4 on musculus rectus abdominis in hypogastric region, and it can be considered that the strong straining portion 5 starts from the position 4 on musculus rectus abdominis in hypogastric region. Thus, it is substantially equivalent to the condition. There exists only a seam line between the strong straining portions 5 and 6, and if the strong straining portions 5 and 6 are formed of a single integrated fabric, they are the same as those shown in FIG. 13. Therefore, it is equivalent to the united strong straining portions 5 and 6 shown in FIG. 13 in which a seam line is provided where the strong straining portions 5 and 6 cross each other along the external line of the strong straining portion 6. Numeral 83 indicates the lower end line on the back side of the main body of the short type girdle.

Thus, in the short type girdle 10t of this embodiment, the strong straining portion 1 passes through the tops of the bulges of the buttocks or vicinities thereof in the direction of muscle fibers of musculus gluteus maximus, and moreover, right and left parts of the strong straining portion 1 are connected at the position 2 on the back side of the girdle corresponding to from the fourth vertebra lumbalis to os sacrum of the wearer's body. Therefore, musculus gluteus maximus can be supported firmly in the direction of its muscle fibers. Thus, it can play a large role in supporting the rotating motion of the hips, preventing a decrease in the rotating angle of the hips, and stabilizing the pelvis in anterior-posterior direction. For an elderly person, it is effective in preventing falling down. Furthermore, it can play a large role in extending the hip joint in anterior-posterior direction when running, jumping, and climbing up a slope. Furthermore, because the strong straining portions 1 and 5 cover the vicinity of trochanter major 3, the functions of improving the joint between caput ossis femoris 204 and acetabulum and increasing the stability of the hip joint can be displayed. Furthermore, with the strong straining portion 5, the functions of supporting musculus rectus abdominis 301 in part and musculus obliquus internus abdominis, reducing lumbar lordosis, maintaining good posture, making youthful figure, and preventing generation of pains such as lumbar pains can be displayed.

Furthermore, with the strong straining portion 6, the functions of supporting musculus rectus abdominis 301 in part and musculus obliquus externus abdominis 302, reducing lumbar lordosis, maintaining good posture, making youthful figure, and preventing generation of pains such as lumbar pains can be displayed. Because the strong straining portions 6 and 9 are united to form the strong straining portion 11, a garment can be provided that displays more easily the functions of supporting more strongly the region from the vicinity of the position 8 at the back center of the waist through musculus latissimus dorsi 308 and musculus gluteus medius 309 at right and left and musculus obliquus externus abdominis 302, preventing backward inclination of the pelvis, and maintaining a stable position of the pelvis.

The present invention has been described above using specific examples of girdles, sports tights and bodysuits as embodiments of garments. However, the present invention is not limited only to these embodiments, and it is applicable to a garment comprising a stretch fabric, which covers at least a part of the lower body of a wearer, has a crotch part, and is worn by being fitted to the wearer's body, such as spats, leotards, swimsuits, and other garments.

In the present invention, a garment comprising a stretch fabric, which covers at least a part of the lower body of a wearer, has a crotch part, and is worn by being fitted to the wearer's body, wherein "the garment has a leg part cylindrically covering regio femoralis of the wearer's body to at least a position lower than the crotch part" refers to, for example, a garment having leg parts cylindrically covering regio femoralis or regio femoralis and regio cruris as indicated by the long type girdles shown in FIG. 1 and others or the sports tights shown in FIG. 34 and others. Although not illustrated, it is also applicable to spats, bodysuits, leotards, swimsuits and the like of the type having such leg parts. In such preferred embodiments of the present invention, by having leg parts cylindrically covering regio femoralis to at least a position lower than the crotch part, the entire length increases for the presence of the leg parts, and the garment is fixed and fitted to the body of the wearer more firmly. Accordingly, the straining force of a strong straining portion is exerted more effectively and easily. Particularly, the function of pressing trochanter major is displayed more effectively.

In the present invention, a garment comprising a stretch fabric, which covers at least a part of the lower body of a wearer, has a crotch part, and is worn by being fitted to the wearer's body, wherein "the position of the lower end of the garment is approximately the same as or higher than the position of the crotch part, and the garment does not have a leg part cylindrically covering regio femoralis to at least a position lower than the crotch part" refers to, for example, a garment that does not have a leg part cylindrically covering regio femoralis or regio femoralis and regio cruris but has holes for letting the legs of the wearer out as indicated by, for example, the short type girdles shown in FIGS. 55, 58 and others, or the bodysuit shown in FIG. 49. Such expression is used because the position of the lower end of this type of garment is usually approximately the same as or higher than the position of the crotch part. Although not illustrated, it is also applicable to leotards, swimsuits, and the like of this type that do not have a leg part cylindrically covering regio femoralis. A garment having this length to the lower end covers trochanter major, and the lower end line passes through the vicinity of trochanter major or a part lower than trochanter major. Because usually the lower end line is arranged so that it contacts closely with the body of the wearer, the function of pressing the region of trochanter major can be displayed effectively. Furthermore, in such an embodiment of the present invention, the garment does not have a leg part cylindrically covering regio femoralis. Therefore, a garment can be provided that is steamed little and thus can be worn favorably even in a hot season, and in addition has better wearing comfort because of little compressive feeling to regio femoralis.

A garment of the present invention comprises a stretch fabric and in part has a portion with a strong straining force (a strong straining portion).

In a garment of the present invention, a strong straining portion may be formed by laminating a stretch fabric having a predetermined shape on the main body of the garment and sewing it, or by laminating a stretch fabric having a predetermined shape on the main body of the garment and bonding it. According to these methods, a garment having durability can be produced easily. Of course, a lower leg protection garment of the present invention may be formed by preparing strong straining portions and other portions as respective parts of predetermined shapes and seaming them together. However, such sewing is complex and takes a lot of labor.

Furthermore, for example, a strong straining portion may be formed by stretching and laminating a stretch fabric having a predetermined shape on the main body of the garment and sewing or bonding it. These methods are favorable when applying a stronger straining force by the strong straining portion.

Furthermore, a strong straining portion may be formed by impregnating or coating a predetermined part of the main body fabric of the garment with a solution or emulsion of a synthetic resin or rubber having elasticity followed by drying, or by laminating a film of a synthetic resin or rubber having elasticity on a predetermined part of the main body fabric of the garment. According to these methods, a strong straining portion having a relatively small thickness can be obtained. As the synthetic resin having elasticity, suitable elastic resins such as polyurethane resins, polyester elastomer resins, etc. may be used.

Furthermore, a strong straining portion may be formed by changing the stitch of a stretch fabric that forms the main body of the garment to a stitch with a stronger straining force. According to this method, because lamination also is not necessary, a strong straining portion having a smaller thickness can be obtained. The definition of the method in which a strong straining portion is formed by changing the stitch as described also includes forming a strong straining portion by using, among the fiber materials forming the main body of the garment, an elastic fiber thicker than those used in other portions. According to this method, because lamination also is not necessary, a strong straining portion having a smaller thickness can be obtained.

Among the above-described methods for forming a strong straining portion, preferred are the method of laminating a stretch fabric having a predetermined shape on the main body of the garment and sewing it, and the method of stretching and laminating a stretch fabric having a predetermined shape on the main body of the garment and sewing it. According to these methods, the straining force of the stretch fabric sewn to the main body of the garment may be slightly smaller than, the same as, or larger than the straining force of the stretch fabric of the main body of the garment. This is because lamination of a stretch fabric on the main body of the garment results in increased straining force in the laminated part. The degree of the straining force of the fabric to be laminated may be chosen as appropriate depending on the type of the garment, intended use, preference of the wearer, etc.

Although not particularly limited, it is preferable that a strong straining portion has a straining force of 150 to 400 gf approximately in its length direction. Within this range of straining force, the functions of the present invention are exhibited effectively, and moreover compressive feeling is not too strong, and wearing comfort is excellent. Even if the straining force of a weak straining portion exceeds 150 gf, it is justified as long as the straining force is smaller than those of any of the strong straining portions formed in the garment.

A straining force is measured by a method using an Instron type universal tensile tester ("AUTOGRAPH AG-500D", manufactured by Shimadzu Corporation), in which stretch of a sample to 80% of its length (free length of the sample between grips) and recovery are repeated three times at a stretching rate of 300±20 mm/min, and the value of the straining force when recovering to 30% at the third time is read out among the values when stretching and recovering. It is preferable that the sample has a size of 2.5 cm in width and 16 cm in length, and has an upper grip length of 2.5 cm, a lower grip length of 3.5 cm, and a space between grips of 10 cm. If a sample of this size cannot be cut out from the garment to be measured, a smaller sample may be used. However, because measurement error increases as the size of the sample decreases, it is preferable that a sample as large as possible is cut out and measured. When a strong straining portion is formed by laminating a stretch fabric or the like on the garment main body, as a matter of course, it is necessary to use a laminated sample as the sample to be measured for its straining force.

The width of a strong straining portion in a garment of the present invention is not particularly limited, and it may be chosen as appropriate depending on the part where the strong straining portion is present, the strength of the straining force of the material used, the method of forming the strong straining portion, the degree or the part of disorder of the wearer, the aim of preventing disorder, the type of the sports played, whether the wearer is an adult or a child, etc. to the extent so that the object of the present invention is achieved. For example, it is preferable that the widest portion usually has a width of from about 5 to about 15 cm, more preferably from about 8 to about 13 cm. The width of other strong straining portion, for example a portion with the smallest width on the lateral side of regio femoralis, is usually from about 2 to about 10 cm, more preferably from about 4 to about 8 cm. Furthermore, for example, the width of the widest part in a strong straining portion for pressing abdomen as shown in FIGS. 19, 22, 46 or 49, etc. is naturally different depending on the size of the body of the wearer, but in general it is usually from about 8 to about 17 cm, more preferably from about 10 to about 14 cm. Of course, the width of a strong straining portion may be partially smaller or wider depending on the part to the extent so that the object of the present invention is achieved.

Furthermore, a garment of the present invention may preferably use, as a stretch fabric, a polyurethane fiber-containing power net that is a polyurethane fiber-containing stretch raschel knitted fabric, a polyurethane fiber-containing two-way stretch tricot knitted fabric that is a polyurethane fiber-containing tricot knitted fabric, etc. Therefore, compared with a conventional supporter using a relatively thick pile fabric, neoprene sheet, etc., a fabric having a thickness in a range as used when making a usual garment, e.g. from about 0.3 to about 0.8 mm, may be used. Thus, a garment can be provided that reduces the wearer's appearance little such as the figure when worn, fits well to the body, and has relatively good ventilation. The kind of the power net include, for example, a plain power net, satin power net, two-way stretch raschel, "TRISKIN" (trademark of Urabe Corporation), etc.

It is not necessary that all strong straining portions have the same straining force, and they may have different straining forces depending on the part.

The results of measuring the straining forces of strong straining portions and other weak straining portion with respect to each garment described in the above embodiments are as follows:

EXAMPLE 1 OF MEASUREMENT RESULT OF STRAINING FORCE

Example 1 of an embodiment in which a cloth was applied onto the main body fabric of a garment as shown in FIGS. 1 to 51 so that the part where the cloth was applied became a strong straining portion.

(1) Main body fabric:

"TRISKIN" (trademark of Urabe Corporation, two-way stretch power net knitted fabric), which uses a nylon yarn of 40 denier and in which one polyurethane elastic yarn of 140 denier and one polyurethane elastic yarn of 40 denier were inserted for each wale. The polyurethane elastic yarn of 40 denier was inserted while winding its way so as to reach a plurality of wales as described above.

---

Mixture ratio: 73.7 wt. % of the nylon yarn and 26.3 wt. % of the polyurethane elastic yarns
Stretching force: 140 gf    Contracting force: 129 gf
(2) Strong straining portion 1: A part where a cloth described below was applied onto the main body fabric described above (except for a part where double clothes were applied such as the part corresponding to trochanter major 3)
Cloth to be applied: One-way stretch power net, which uses a nylon yarn of 70 denier and in which one polyurethane elastic yarn of 280 denier was inserted for each wale.
Mixture ratio: 81 wt. % of the nylon yarn and 19 wt. % of the polyurethane elastic yarn
Stretching force: 280 gf    Contracting force: 240 gf
(3) Strong straining portion 2: (A part in the vicinity of trochanter major 3 where double clothes were applied, and coupled with the main body fabric, three clothes were laminated.)
Two clothes described above were applied onto the main body fabric described above and measured.
Stretching force: 423 gf    Contracting force: 354 gf

---

EXAMPLE 2 OF MEASUREMENT RESULT OF STRAINING FORCE

Example 2 of an embodiment in which a cloth was applied onto the main body fabric of a garment as shown in FIGS. 1 to 51 so that the part where the cloth was applied became a strong straining portion:

(1) Main body fabric:

Two-way stretch power net, which uses a nylon yarn of 40 denier and in which one polyurethane elastic yarn of 260 denier and one polyurethane elastic yarn of 40 denier were inserted for each wale. The polyurethane elastic yarn of 40 denier was inserted while winding its way so as to reach a plurality of wales as described above.

---

Mixture ratio: 73.7 wt. % of the nylon yarn and 26.3 wt. % of the polyurethane elastic yarns
Stretching force: 140 gf    Contracting force: 129 gf
(2) Strong straining portion 1: A part where a cloth described below was applied onto the main body fabric described above (except for a part where double clothes were applied such as the part corresponding to trochanter major 3)
Cloth to be applied: One-way stretch power net, which uses a nylon yarn of 40 denier and in which one polyurethane elastic yarn of 140 denier was inserted for each wale.
Mixture ratio: 80.4 wt. % of the nylon yarn and 19.6 wt. % of the polyurethane elastic yarn
Stretching force: 219 gf    Contracting force: 200 gf
(3) Strong straining portion 2: (A part in the vicinity of trochanter major 3 where double clothes were applied, and coupled with the main body fabric, three clothes were laminated.)

-continued

Two clothes described above were applied onto the main body fabric described above and measured.
Stretching force: 275 gf    Contracting force: 245 gf

EXAMPLE 3 OF MEASUREMENT RESULT OF STRAINING FORCE

A garment as shown in FIGS. 52 to 57 comprising a two-way stretch power net knitted fabric formed by a jacquard raschel machine, in which the stitch appearing on the front side of a ground knitted fabric was changed to form strong straining portions and a weak straining portion. Yarns used were as those described above with respect to FIGS. 52 to 57.

A ground knitted fabric using a nylon yarn of 20 denier, in which one polyurethane elastic yarn of 280 denier and one polyurethane elastic yarn of 40 denier were inserted for each wale. The polyurethane elastic yarn of 40 denier was inserted while winding its way so as to reach a plurality of wales as described above.

Mixture ratio: 80 wt. % of the nylon yarn and 20 wt. % of the polyurethane elastic yarns
(1) Weak straining portion (a part of a mesh-like net stitch)
Stretching force: 232 gf    Contracting force: 132 gf
(2) Third strong straining portion (a part of a satin-like net stitch)
Stretching force: 271 gf    Contracting force: 151 gf
(3) Second strong straining portion (a part of a satin-like net stitch
Stretching force: 291 gf    Contracting force: 157 gf
(3) First strong straining portion (a part of a satin-like net stitch corresponding to trochanter major)
Stretching force: 297 gf    Contracting force: 168 gf

INDUSTRIAL APPLICABILITY

The present invention provides garments that can exhibit the following functions:

(1) A garment of the present invention has a strong straining portion (A), in which right and left parts of the portion (A) are connected at a position on the back side of the garment corresponding to any region from os sacrum to vertebrae lumbalis of the wearer's body, and the portion (A) covers a region extending from said position through tops of bulges of the buttocks or vicinities thereof approximately in the direction of muscle fibers of musculus gluteus maximus at right and left to at least the vicinity of trochanter major. Thus, musculus gluteus maximus can be supported firmly in the direction of its muscle fibers. Therefore, the garment can play a large role in extending the hip joint, particularly for the stability of the pelvis in anterior-posterior direction, and supports rotating motion of the hips, prevents a decrease in the rotatable angle of the hips, and for an elderly person is effective in preventing falling down. The garment also can play a large role in extending the hip joint in anterior-posterior direction when running, jumping, and climbing up a slope. Furthermore, because the strong straining portion covers the vicinity of trochanter major, a garment having the functions of improving the joint between caput ossis femoris and acetabulum and increasing the stability of the hip joint can be provided.

(2) A preferred embodiment of the garment of the present invention further comprises a strong straining portion (B), wherein right and left parts of the portion (B) are connected at a position on the garment corresponding to musculus rectus abdominis in hypogastric region, and the portion (B) covers a region extending obliquely downward from the position on musculus rectus abdominis in hypogastric region approximately in the direction of muscle fibers of musculus obliquus internus abdominis at right and left to at least the vicinity of trochanter major. Thus, musculus rectus abdominis in part and musculus obliquus internus abdominis are supported further, so that a garment having additional functions of reducing lumbar lordosis, maintaining good posture, and preventing generation of pains such as lumbar pains can be provided.

(3) A preferred embodiment of the garment of the present invention further comprises a strong straining portion (C), wherein right and left parts of the portion (C) are connected at a position on the garment corresponding to musculus rectus abdominis in hypogastric region, and the portion (C) covers a region extending obliquely upward from the position on musculus rectus abdominis in hypogastric region approximately in the direction of muscle fibers of musculus obliquus externus abdominis at right and left to at least a position exceeding the sides of the wearer to the back side. Thus, musculus rectus abdominis in part and musculus obliquus externus abdominis are supported further, so that a garment having additional functions of reducing lumbar lordosis, maintaining good posture, making youthful figure, and preventing generation of pains such as lumbar pains can be provided.

(4) A preferred embodiment of the garment of the present invention further comprises a strong straining portion (D), wherein right and left parts of the portion (D) are connected approximately in the vicinity of a position on the garment corresponding to the back center of the waist; and the portion (D) covers a region extending from the vicinity of the position at the back center of the waist through musculus latissimus dorsi and musculus gluteus medius at right and left and a part of musculus obliquus externus abdominis to at least a position exceeding the sides of the wearer to the front side. Thus, a garment having additional functions of preventing backward inclination of the pelvis and assisting to maintain a stable position of the pelvis can be provided.

(5) A preferred embodiment of the garment of the present invention further comprises the portion (B) of the above item (2) and the portion (C) of the above item (3). Because the strong straining portions (B) and (C) are united, abdominal muscles are supported more strongly. Thus, a garment can be provided that exhibits more easily the functions of reducing lumbar lordosis, maintaining good posture, making youthful figure, and preventing generation of pains such as lumbar pains in addition to the functions described in the above item (1).

(6) A preferred embodiment of the garment of the present invention further comprises the portion (B) of the above item (2), the portion (C) of the above item (3), and the portion (D) of the above item (4). Because the strong straining portions (B) and (C) are united, abdominal muscles are supported more strongly. Thus, a garment can be provided that exhibits more easily the functions of reducing lumbar lordosis, maintaining good posture, making youthful figure, and preventing generation of pains such as lumbar pains in addition to the functions described in the above item (1). Furthermore, because it has the strong straining portion (D), the region from the vicinity of the position at the back center of the waist through musculus latissimus dorsi and musculus gluteus medius at right and left and musculus obliquus externus abdominis is supported more strongly, and a garment can be provided that exhibits more easily the functions of preventing backward inclination of the pelvis and maintaining a stable position of the pelvis.

(7) A preferred embodiment of the garment of the present invention further comprises a strong straining portion (F) for pressing abdomen and a strong straining portion (B), wherein the portion (F) has a main stretch direction in the longitudinal direction of the garment; the portion (F) covers the center of hypogastric region; an end of the portion (B) is connected to each of right and left lower sides of the portion (F); and the portion (B) covers a region extending obliquely downward from the right and left lower sides of the portion (F) approximately in the directions of muscle fibers of musculus obliquus internus abdominis at right and left to at least the vicinity of trochanter major. Thus, a garment having the functions of inhibiting the swelling of superfluous flesh of the abdomen and adjusting the shape of the abdomen more finely in addition to the functions described in the above items (1) and (2) can be provided.

(8) A preferred embodiment of the garment of the present invention further comprises a strong straining portion (F) for pressing abdomen and a strong straining portion (C), wherein the portion (F) has a main stretch direction in the longitudinal direction of the garment; the portion (F) covers the center of hypogastric region; an end of the portion (C) is connected to each of right and left upper sides of the portion (F); and the portion (C) covers a region extending obliquely upward from the right and left upper sides of the portion (F) approximately in the direction of muscle fibers of musculus obliquus externus abdominis at right and left to at least a position exceeding the sides of the wearer to the back side. Thus, a garment having the functions of inhibiting the swelling of superfluous flesh of the abdomen and adjusting the shape of the abdomen more finely in addition to the functions described in the above items (1) and (3) can be provided.

(9) A preferred embodiment of the garment of the present invention further comprises a strong straining portion (F) for pressing abdomen, a strong straining portion (B), and a strong straining portion (C), wherein the portion (F) has a main stretch direction in the longitudinal direction of the garment; the portion (F) covers the center of hypogastric region; an end of the portion (B) is connected to each of right and left lower sides of the portion (F); the portion (B) covers a region extending obliquely downward from the right and left lower sides of the portion (F) approximately in the direction of muscle fibers of musculus obliquus internus abdominis at right and left to at least the vicinity of trochanter major; an end of the portion (C) is connected to each of right and left upper sides of the portion (F); and the portion (C) covers a region extending obliquely upward from the right and left upper sides of the portion (F) approximately in the direction of muscle fibers of musculus obliquus externus abdominis at right and left to at least a position exceeding the sides of the wearer to the back side. Thus, a garment having the functions of inhibiting the swelling of superfluous flesh of the abdomen and adjusting the shape of the abdomen more finely in addition to the functions described in the above items (1) and (5) can be provided.

(10) In a preferred embodiment of the garment of the present invention, the portion indicated by the portion (A) is a strong straining portion (A2), which further covers a region extending from the vicinity of trochanter major toward regio femoralis anterior medialis through at least a part of any at least one musculus quadriceps femoris selected from musculus sartorius, musculus rectus femoris and musculus vastus medialis. Thus, the function of pressing trochanter major 3 is enhanced further, and the functions of improving the joint between caput ossis femoris and acetabulum and increasing the stability of the hip joint are enhanced further. Furthermore, because the strong straining portion (A2) supports musculus quadriceps femoris (musculus sartorius, musculus rectus femoris, musculus vastus medialis, etc.) approximately in the direction of their muscle fibers, a garment can be provided that has an additional function of when playing sports exhibiting a massage effect on these muscles in legs and encouraging recovery of these muscles from fatigue. Furthermore, when an elderly person wears it, the functions of preventing falling down and increasing walking stability are enhanced further.

(11) In a preferred embodiment of the garment of the present invention, the portion indicated by the portion (A) is a strong straining portion (A3), which further covers a region extending from the vicinity of trochanter major through the vicinity of tractus iliotibialis and/or musculus vastus lateralis in regio femoralis to a position a little higher than patella. Thus, the function of pressing trochanter major 3 is enhanced further, and the functions of improving the joint between caput ossis femoris and acetabulum and increasing the stability of the hip joint are enhanced further. Furthermore, because the strong straining portion (A3) supports tractus iliotibialis and/or musculus vastus lateralis approximately in the direction of their muscle fibers, a garment can be provided that has an additional function of when playing sports exhibiting a massage effect on these muscles in legs and speeding up flows of blood and lymphocyte thereby encouraging the recovery of these muscles from fatigue caused by exhaustion of energy or accumulation of lactic acid. Furthermore, when an elderly person wears it, the functions of preventing falling down and increasing walking stability are enhanced further.

(12) In a preferred embodiment of the garment of the present invention, the portion indicated by the portion (A) is a strong straining portion (A4), and the portion (A4) further covers a region extending from the vicinity of trochanter major through the vicinity of tractus iliotibialis and/or musculus vastus lateralis to patella, and further from patella through the vicinity of musculus gastrocnemius and/or musculus soleus in the regio cruris lateralis to the vicinity of an upper part of malleolus lateralis so as to support musculus gastrocnemius and musculus soleus. Thus, the function of pressing trochanter major 3 is enhanced further, and the functions of improving the joint between caput ossis femoris and acetabulum and increasing the stability of the hip joint are enhanced further. Also, because the strong straining portion (A4) supports tractus iliotibialis and/or musculus vastus lateralis approximately in the direction of their muscle fibers, and also supports musculus gastrocnemius and musculus soleus, a garment can be provided that has an additional function of when playing sports exhibiting a massage effect on these muscles in legs and encouraging recovery of these muscles from fatigue. Furthermore, when an elderly person wears it, the functions of preventing falling down and increasing walking stability are enhanced further.

(13) In a preferred embodiment of the garment of the present invention, the portion indicated by the portion (B) is a strong straining portion (B2), and the portion (B2) further covers a region extending from the vicinity of trochanter major through a lower part of the bulges of the buttocks. Thus, the function of pressing trochanter major 3 is enhanced further, and the functions of improving the joint between caput ossis femoris and acetabulum and increasing the stability of the hip joint are enhanced further. With the strong straining portion (B2), a garment having an additional function of keeping the bulges of the hips in a high position can be provided.

(14) In a preferred embodiment of the garment of the present invention, the portion indicated by the portion (B) is a strong straining portion (B3), and the portion (B3) further covers a region extending from the vicinity of trochanter major through at least a part of hamstrings in regio femoralis posterior. Thus, the function of pressing trochanter major 3 is enhanced further, and the functions of improving the joint between caput ossis femoris 204 and acetabulum and increasing the stability of the hip joint are enhanced further. Because the musculus biceps femoris, musculus semitendinosus and musculus semimembranosus, which are also called hamstrings, are supported approximately in the direction of muscles contraction, a garment can be provided that has additional functions of when playing sports encouraging recovery of these muscles in legs from fatigue and further enhancing the function of pressing the ground strongly backward in a running action, the function of jumping higher, the function of rising a foot, etc. When an elderly person wears it, the functions of preventing falling down and increasing walking stability are enhanced further.

(16) A preferred embodiment of the garment of the present invention further comprises a strong straining portion (E), wherein the portion (E) covers a region extending from an upper part of regio femoralis medialis through musculus vastus medialis to patella so as to support musculus vastus medialis, and further from patella through the vicinity of musculus gastrocnemius and/or musculus soleus in regio cruris medialis to the vicinity of an upper part of malleolus medialis so as to support musculus gastrocnemius and musculus soleus. Thus, musculus vastus medialis is supported approximately in the direction of its muscle fibers, and musculus gastrocnemius and musculus soleus also are supported. Therefore, a garment can be provided that has an additional function of when playing sports exhibiting a massage function on these muscles in legs and encouraging recovery of these muscles from fatigue. Furthermore, when an elderly person wears it, the functions of preventing falling down and increasing walking stability are enhanced further.

(17) In a preferred embodiment of the garment of the present invention, a strong straining portion is formed by laminating a cloth on the front side or back side of a main body fabric of the garment. Thus, the garment of the present invention is produced easily, and a garment having durability can be produced easily.

(18) In a preferred embodiment of the garment of the present invention, a strong straining portion is formed by changing a stitch for knitting a main body fabric of the garment to form a weak straining portion and a strong straining portion in patterns. Thus, a garment can be obtained that has a strong straining portion with a smaller thickness, has no difference in level between a strong straining portion and other portion, has excellent wearing comfort, and is excellent in appearance.

(19) In a preferred embodiment of the garment of the present invention, a strong straining portion is formed by laminating a film of a synthetic resin or rubber having elasticity on a predetermined part of a main body fabric of the garment or by impregnating or coating a predetermined part of a main body fabric of the garment with a solution or emulsion of a synthetic resin or rubber having elasticity followed by drying. Thus, a garment having a relatively thin strong straining portion can be obtained at a relatively low cost.

(20) In a preferred embodiment of the garment of the present invention, a strong straining portion has a straining force of 150 to 400 gf. Within this range of straining force, a garment can be provided that exhibits the functions of the present invention effectively and in which compressive feeling is not too strong and wearing comfort is excellent.

(21) In a preferred embodiment of the garment of the present invention, the stretch fabric is a knitted fabric selected from a two-way stretch tricot and a stretch raschel. Thus, compared with a conventional supporter using a relatively thick pile fabric, neoprene sheet, etc., a fabric having a thickness in a range as used when making a usual garment, e.g. from about 0.3 to about 0.8 mm, may be used. Therefore, a garment can be provided that reduces the wearer's appearance little such as the figure when worn, fits well to the body, and has relatively good ventilation.

(22) In a preferred embodiment of the garment of the present invention, the garment comprises a stretch fabric, covers at least a part of the lower body of a wearer, has a crotch part, and is worn by being fitted to the wearer's body, wherein the garment is selected from a girdle, spats, sports tights, bodysuit, leotard and swimsuit. These garments are worn by being contacted with the skin of the wearer more firmly or being fitted to a part relatively close to the skin. Thus, the above-described functions are displayed effectively, so that this garment is favorable.

(23) In a preferred embodiment of the garment of the present invention, the garment comprises a stretch fabric, covers at least a part of the lower body of a wearer, has a crotch part, and is worn by being fitted to the wearer's body, wherein the garment has a leg part cylindrically covering regio femoralis of the wearer's body to at least a position lower than the crotch part. By having a leg part cylindrically covering regio femoralis to at least a position lower than the crotch part, the entire length increases for the presence of the leg part, and the garment is fixed and fitted onto the body of the wearer more firmly. Accordingly, the straining force of a strong straining portion is exerted more effectively and easily. Particularly, the function of pressing trochanter major is displayed more effectively.

(24) In a preferred embodiment of the garment of the present invention, the garment comprises a stretch fabric, covers at least a part of the lower body of a wearer, has a crotch part, and is worn by being fitted to the wearer's body, wherein the position of a lower end of the garment is approximately the same as or higher than the position of the crotch part; and the garment does not have a leg part cylindrically covering regio femoralis to at least a position lower than the crotch part. A garment having this length to the lower end covers trochanter major, and the lower end line passes through the vicinity of trochanter major or a part lower than trochanter major. Because usually the lower end line is arranged so that it adheres closely to the body of the wearer, the function of pressing the region of trochanter major can be displayed effectively. Furthermore, a garment can be provided that is steamed little and thus can be worn favorably even in a hot season, and has better wearing comfort because of little compressive feeling to regio femoralis.

Accordingly, a garment of the present invention is useful as a garment that has good wearing comfort in common occasions such as during daily activities or when playing sports; can be worn easily by oneself even for an inexperienced person; has the functions of increasing the stability of the hip joint, making youthful figure and posture, and reducing lumbar lordosis; contributes to alleviating pains such as lumbar pains; and further has the functions of enabling the wearer to improve his/her performances when playing sports, and for an elderly person preventing falling down, by utilizing the function of expanding the range of motion of the lumbar region or the hip joint of a human body.

Having described preferred embodiments of the invention with reference to the accompanying drawings, it is to be understood that the invention is not limited to those precise embodiments, and that various changes and modifications maybe effected therein by one skilled in the art without departing from the scope or spirit of the invention as defined in the appended claims.

The invention claimed is:

1. A garment comprising a stretch fabric wherein the garment is adapted to cover at least a part of the lower body of a wearer, has a crotch part, and is adapted to be worn by being fitted to the wearer's body, wherein:
   the garment in part has a portion with a strong straining force;
   the portion with a strong straining force is a first strong straining portion;
   wearer's right and left parts of the first portion are connected at a position on the back side of the garment adapted to correspond to any region from os sacrum to vertebrae lumbalis of the wearer's body; and
   the first portion is adapted to cover a region extending from said position through the furthest dorsal point of bulge of each buttock in the direction of muscle fibers of musculus gluteus maximus to at least the vicinity of trochanter major at wearer's right and left.

2. The garment according to claim 1, further comprising a second strong straining portion, wherein:
   right and left parts of the second portion are connected at a position on the garment adapted to correspond to musculus rectus abdominis in a hypogastric region; and
   the second portion is adapted to cover a region extending obliquely downward from the position on musculus rectus abdominis in a hypogastric region approximately in the direction of muscle fibers of musculus obliquus internus abdominis at wearer's right and left to at least the vicinity of trochanter major.

3. The garment according to claim 2, further comprising:
   a fourth strong straining portion,
   wherein right and left parts of the fourth portion are connected at a position on the garment adapted to correspond to musculus rectus abdominis in a hypogastric region; and
   the fourth portion is adapted to cover a region extending obliquely upward from the position on musculus rectus abdominis in a hypogastric region approximately in the direction of muscle fibers of musculus obloquies externus abdominis at wearer's right and left to at least a position exceeding the sides of the wearer to the back side.

4. The garment according to claim 3, further comprising:
   a seventh strong straining portion,
   wherein right and left parts of the seventh portion are connected approximately in the vicinity of a position on the garment adapted to correspond to the back center of the waist; and
   the seventh portion is adapted to cover a region extending from the vicinity of the position at the back center of the waist through musculus latisimus dorsi and musculus gluteus medius at wearer's right and left and a part of musculus obloquies externus abdominis to at least a position exceeding the sides of the wearer to the front side.

5. The garment according to claim 4, further comprising:
   an eleventh strong straining portion in which the fourth portion and the seventh portion are united and continuous.

6. The garment according to claim 1, wherein:
   the second portion also has a fifth strong straining portion; and
   the fifth portion is adapted to cover further a region extending from the vicinity of trochanter major through a lower part of the bulges of the buttocks.

7. The garment according to claim 1, wherein:
   the second portion also has a sixth strong straining portion; and
   the sixth portion is adapted to cover further a region extending from the vicinity of trochanter major through at least a part of hamstrings in regio femoralis posterior.

8. The garment according to claim 1, wherein a strong straining portion is formed by laminating a cloth on the front side or back side of a main body fabric of the garment.

9. The garment according to claim 1, wherein a strong straining portion is formed by changing a stitch for knitting a main body fabric of the garment to form a weak straining portion and a strong straining portion in patterns.

10. The garment according to claim 1, wherein a strong straining portion is formed by laminating a film of a synthetic resin or rubber having elasticity on a predetermined part of a main body fabric of the garment or by impregnating or coating a predetermined part of a main body fabric of the garment with a solution or emulsion of a synthetic resin or rubber having elasticity followed by drying.

11. The garment according to claim 1, wherein a strong straining portion has a straining force of 150 to 400 gf.

12. The garment according to claim 1, wherein the stretch fabric is a knitted fabric selected from a two-way stretch tricot and a stretch raschel.

13. The garment according to claim 1, wherein:
   the garment comprises a stretch fabric,
   the garment is adapted to cover at least a part of the lower body of a wearer, has a crotch part, and is worn by being fitted to the wearer body, and
   the garment is selected from a girdle, spats, sports tights, bodysuit, leotard and swimsuit.

14. The garment according to claim 1, wherein:
   the garment comprises a stretch fabric,
   the garment is adapted to cover at least a part of the lower body of a wearer, has a crotch part, and is worn by being fitted to the wearer body, and
   the garment has a leg part for cylindrically covering regio femoralis of the wearer body to at least a position lower than the crotch part.

15. The garment according to claim 1, wherein:
   the garment comprises a stretch fabric,
   the garment is adapted to cover at least a part of the lower body of a wearer, has a crotch part, and is worn by being fitted to the wearer body,
   the position of a lower end of the garment is approximately the same as or higher than the position of the crotch part; and
   the garment does not have a leg part for cylindrically covering regio femoralis to at least a position lower than the crotch part.

16. A garment comprising:
   a stretch fabric wherein the garment is adapted to cover at least a part of the lower body of a wearer, has a crotch part, and is adapted to be worn by being fitted to the wearer's body; a first strong straining portion with a strong straining force, wherein wearer's right and left parts of the first portion are connected at a position on the back side of the garment and adapted to correspond to any region from os sacrum to vertebrae lumbalis of the wearer's body;

the first portion is adapted to cover a region extending from said position through tops of bulges of the buttocks or vicinities thereof approximately in the direction of muscle fibers of musculus gluteus maximus at wearer's right and left to at least the vicinity of trochanter major;

a second strong straining portion; and a third strong straining portion adapted to press the abdomen;

wherein the third portion has a main stretch direction in the longitudinal direction of the garment;

the third portion being adapted to cover the center of hypograstric region;

an end of the second portion is connected to each of the right and left lower sides of the third portion; and the second portion being adapted to cover a region extending obliquely downward from the right and left lower sides of the third portion approximately in the directions of muscle fibers of musculus obliquus internus abdonimis at wearer's right and left to at least the vicinity of trochanter major.

17. A garment comprising:

a stretch fabric wherein the garment is adapted to cover at least a part of the lower body of a wearer, has a crotch part, and is adapted to be worn by being fitted to the wearer's body;

a first strong straining portion with a strong straining force, wherein right and left parts of the first portion are connected at a position on the back side of the garment adapted to correspond to any region from os sacrum to vertebrae lumbalis of the wearer's body;

the first portion is adapted to cover a region extending from said position through tops of bulges of the buttocks or vicinities thereof approximately in the direction of muscle fibers of musculus gluteus maximus at wearer's right and left to at least the vicinity of trochanter major;

a third strong straining portion adapted to press the abdomen; and a fourth strong straining portion, wherein the third portion has a main stretch direction in the longitudinal direction of the garment;

the third portion is adapted to cover the center of a hypogastric region;

an end of the fourth portion is connected to each of right and left upper sides of the third portion; and the fourth portion is adapted to cover a region extending obliquely upward from the right and left upper sides of the third portion approximately in the direction of muscle fibers of musculus obliquus externus abdominis at wearer's right and left to at least a position exceeding the sides of the wearer to the back side.

18. A garment comprising:

a stretch fabric wherein the garment is adapted to cover at least a part of the lower body of a wearer, has a crotch part, and is adapted to be worn by being fitted to the wearer's body;

a first strong straining portion with a strong straining force, wherein right and left parts of the first portion are connected at a position on the back side of the garment adapted to correspond to any region from os sacrum to vertebrae lumbalis of the wearer's body;

the first portion is adapted to cover a region extending from said position through tops of bulges of the buttocks or vicinities thereof approximately in the direction of muscle fibers of musculus gluteus maximus at wearer's right and left to at least the vicinity of trochanter major;

a second strong straining portion;

a third strong straining portion is adapted to press the abdomen, and a fourth strong straining potion, wherein the third portion has a main stretch direction in the longitudinal direction of the garment;

the third portion is adapted to cover the center of a hypogastric region;

an end of the second portion is connected to each of right and left lower sides of the third portion;

the second portion is adapted to cover a region extending obliquely downward from the right and left lower sides of the third portion approximately in the direction of muscle fibers of musculus obliquus internus abdominis at wearer's right and left to at least the vicinity of trochanter major;

an end of the fourth portion is connected to each of right and left upper sides of the third portion; and the fourth portion is adapted to cover a region extending obliquely upward from the right and left upper sides of the third portion approximately in the direction of muscle fibers of musculus obliquus externus abdominis at wearer's right and left to at least a position exceeding the sides of the wearer to the back side.

19. A garment comprising:

a stretch fabric wherein the garment is adapted to cover at least a part of the lower body of a wearer, has a crotch part, and is adapted to be worn by being fitted to the wearer's body;

a first strong straining portion with a strong straining force, wherein right and left parts of the first portion are connected at a position on the back side of the garment adapted to correspond to any region from os sacrum to vertebrae lumbalis of the wearer's body;

the first portion is adapted to cover a region extending from said position through tops of bulges of the buttocks or vicinities thereof approximately in the direction of muscle fibers of musculus gluteus maximus at wearer's right and left to at least the vicinity of trochanter major; and a fourth strong straining portion, wherein right and left parts of the fourth portion are connected at a position on the garment adapted to correspond to musculus rectus abdominis in a hypogastric region; and the fourth portion is adapted to cover a region extending obliquely upward from the position on musculus rectus abdominis in hypogastric region approximately in the direction of muscle fibers of musculus obloquies externus adominis at wearer's right and left to at least a position exceeding the sides of the wearer to the back side.

20. A garment comprising:

a stretch fabric wherein the garment is adapted to cover at least a part of the lower body of a wearer, has a crotch part, and is adapted to be worn by being fitted to the wearer's body;

a first strong straining portion with a strong straining force, wherein right and left parts of the first portion are connected at a position on the back side of the garment adapted to correspond to any region from os sacrum to vertebrae lumbalis of the wearer's body;

the first portion is adapted to cover a region extending from said position through tops of bulges of the buttocks or vicinities thereof approximately in the direction of muscle fibers of musculus gluteus maximus at wearer's right and left to at least the vicinity of trochanter major; and a seventh strong straining portion, wherein right and left parts of the seventh portion are connected approximately in the vicinity of a position on the garment adapted to correspond to the back center of the waist; and the seventh portion is adapted to cover a region extending from the vicinity of the position at the back center of the waist through musculus latisimus dorsi and musculus gluteus medius at wearer's right and left and a part of musculus obloquies externus abdominis to at least a position exceeding the sides of the wearer to the front side.

21. A garment comprising:

a stretch fabric wherein the garment is adapted to cover at least a part of the lower body of a wearer, has a crotch part, and is adapted to be worn by being fitted to the wearer's body;

a first strong straining portion with a strong straining force, wherein right and left parts of the first portion are connected at a position on the back side of the garment adapted to correspond to any region from os sacrum to vertebrae lumbalis of the wearer's body; and the first portion is adapted to cover a region extending from said position through tops of bulges of the buttocks or vicinities thereof approximately in the direction of muscle fibers of musculus gluteus maximus at wearer's right and left to at least the vicinity of trochanter major;

the first portion also has an eighth strong straining portion, wherein the eighth portion is adapted to cover further a region extending from the vicinity of trochanter major toward regio femoralis anterior medialis through at least a part of any at least one musculus quadriceps femoris selected from musculus sartorius, musculus rectus femoris and musculus vastus medialis.

22. A garment comprising:

a stretch fabric wherein the garment is adapted to cover at least a part of the lower body of a wearer, has a crotch part, and is adapted to be worn by being fitted to the wearer's body;

a first strong straining portion with a strong straining force, wherein right and left parts of the first portion are connected at a position on the back side of the garment adapted to correspond to any region from os sacrum to vertebrae lumbalis of the wearer's body; and the first portion is adapted to cover a region extending from said position through tops of bulges of the buttocks or vicinities thereof approximately in the direction of muscle fibers of musculus gluteus maximus at wearer's right and left to at least the vicinity of trochanter major;

the first portion also has a ninth strong straining portion, wherein the ninth portion is adapted to cover further a region extending from the vicinity of trochanter major through the vicinity of tractus iliotibialis and/or musculus vastus lateralis in regio femoralis to a position a little higher than patella.

23. A garment comprising:

a stretch fabric wherein the garment is adapted to cover at least a part of the lower body of a wearer, has a crotch part, and is adapted to be worn by being fitted to the wearer's body;

a first strong straining portion with a strong straining force, wherein right and left parts of the first portion are connected at a position on the back side of the garment adapted to correspond to any region from os sacrum to vertebrae lumbalis of the wearer's body; and the first portion is adapted to cover a region extending from said position through tops of bulges of the buttocks or vicinities thereof approximately in the direction of muscle fibers of musculus gluteus maximus at wearer's right and left to at least the vicinity of trochanter major;

the first portion also has an tenth strong straining portion; and the tenth portion is adapted to cover further a region extending from the vicinity of trochanter major through the vicinity of tractus iliotibialis and/or musculus vastus lateralis to patella, and further from patella through the vicinity of musculus gastrocnemius and/or musculus soleus in the regio cruris lateralis to the vicinity of an upper part of malleolus lateralis so as to support musculus gastrocnemius and musculus soleus.

24. The garment according to claim 23, further comprising a twelfth strong straining portion, wherein:

the twelfth portion is adapted to cover a region extending from an upper part of regio femoralis medialis through musculus vastus medialis to patella so as to support musculus vastus medialis, and further from patella through the vicinity of one of musculus gastrocnemius and musculus soleus in regio cruris medialis to the vicinity of an upper part of malleolus medialis so as to support musculus gastrocnemius and musculus soleus.

25. A garment comprising a stretch fabric wherein the garment is adapted to cover at least a part of the lower body of a wearer, has a crotch part, and is adapted to be worn by being fitted to the wearer's body, wherein:

the garment in part has a portion with a strong straining force;

the portion with a strong straining force is a first strong straining portion;

wearer's right and left parts of the first portion are connected at a position on the back side of the garment adapted to correspond to any region from os sacrum to vertebrae lumbalis of the wearer's body; and the first portion is adapted to cover a region starting from said position, running in the direction of the muscle fibers of musculus gluteus maximus to extend over the furthest posterior point of each buttock at right and left sides of the garment, and reaching at least the vicinity of trochanter major.

* * * * *